United States Patent
Kim et al.

(10) Patent No.: US 12,098,206 B2
(45) Date of Patent: Sep. 24, 2024

(54) PDGF RECEPTOR ANTIBODY AND USE THEREOF

(71) Applicants: Seoul National University R&DB Foundation, Seoul (KR); Ewha University—Industry Collaboration Foundation, Seoul (KR)

(72) Inventors: Soohyun Kim, Seoul (KR); Hyori Kim, Seoul (KR); Dong Hyun Jo, Seoul (KR); Jeong Hun Kim, Seoul (KR); Suree Kim, Seoul (KR); Dongmin Kang, Seoul (KR); Dobeen Hwang, Seoul (KR); Junho Chung, Seongnam-si (KR)

(73) Assignees: SEOUL NATIONAL UNIVERSITY R&DB FOUNDATION, Seoul (KR); EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 792 days.

(21) Appl. No.: 17/281,058

(22) PCT Filed: Oct. 7, 2019

(86) PCT No.: PCT/KR2019/013122
§ 371 (c)(1),
(2) Date: Mar. 29, 2021

(87) PCT Pub. No.: WO2020/071881
PCT Pub. Date: Apr. 9, 2020

(65) Prior Publication Data
US 2021/0371536 A1 Dec. 2, 2021

Related U.S. Application Data

(60) Provisional application No. 62/741,733, filed on Oct. 5, 2018.

(51) Int. Cl.
*C07K 16/28* (2006.01)
*A61K 39/00* (2006.01)
*A61K 47/68* (2017.01)
*A61P 35/00* (2006.01)
*C07K 16/44* (2006.01)

(52) U.S. Cl.
CPC ...... *C07K 16/2863* (2013.01); *A61K 47/6803* (2017.08); *A61K 47/6849* (2017.08); *A61P 35/00* (2018.01); *C07K 16/44* (2013.01); *A61K 2039/505* (2013.01); *C07K 2317/31* (2013.01); *C07K 2317/622* (2013.01)

(58) Field of Classification Search
CPC ........... C07K 16/2863; C07K 16/44; C07K 2317/31; C07K 2317/622; C07K 2317/73; C07K 2317/77; A61K 47/6803; A61K 47/6849; A61K 2039/505; A61K 47/555; A61K 47/6879; A61K 47/6891; A61K 45/06; A61K 47/6801; A61P 35/00; A61P 27/02
See application file for complete search history.

(56) References Cited

U.S. PATENT DOCUMENTS

| | | | |
|---|---|---|---|
| 8,008,448 | B2 | 8/2011 | Park et al. |
| 2008/0260738 | A1 | 10/2008 | Moore et al. |
| 2011/0177074 | A1 | 7/2011 | Sivakumar et al. |
| 2014/0193402 | A1 | 7/2014 | Wiegand et al. |
| 2015/0376271 | A1 | 12/2015 | Perlroth et al. |
| 2016/0311909 | A1 | 10/2016 | Sivakumar et al. |
| 2017/0119882 | A1 | 5/2017 | Saha et al. |

FOREIGN PATENT DOCUMENTS

| | | |
|---|---|---|
| CN | 101707882 | 5/2010 |
| CN | 102250246 | 11/2011 |
| CN | 102250249 | 11/2011 |
| CN | 104936614 | 9/2015 |
| CN | 105026433 | 11/2015 |
| CN | 107353342 | 11/2017 |
| KR | 20090130382 | 12/2009 |
| KR | 20150103682 | 9/2015 |
| KR | 20160104628 | 9/2016 |
| RU | 2016141285 | 4/2018 |
| WO | 2008-130704 | 10/2008 |
| WO | 2009-120922 | 10/2009 |
| WO | 2014-109999 | 7/2014 |
| WO | 2015200905 | 12/2015 |
| WO | 2017-001990 | 1/2017 |

OTHER PUBLICATIONS

Mandal et al. Ocular delivery of proteins and peptides: Challenges and novel formulation approaches. Adv Drug Deliv Rev. 2018; 126: 67-95 (Year: 2018).*
Esposito et al. Aptamer Chimeras for Therapeutic Delivery: The Challenging Perspectives. Genes (Basel). 2018; 9(11):529. (Year: 2018).*
Soohyun Kim at al., "Bispecific anti-mPDGFRβ x cotinine scFv-C κ-scFv fusion protein and cotinine-duocarmycin can form antibody-drug conjugate-like complexes that exert cytotoxicity against mPDGFRβ expressing cells", Methods, Feb. 1, 2019;154:125-135. doi: 10.1016/j.ymeth.2018.10.002. Epub Oct. 4, 2018.
Junyeong Jin et al., "An anti-EGFR x cotinine bispecific antibody complexed with cotinine-conjugated duocarmycin inhibits growth of EGFR-positive cancer cells with KRAS mutations", Experimental and Molecular Medicine 50(5):67, May 24, 2018.
Hyori Kim et al., "Application of bispecific antibody against antigen and hapten for immunodetection and immunopurification", Experimental & Molecular Medicine vol. 45, p. 43 (2013), Sep. 27, 2013.

(Continued)

*Primary Examiner* — Brad Duffy
*Assistant Examiner* — Amber K Faust
(74) *Attorney, Agent, or Firm* — LEX IP MEISTER, PLLC

(57) ABSTRACT

The present invention relates to an antibody against a PDGF receptor, an antibody-drug conjugate in which a chemotherapeutic agent is conjugated to the antibody against PDGF receptor, and a use of prevention or treatment of ocular neovascular diseases.

23 Claims, 32 Drawing Sheets
Specification includes a Sequence Listing.

(56) References Cited

OTHER PUBLICATIONS

Nam-Kyung Lee et al., "Cell-type specific potent Wnt signaling blockade by bispecific antibody", Sci Rep 8, 766 (2018), Jan. 15, 2018, https://doi.org/10.1038/s41598-017-17539-z.
EPO, Search Report of EP 19868599.2 dated Jun. 2, 2022.
John McCafferty et al., "Phage antibodies: filamentous phage displaying antibody variable domains", Nature, vol. 348, p. 552-553, Dec. 6, 1990.
Claus Zehetner et al., "Systemic Upregulation of PDGF-B in Patients With Neovascular AMD", Invest Ophthalmol Vis Sci. 55 (2014) 337-44.
Ann Hellström et al., "Retinopathy of prematurity", Lancet. 382 (2013) 1445-57, Oct. 26, 2013.
Vincent Lambert et al., "Laser-induced choroidal neovascularization model to study age-related macular degeneration in mice", Nat Protoc 8, 2197-2211 (2013), Oct. 17, 2013.
Yureeda Qazi et al., "Mediators of ocular angiogenesis", J Genet. Dec. 2009 ; 88(4): 495-515.
Zachary K. Goldsmith et al., "Targeting the Platelet-Derived Growth Factor-beta Stimulatory Circuitry to Control Retinoblastoma Seeds", Invest Ophthalmol Vis Sci. 2018;59:4486-4495. https://doi.org/10.1167/iovs.18-24359.
Inga Nazarenko et al., "PDGF and PDGF receptors in glioma", Upsala Journal of Medical Sciences. 2012; 117: 99-112, Apr. 17, 2012. DOI: 10.3109/03009734.2012.665097.
Shiki Fujino et al., "Platelet-derived growth factor receptor-β gene expression relates to recurrence in colorectal cancer", Oncology Reports 3 2178 9: 2178-2184, 2018. DOI: 10.3892/or.2018.6290.
Sabrina Basciani et al., "Platelet-Derived Growth Factor Receptor β-Subtype Regulates Proliferation and Migration of Gonocytes", Endocrinology 149(12):6226-6235. doi: 10.1210/en.2008-0349.
Janna Paulsson et al., "High expression of stromal PDGFRβ is associated with reduced benefit of tamoxifen in breast cancer", J Path: Clin Res Jan. 2017; 3: 38-43, Aug. 16, 2016.
Stefanie Avril et al., "Increased PDGFR-beta and VEGFR-2 protein levels are associated with resistance to platinum-based chemotherapy and adverse outcome of ovarian cancer patients", Oncotarget, 2017, vol. 8, (No. 58), pp. 97851-97861, Jun. 8, 2017.
Marius Raica et al., "Platelet-Derived Growth Factor (PDGF)/ PDGF Receptors (PDGFR) Axis as Target for Antitumor and Antiangiogenic Therapy", Pharmaceuticals Mar. 2010, 572-599, Mar. 11, 2010. doi: 10.3390/ph3030572.
Yujean Lee et al., "An antibody reactive to the Gly63-Lys68 epitope of NT-proBNP exhibits O-glycosylation independent binding", Experimental & Molecular Medicine (2014) 46, e114; doi:10.1038/emm.2014.57.
Sharon E. Reed et al., "Transfection of mammalian cells using linear polyethylenimine is a simple and effective means of producing recombinant adeno-associated virus vectors", Journal of Virological Methods 138 (2006) 85-98, doi:10.1016/j.jviromet.2006.07.024.
Soomin Yoon et al., "Bispecific Her2 x cotinine antibody in combination with cotinine- (histidine)2-iodine for the pre-targeting of Her2-positive breast cancer xenografts", J Cancer Res Clin Oncol (2014) 140:227-233, DOI 10.1007/s00432-013-1548-4.
C.F. Barbas III, D.R. Burton, J.K. Scott, G.J. Silverman, Phage display—a laboratory manual, Cold Spring Harbor Laboratory Press, New York, 2001.
Wonjun Yang et al., "Next-generation sequencing enables the discovery of more diverse positive ciones from a phage-displayed antibody library", Experimental & Molecular Medicine (2017) 49, e308; doi:10.1038/emm.2017.22.
Jung Mi Lim et al., "Control of the pericentrosomal H2O2 level by peroxiredoxin I is critical for mitotic progression", J. Cell Biol., vol. 210, No. 1, 23-33.
Sunyoung Park et al., "Cotinine-conjugated aptamer/anti-cotinine antibody complexes as a novel affinity unit for use in biological assays", Experimental and Molecular Medicine, vol. 44, No. 9, 554-561, Sep. 2012.
Junyeong Jin et al., "An anti-EGFR x cotinine bispecific antibody complexed with cotinine-conjugated duocarmycin inhibits growth of EGFRpositive cancer cells with KRAS mutations", Experimental & Molecular Medicine (2018) 50:67. DOI 10.1038/s12276-018-0096-z.
Sunyoung Park et al., "A sensitive enzyme immunoassay for measuring cotinine in passive smokers", Clinica Chimica Acta 411 (2010) 1238-1242, doi:10.1016/j.cca.2010.04.027.
Soohyun Kim et al., "Bispecific anti-mPDGFRβ x cotinine scFv-Cx-scFv fusion protein and 1 cotinine-duocarmycin can form antibody-drug conjugate-like complexes 2 that exert cytotoxicity against mPDGFRβ expressing cells.", 24. Journal methods_bispecific antibody.
KIPO, PCT Search Report & Written Opinion of PCT/KR2019/ 013122 dated Jan. 23, 2020.
Stefan Dengl et al., "Engineered hapten-binding antibody derivatives for modulation of pharmacokinetic properties of small molecules and targeted payload delivery", Immunological Reviews, 2016, vol. 270, pp. 165-177.
Rospatent, Office Action of RU 2021111430 dated Sep. 20, 2021.

\* cited by examiner

[Fig. 1a]
Bispecific scFv- C$_\kappa$-scFv
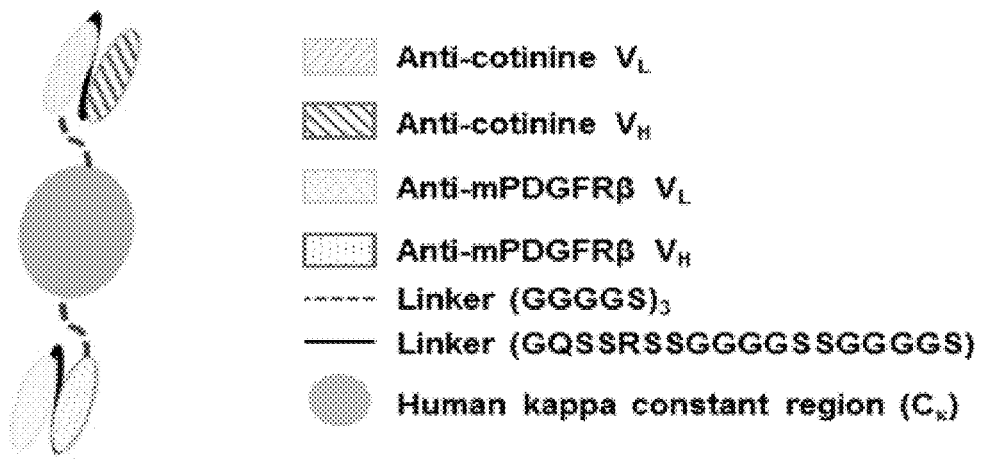
Cot-duo
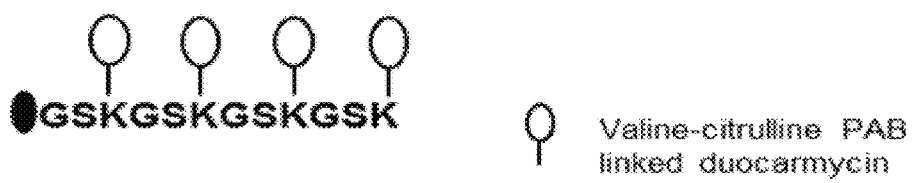
Cot-duo-cot
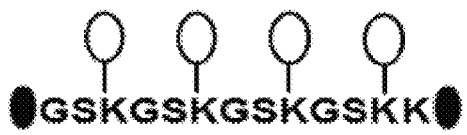

[Fig. 1b]
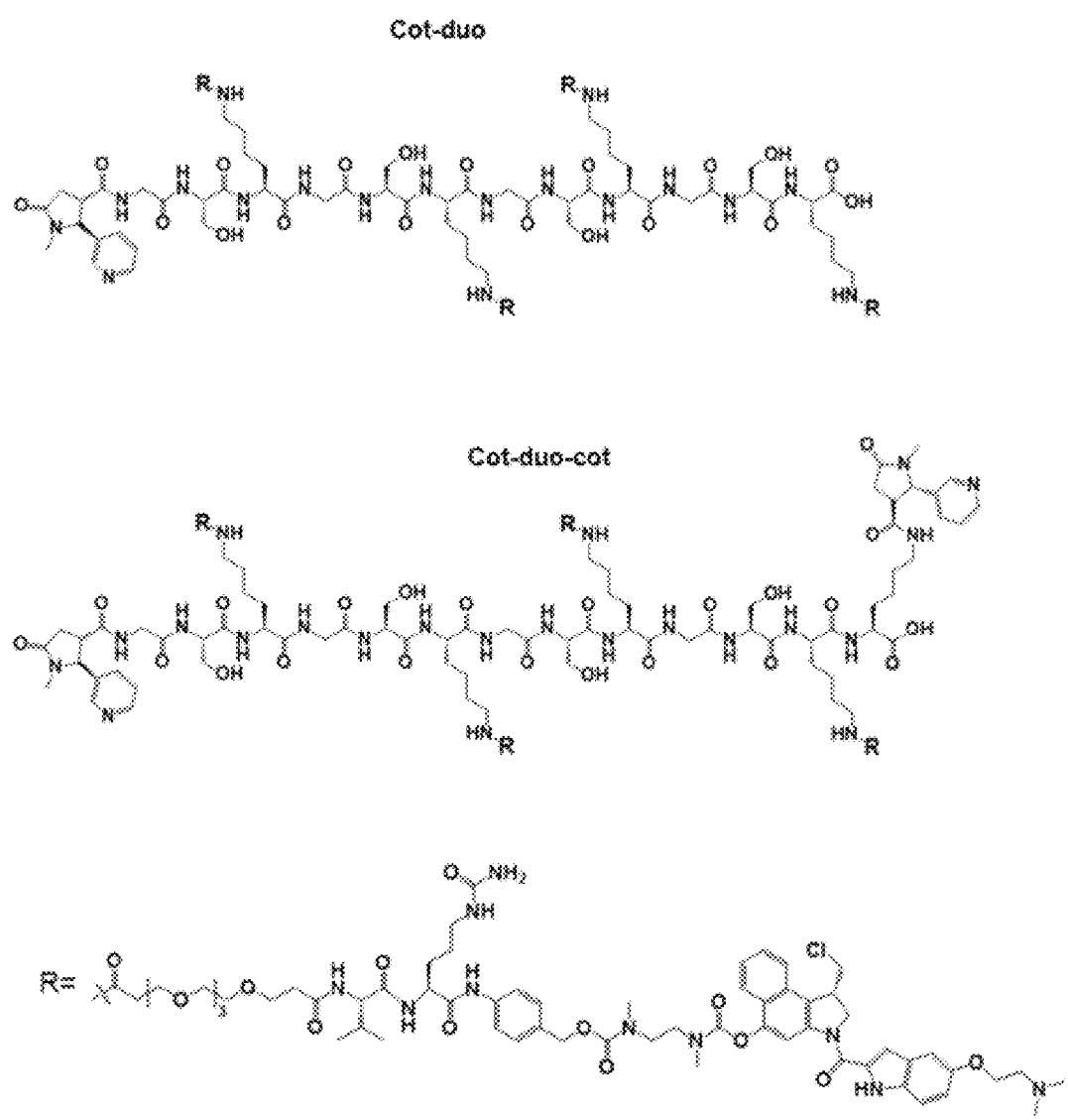

[Fig. 2]
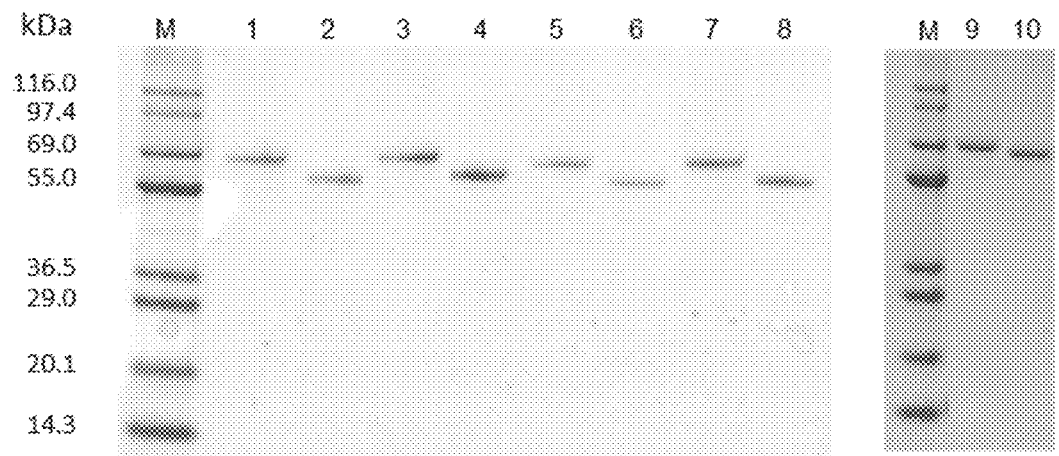
[Fig. 3a]
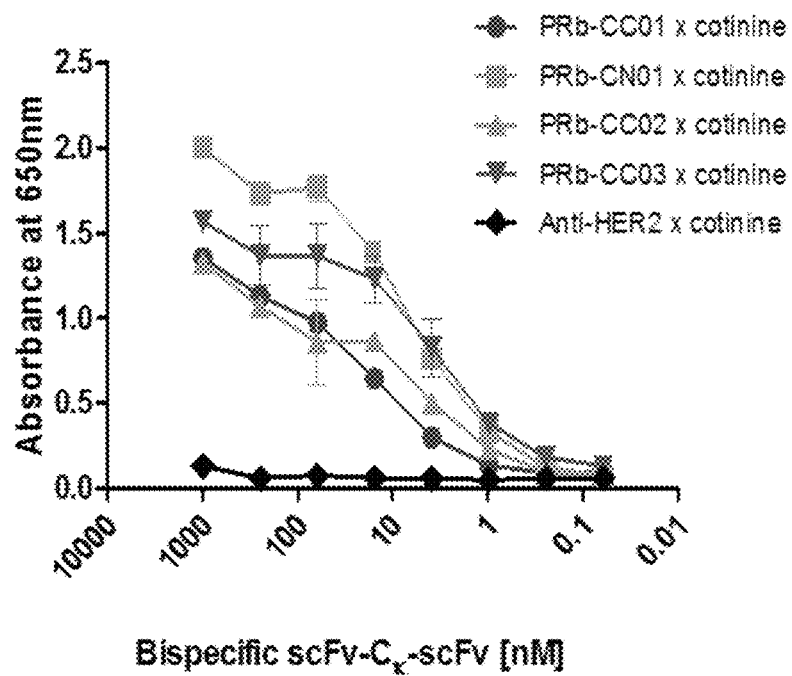

[Fig. 3b]
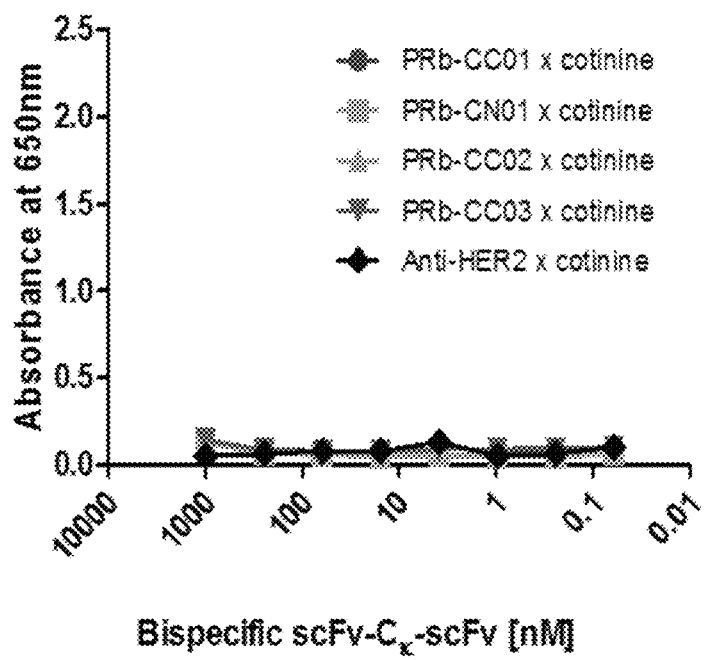
[Fig. 3c]
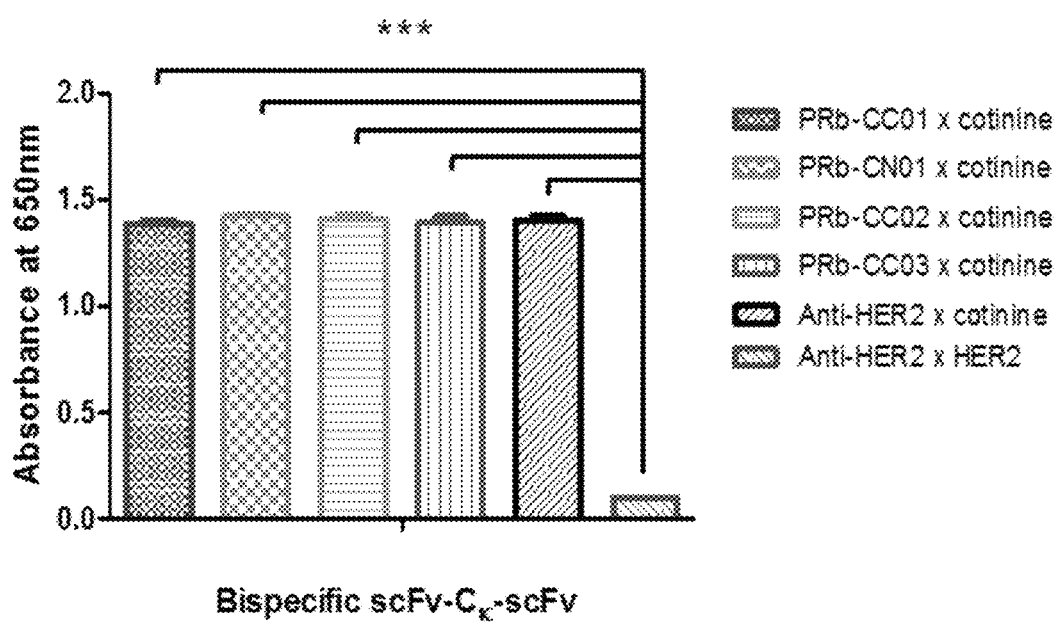

[Fig. 3d]
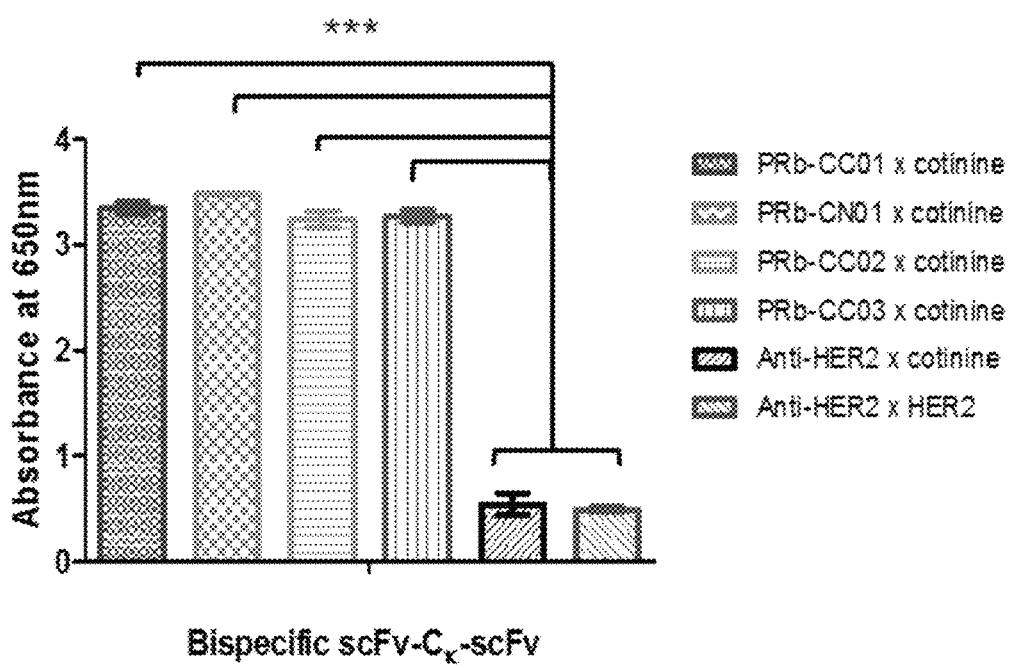

[Fig. 4a]
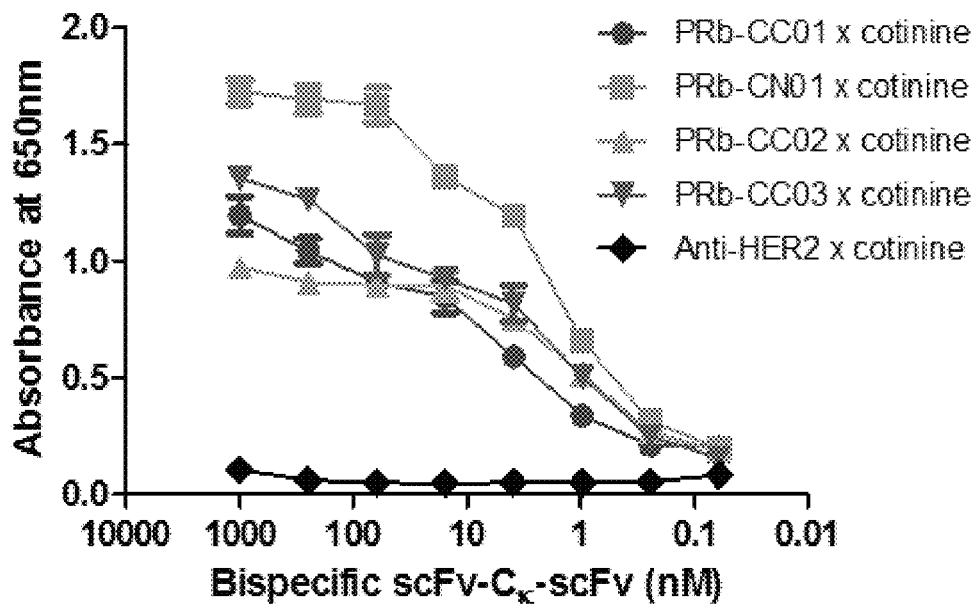
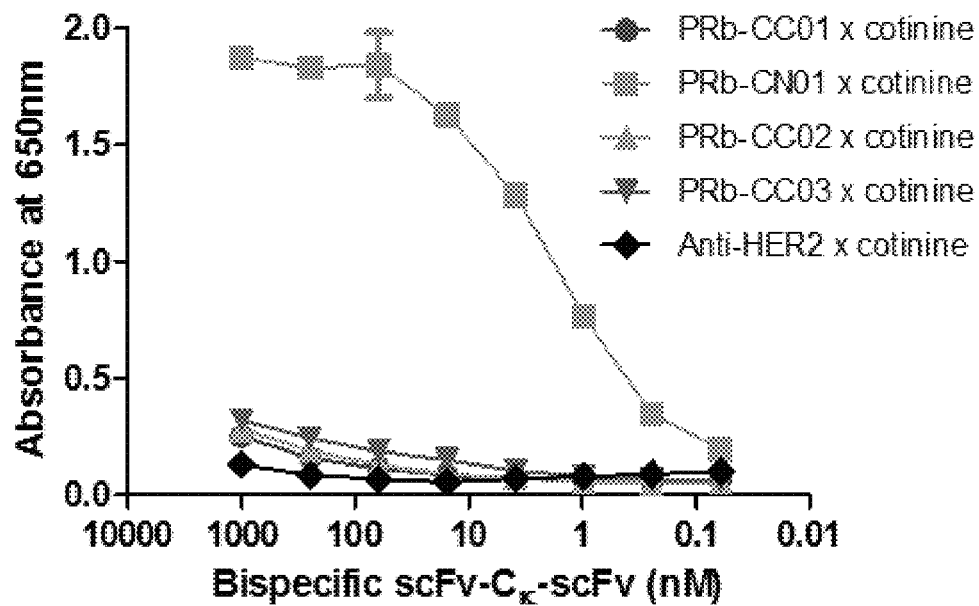

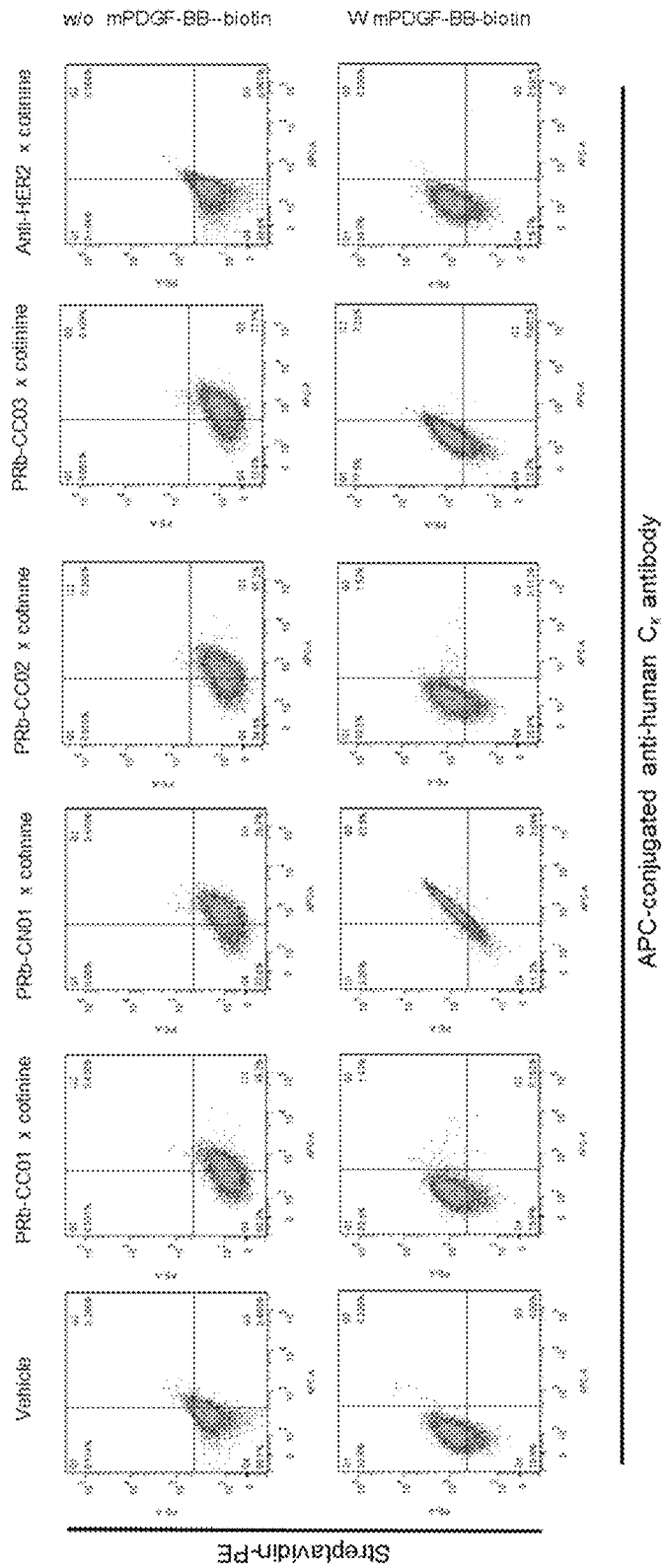
[Fig. 4b]

[Fig. 4c]
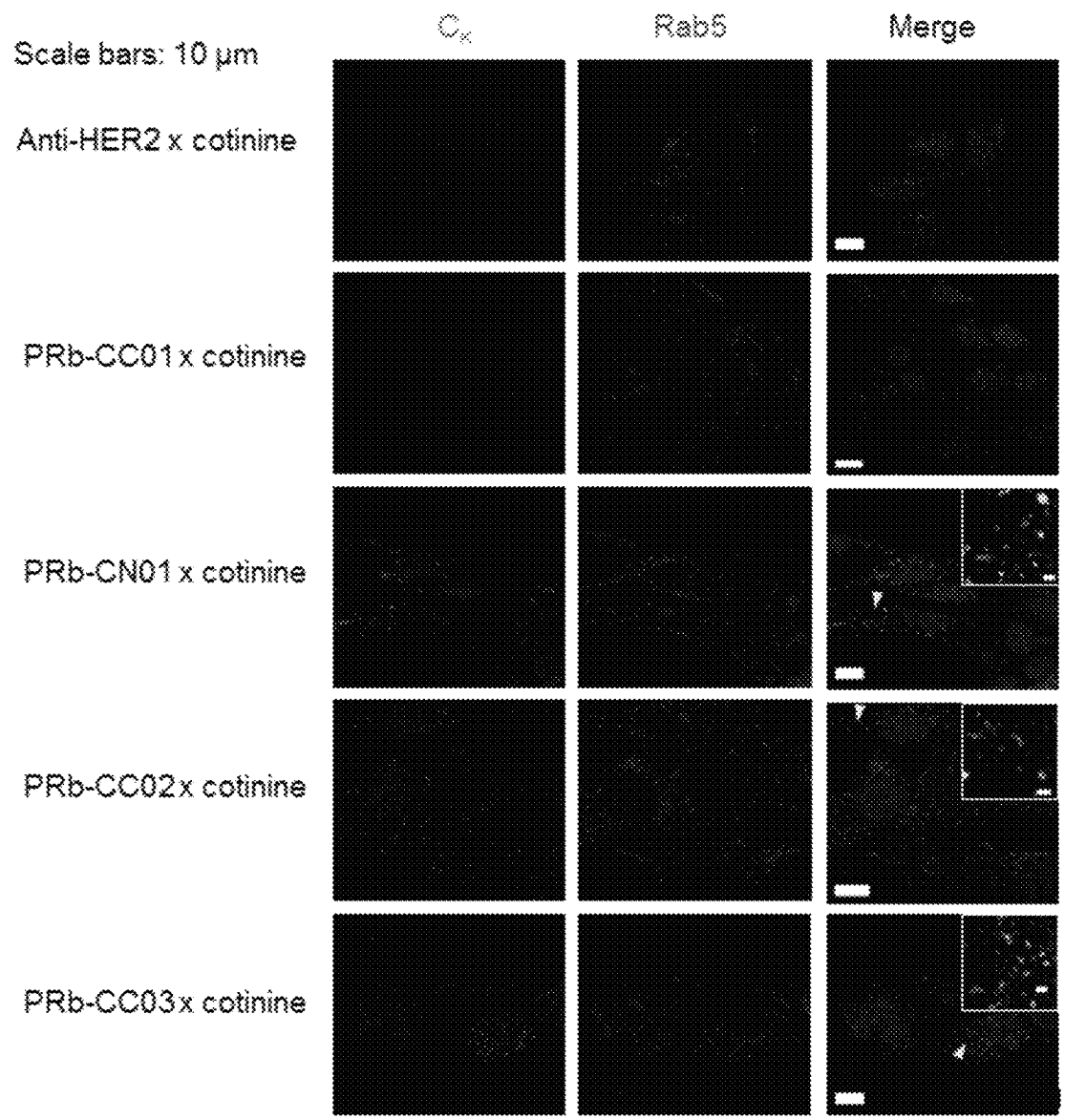

[Fig. 5a]
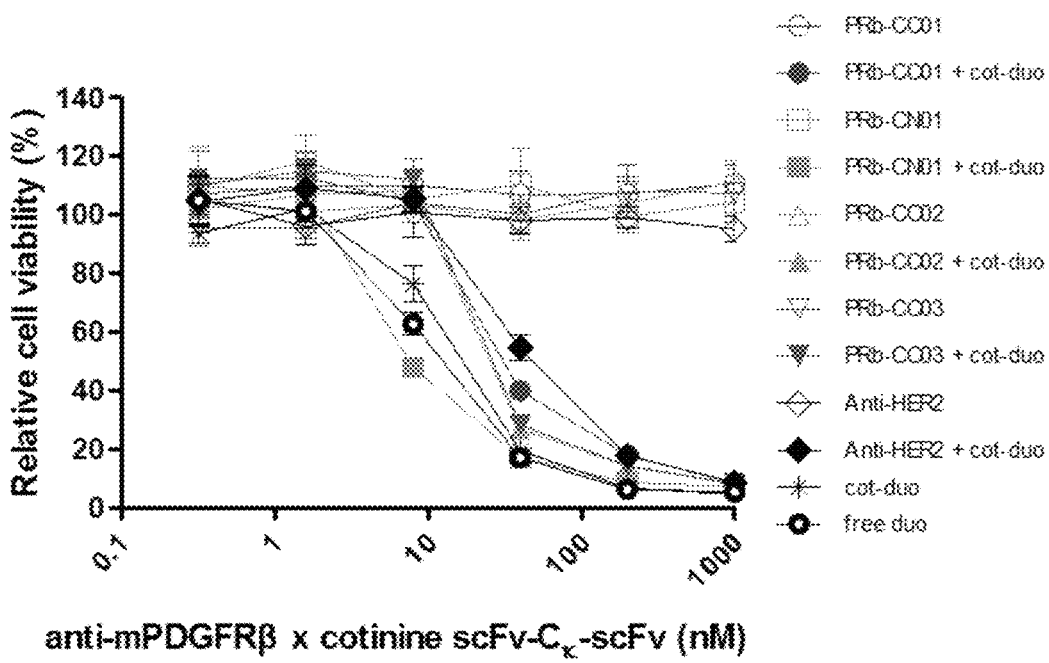
[Fig. 5b]
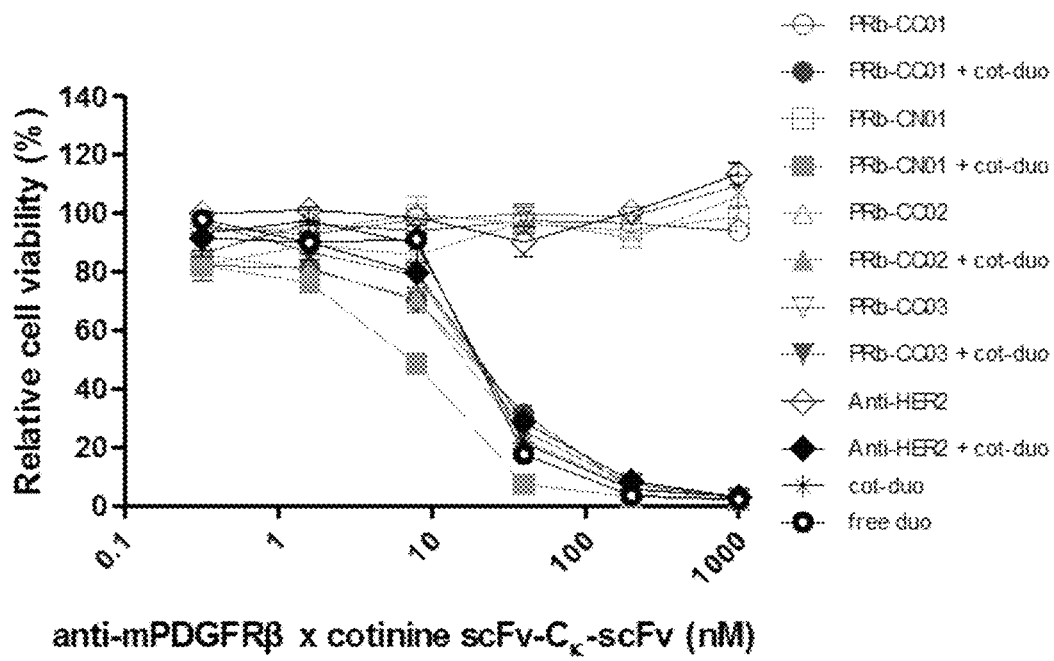

[Fig. 5c]
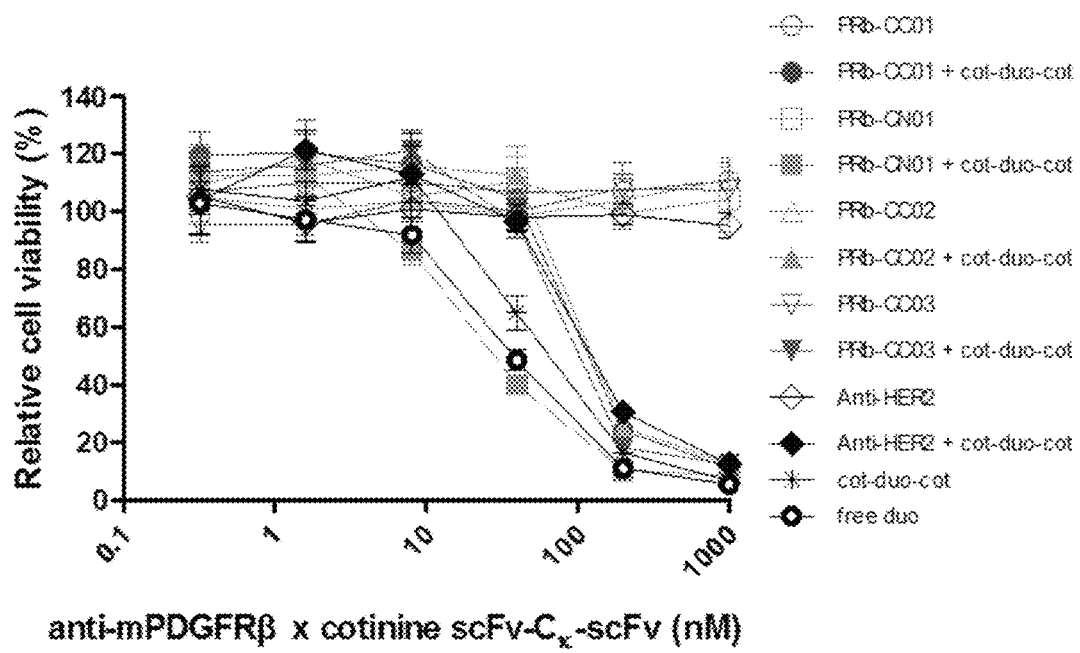
[Fig. 5d]
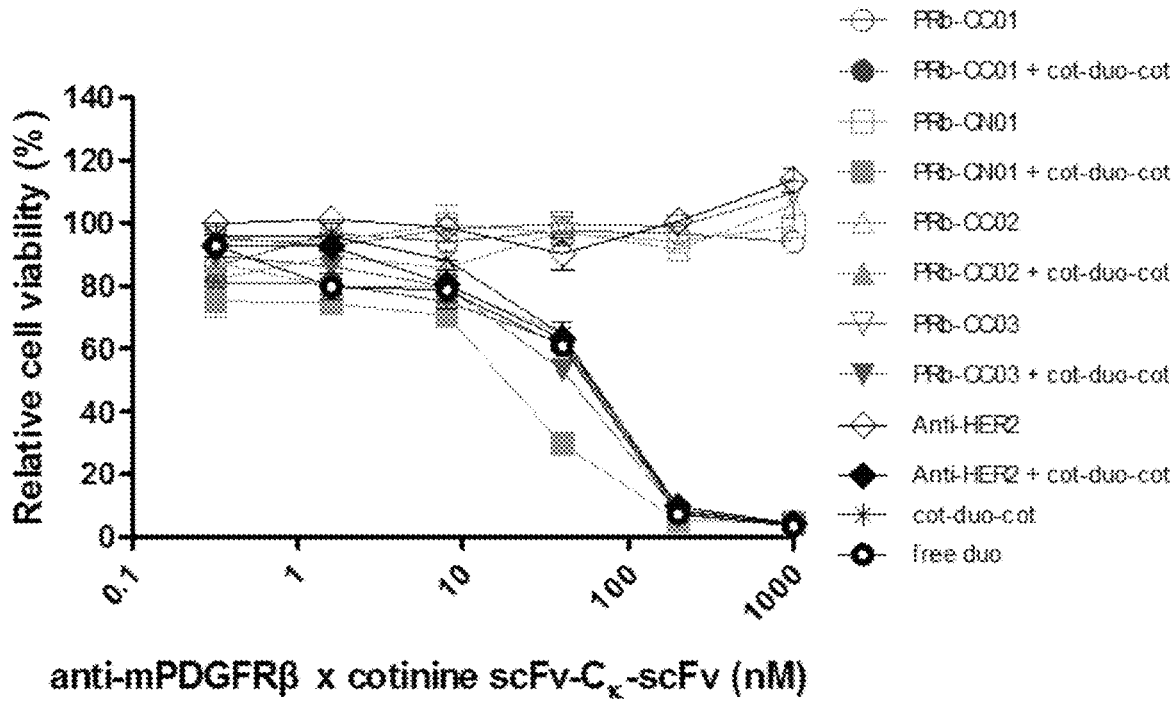

[Fig. 6]
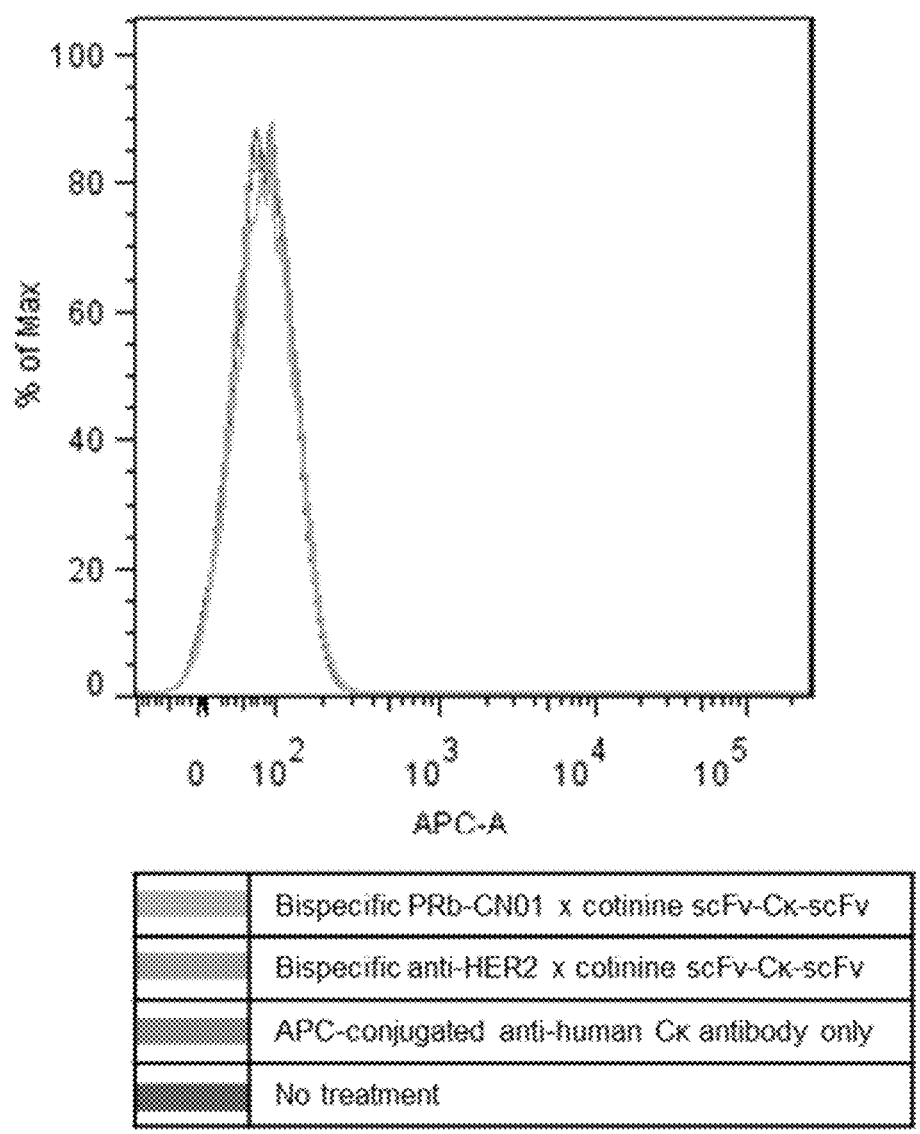

[Fig. 7]
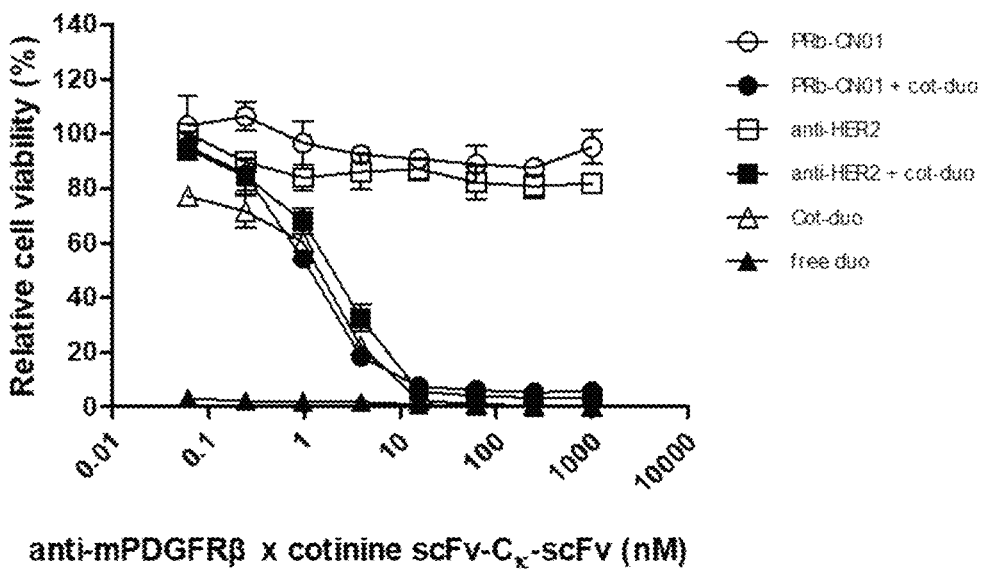
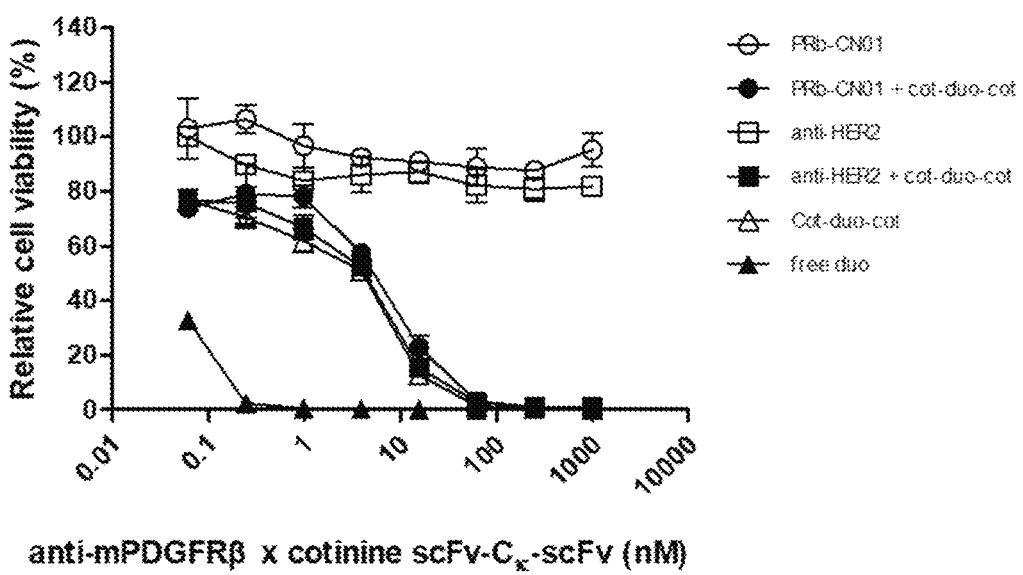

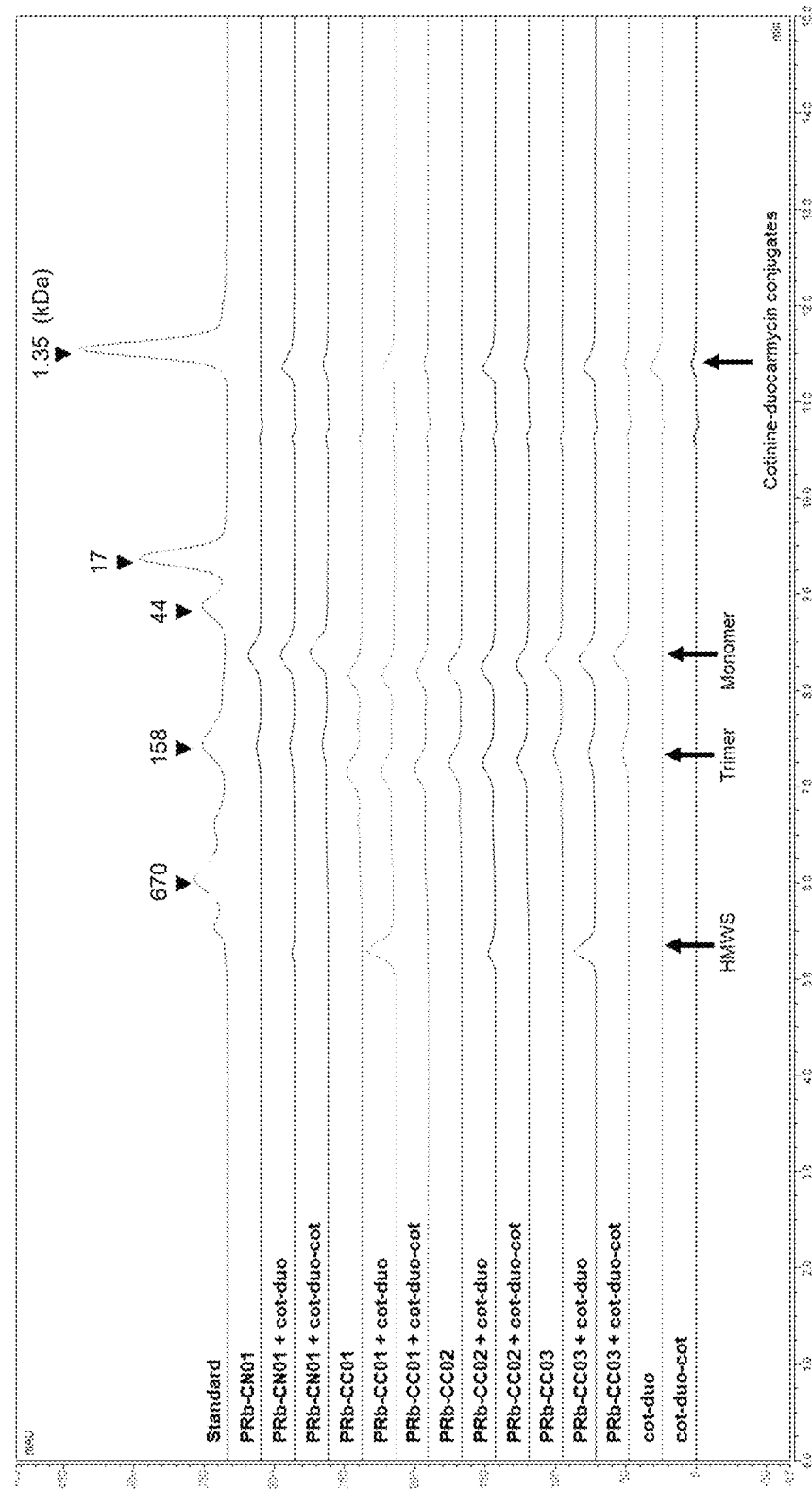
[Fig. 8]

[Fig. 9]
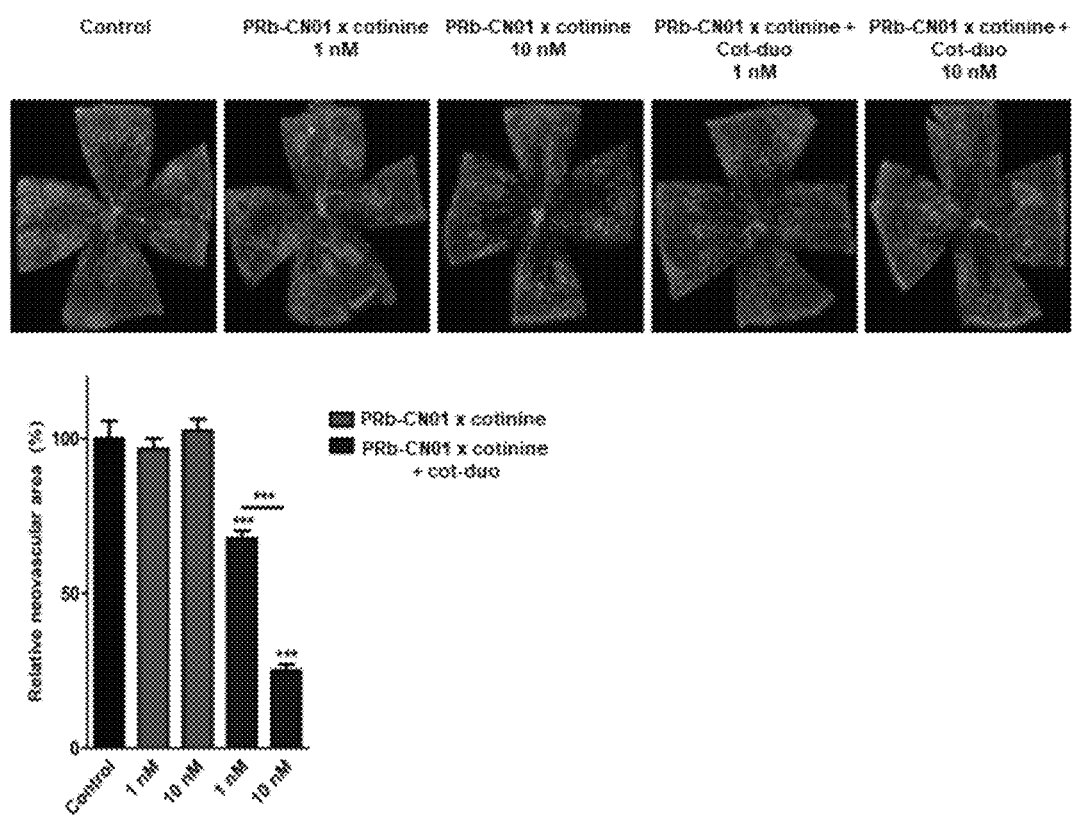

[Fig. 10]
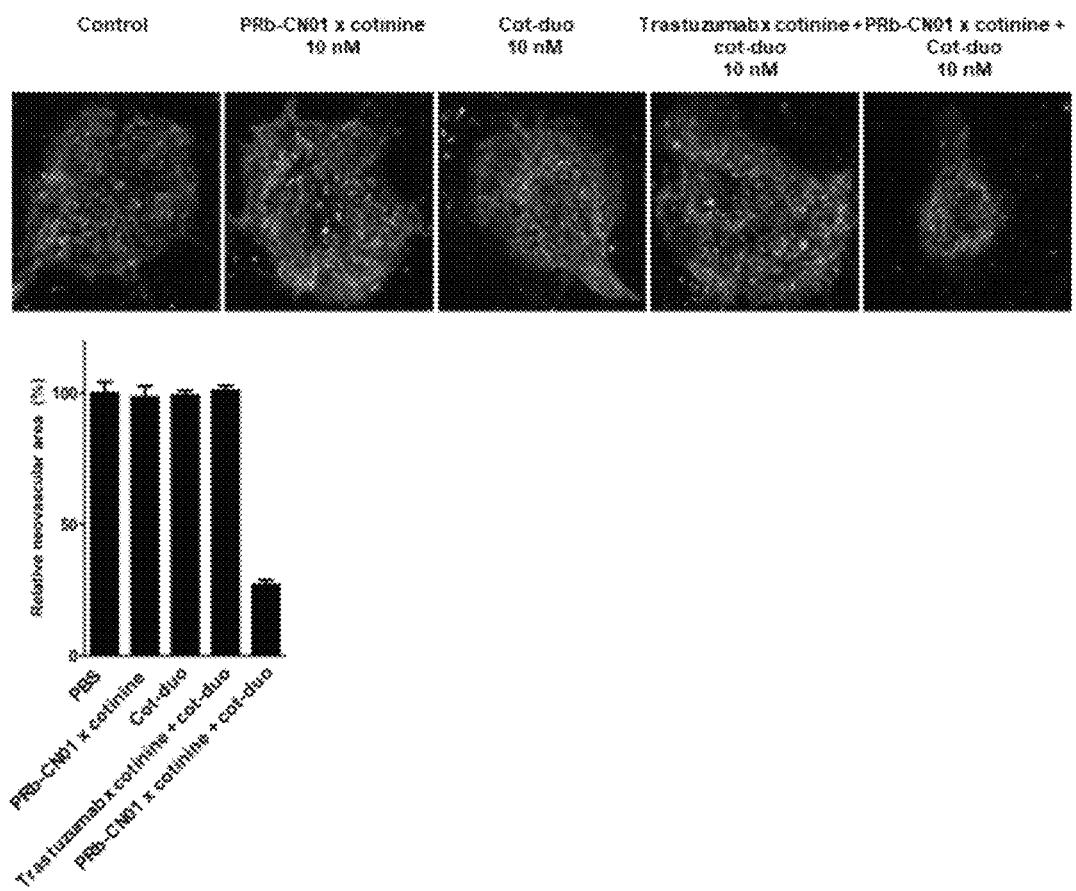

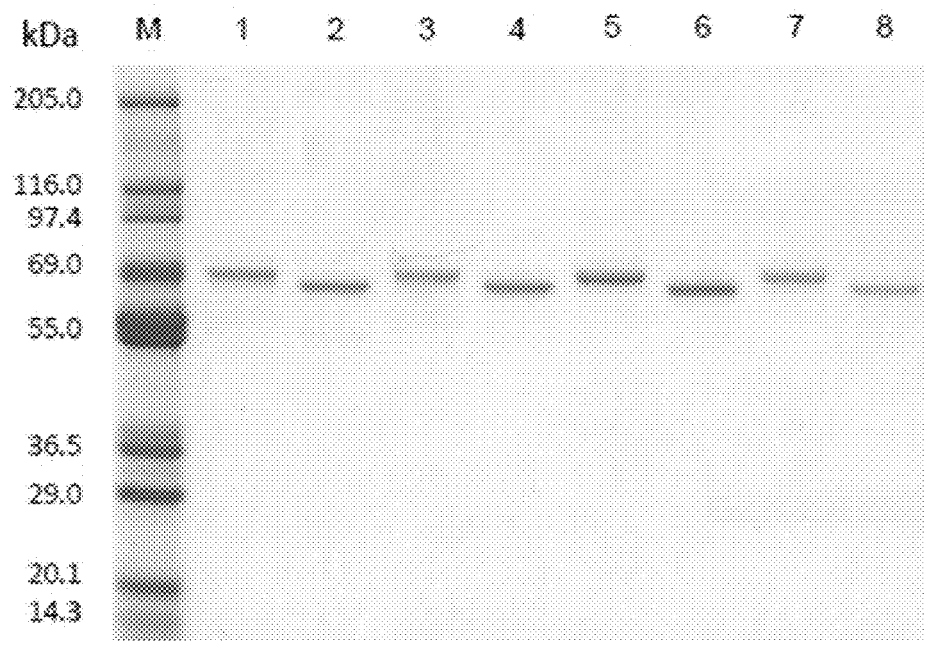
[Fig. 11]

[Fig. 12a]
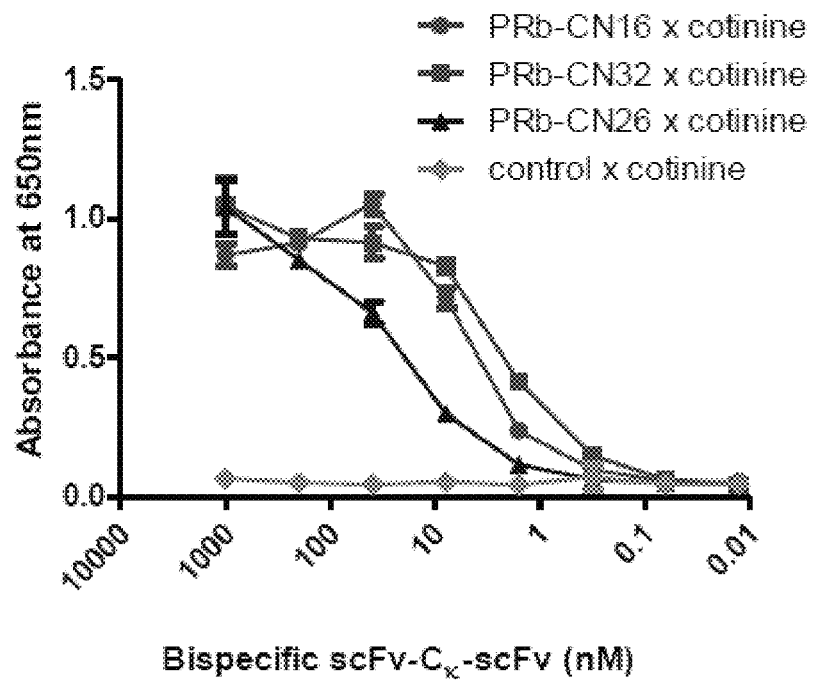
[Fig. 12b]
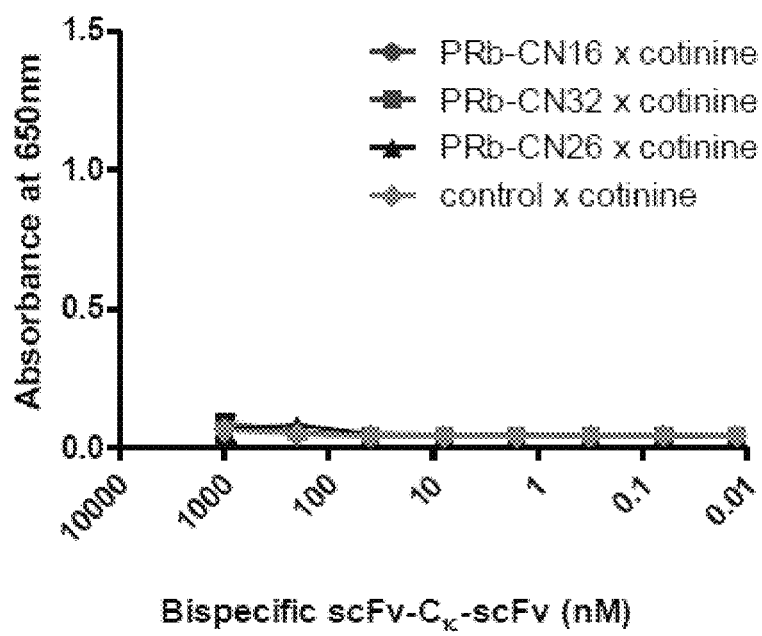

[Fig. 12c]
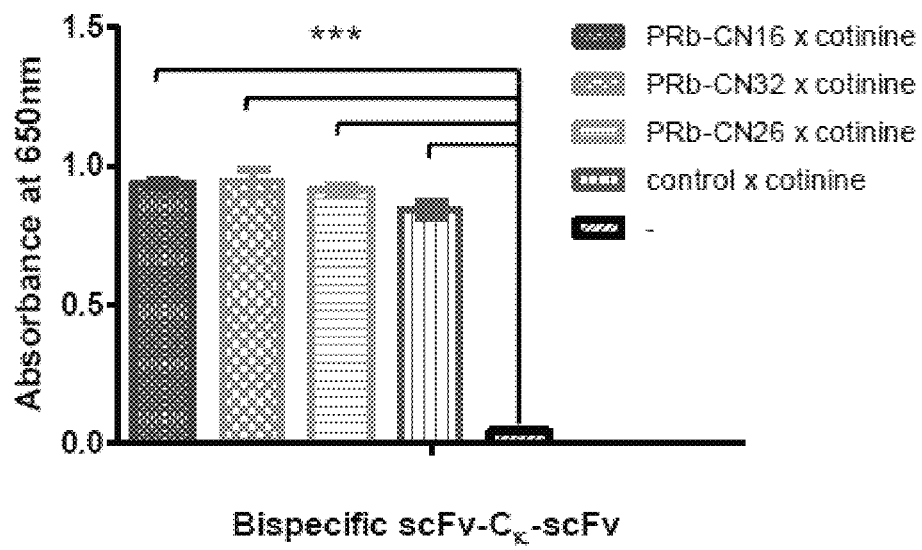
[Fig. 12d]
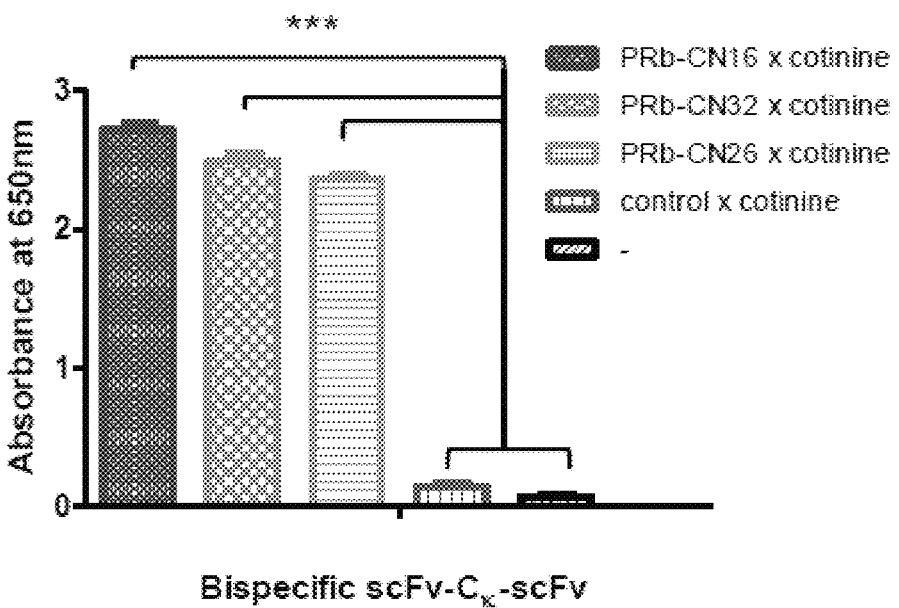

[Fig. 13a]
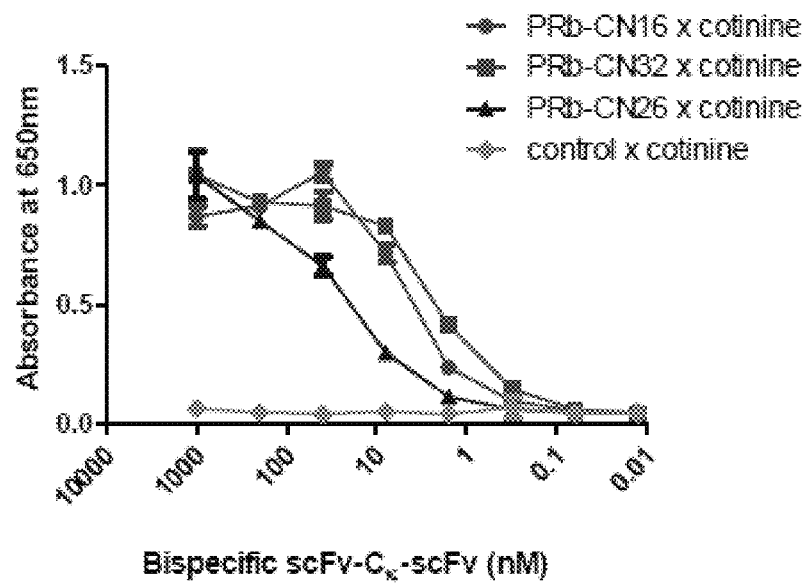
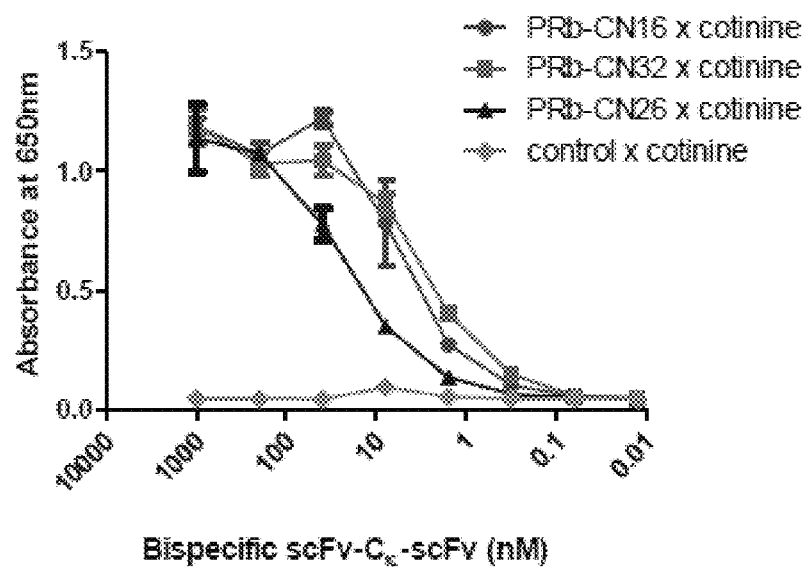

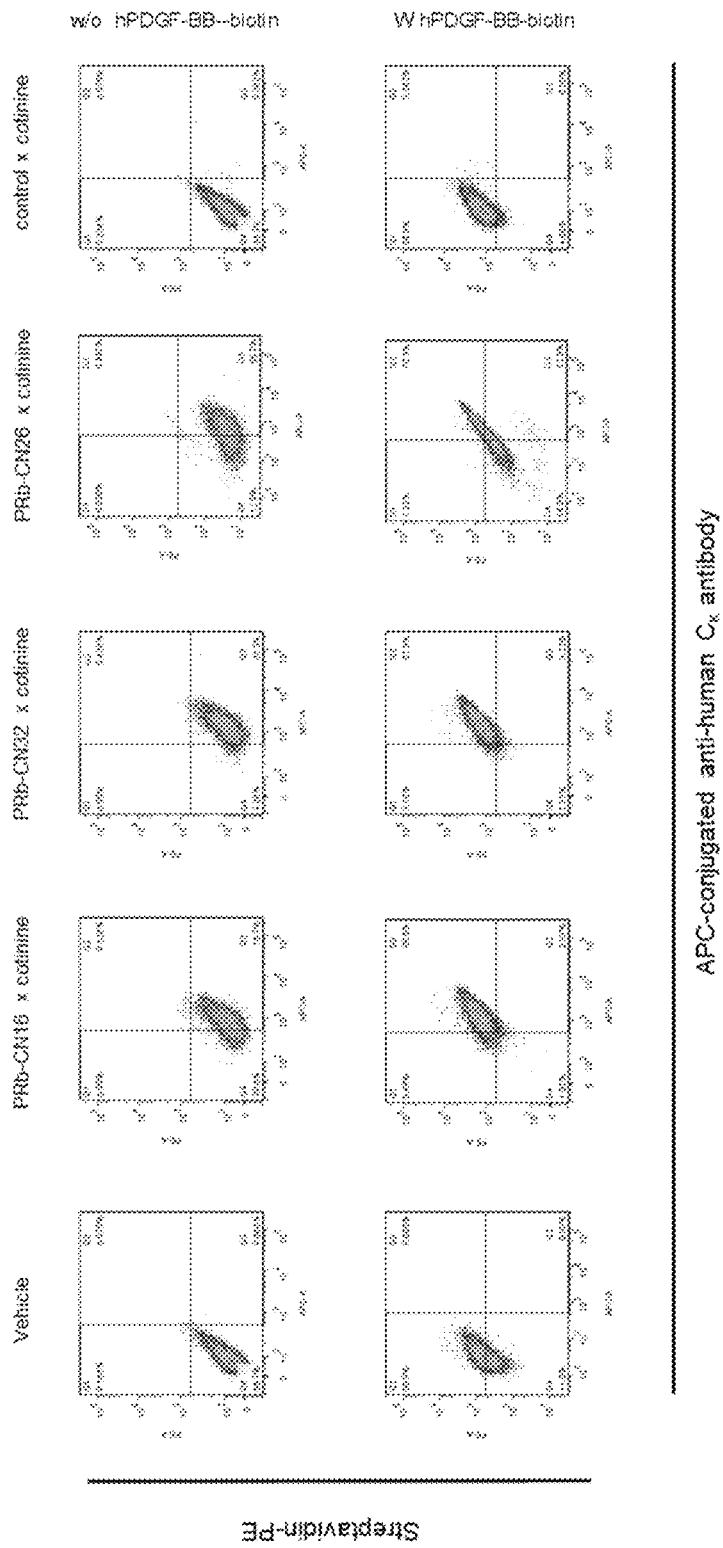
[Fig. 13b]

[Fig. 13c]
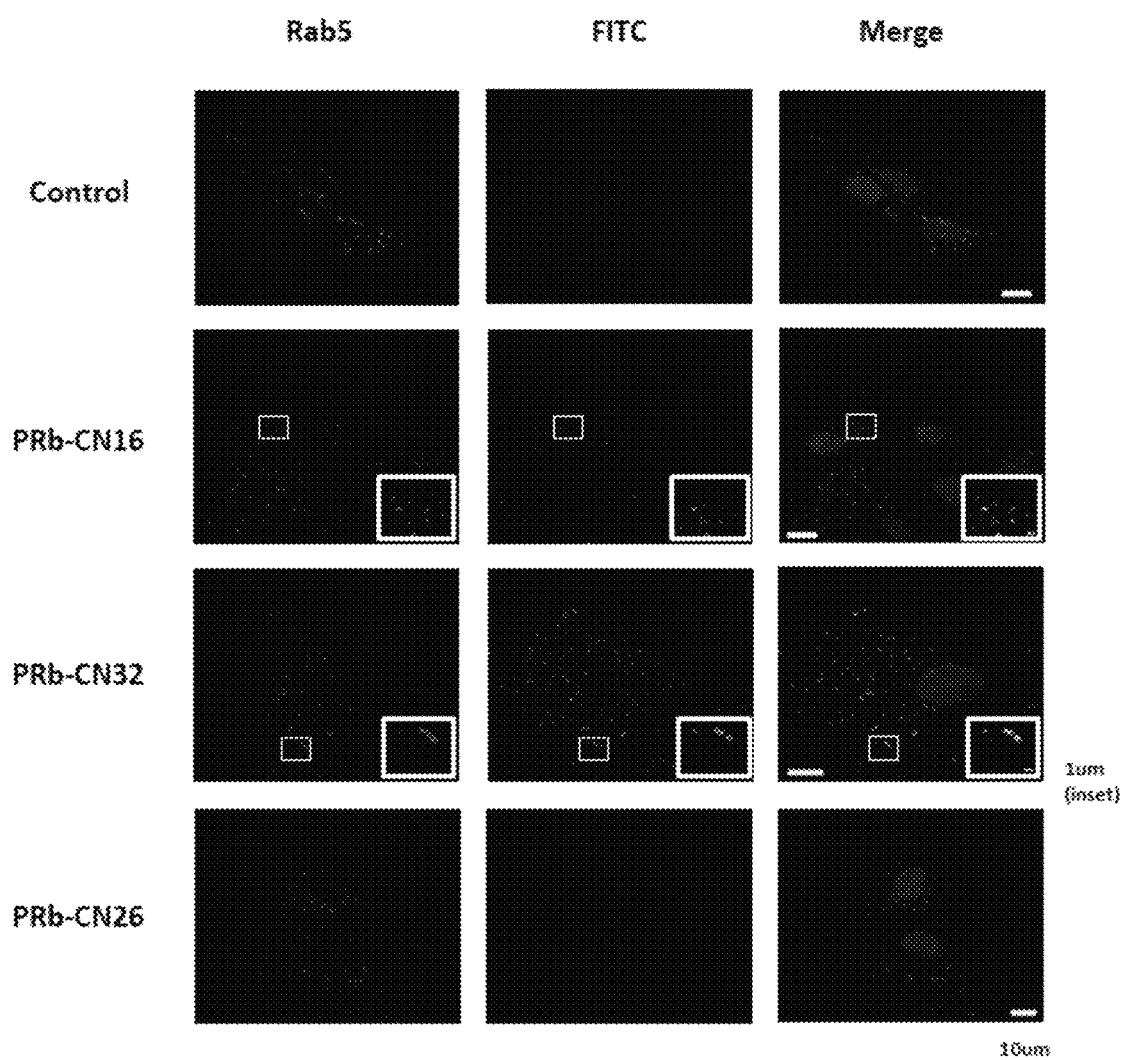

【Fig. 13d】
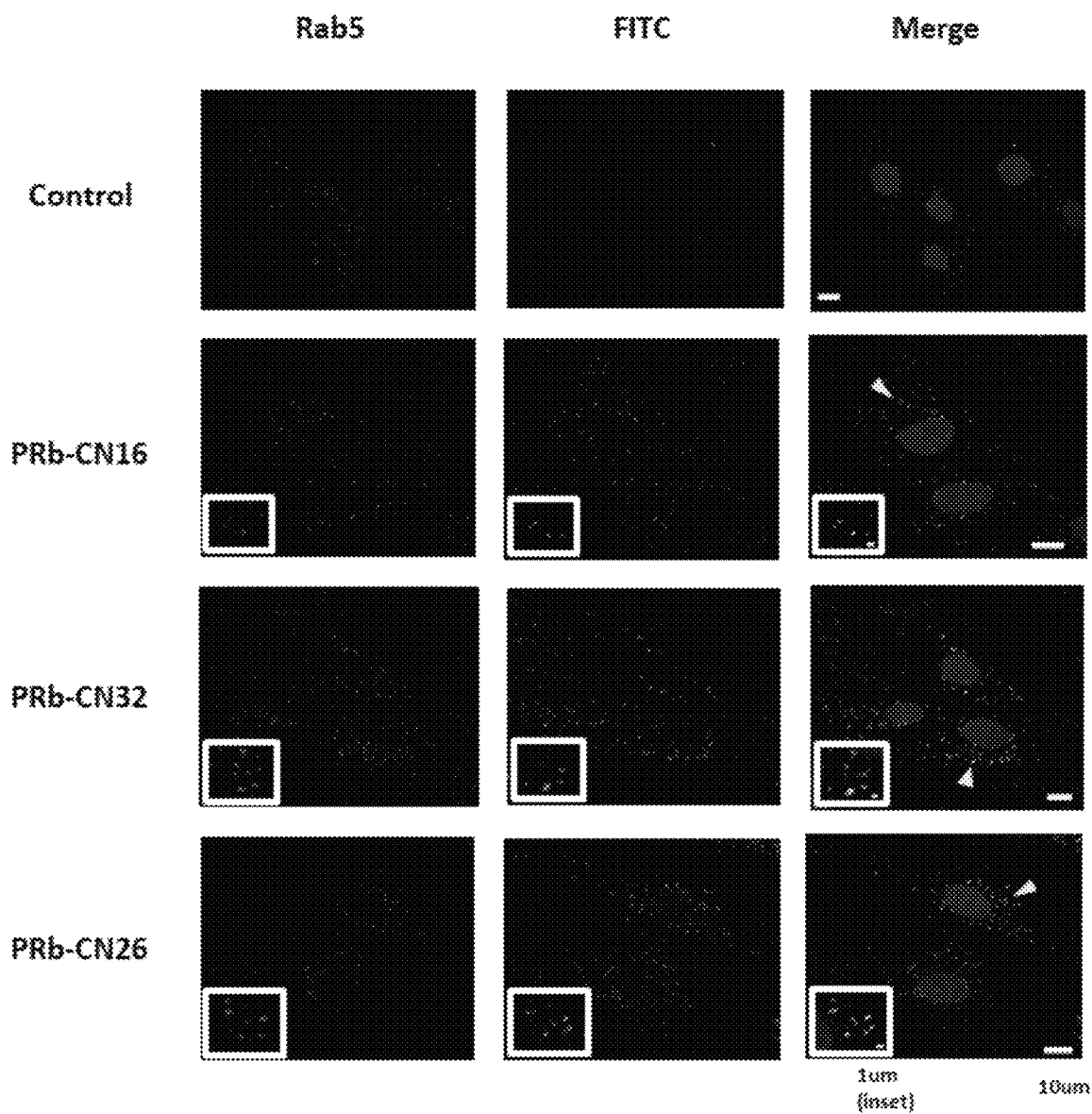

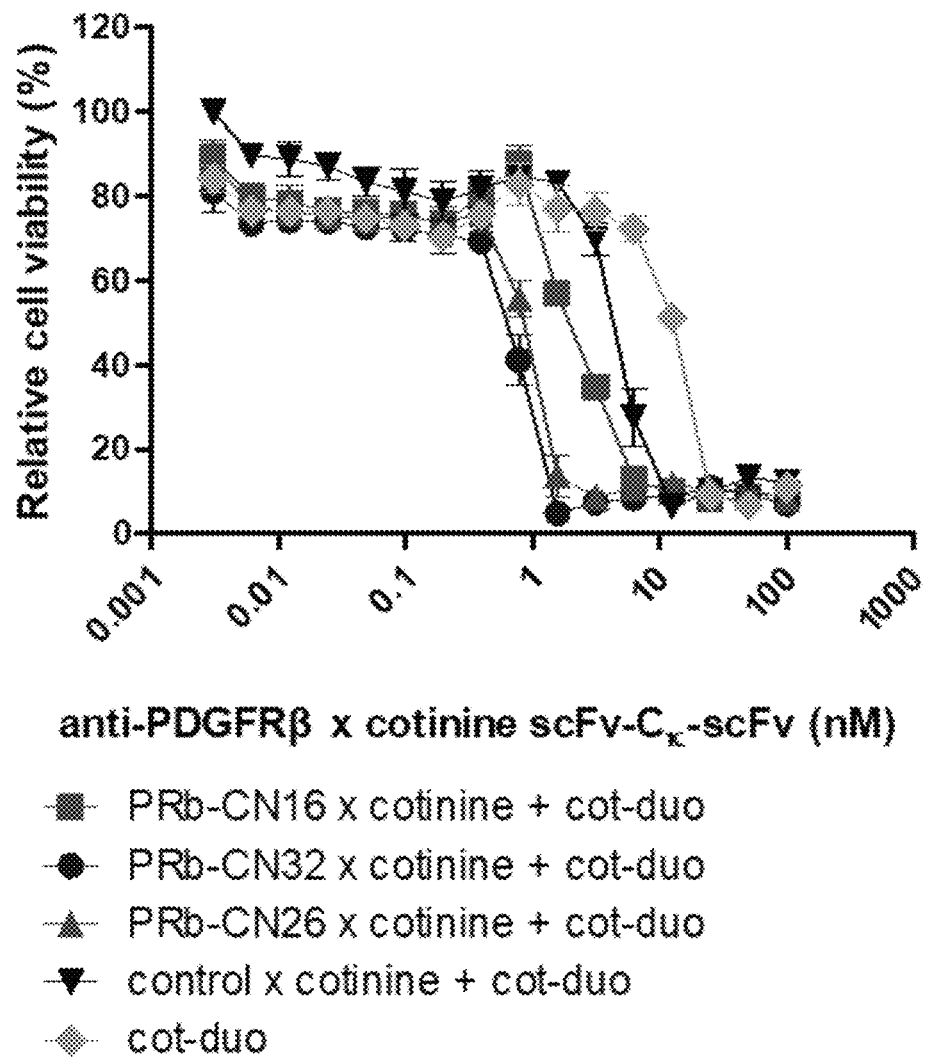
[Fig. 14a]

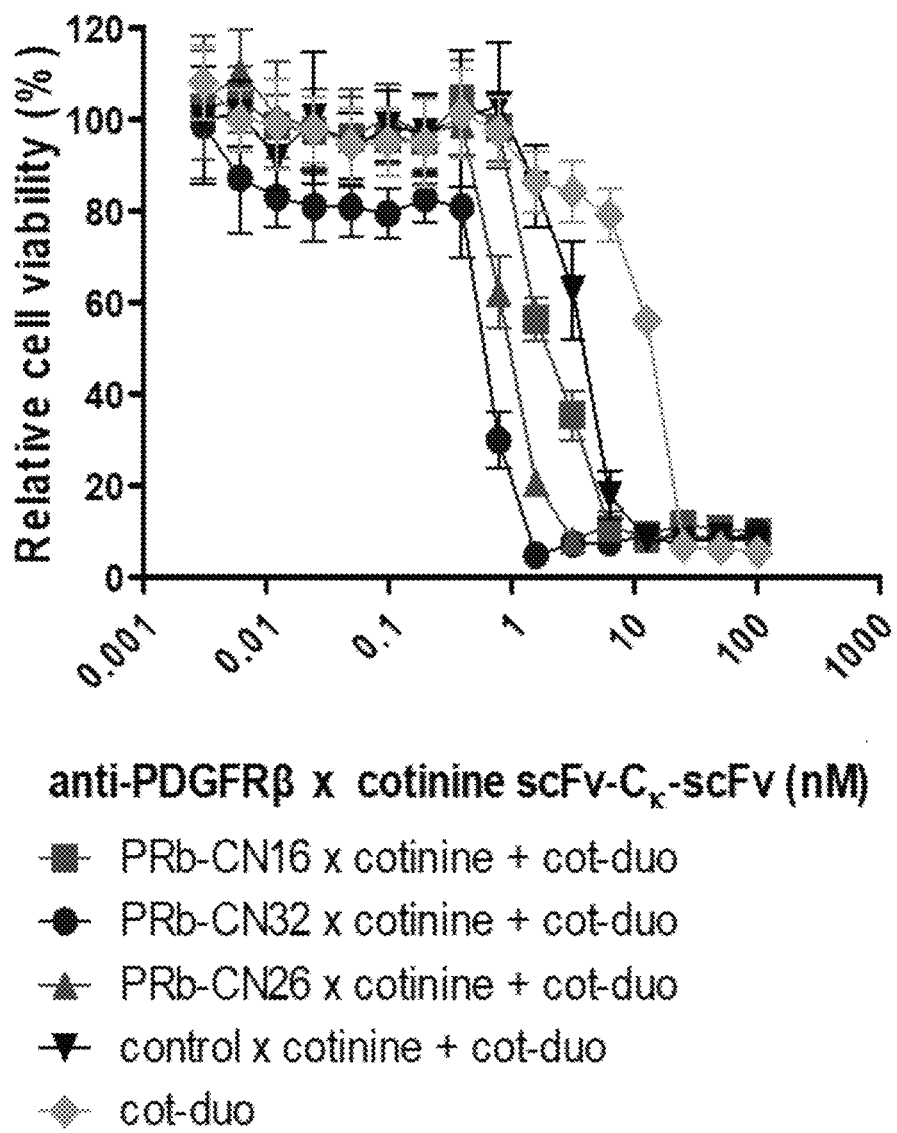
[Fig. 14b]

[Fig. 15]
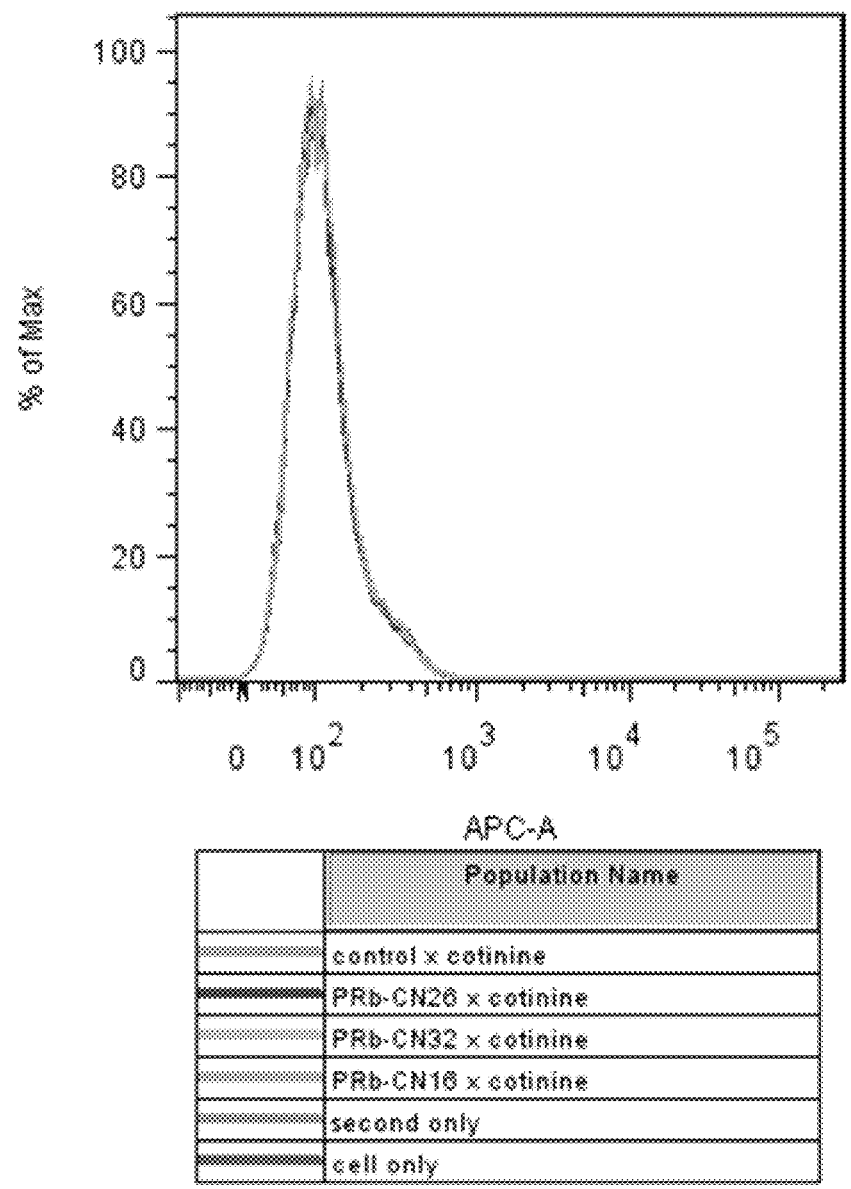

[Fig. 16]
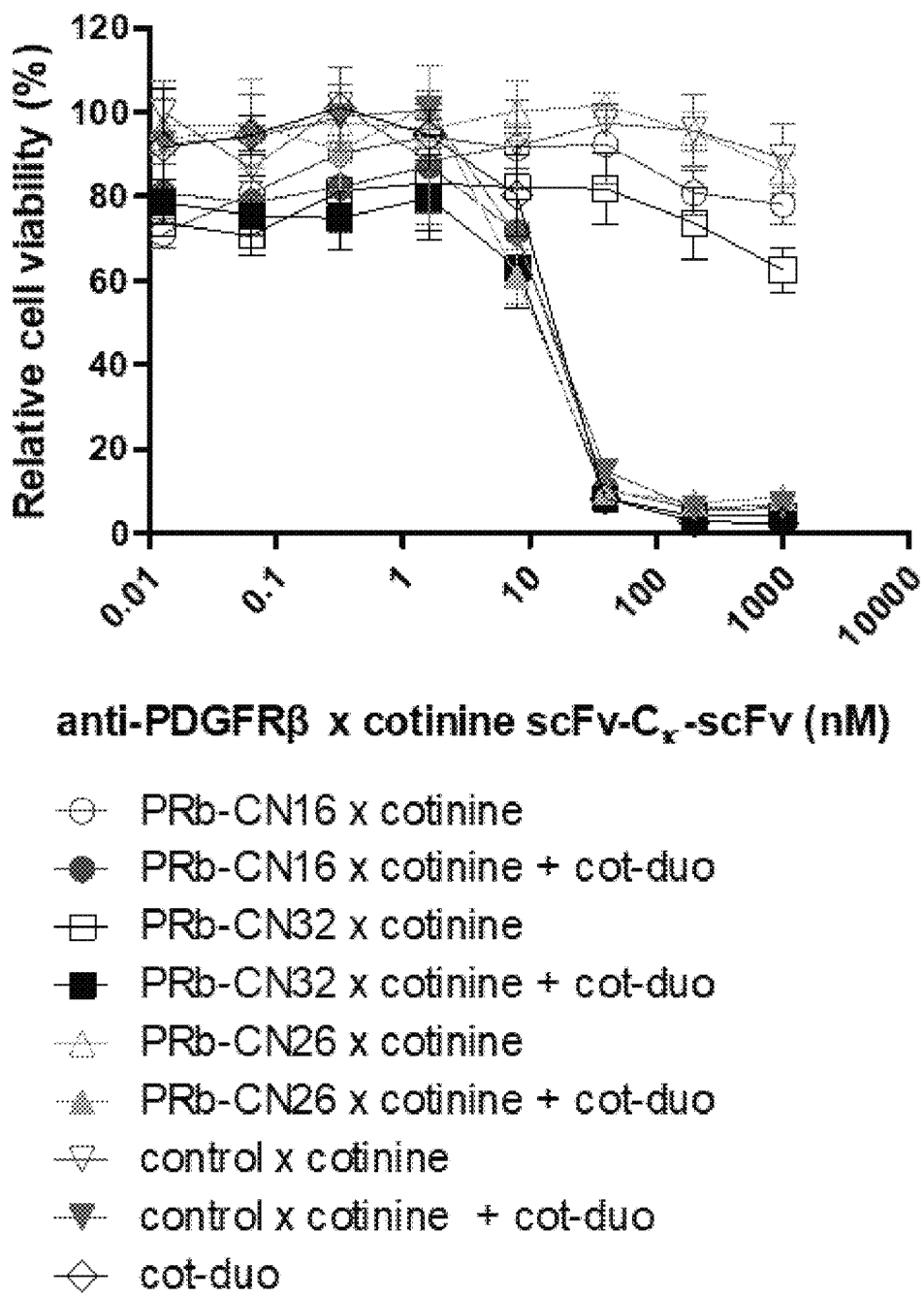

[Fig. 17]
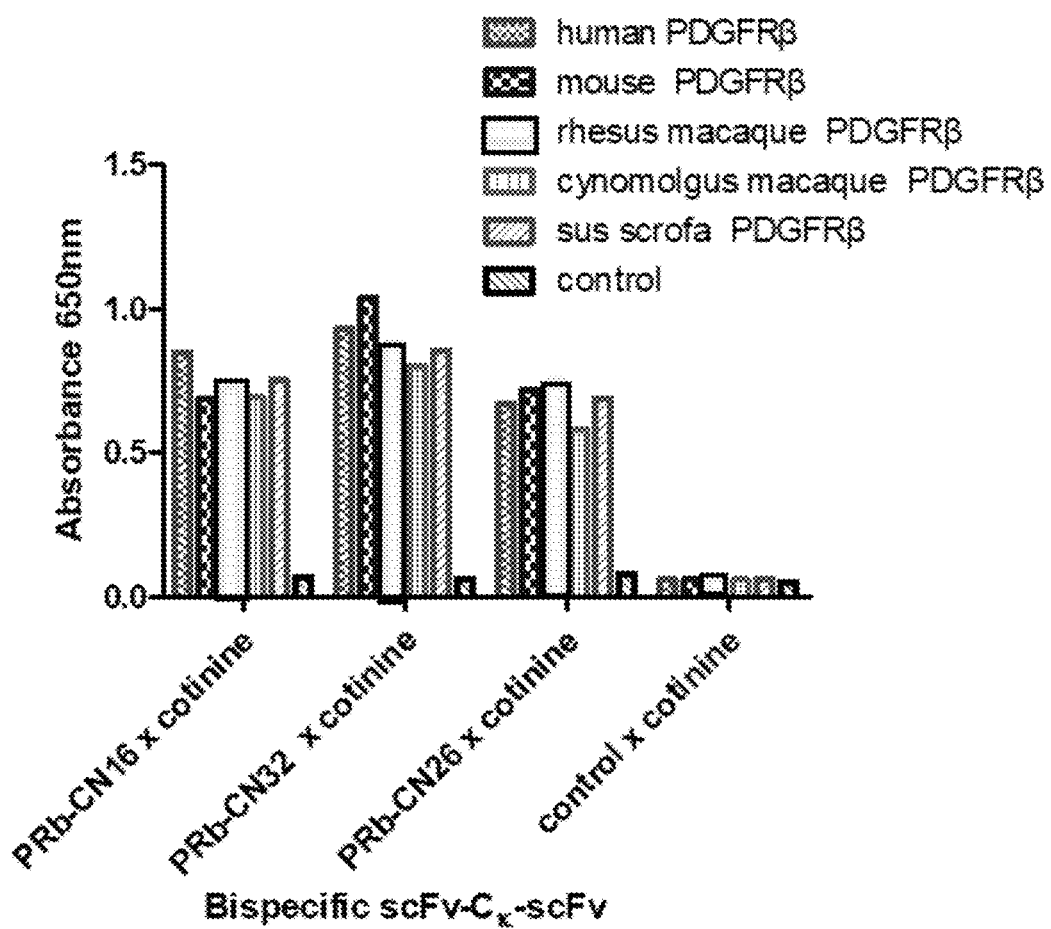

【Fig. 18】
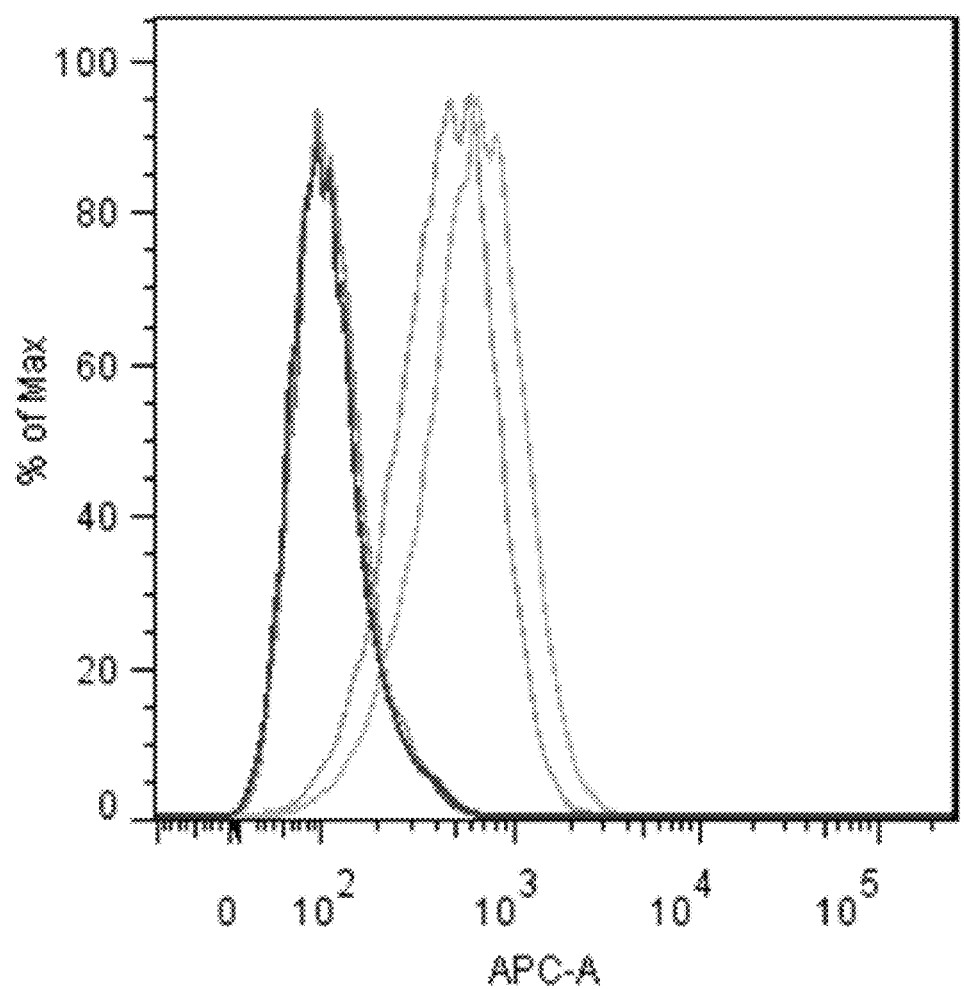

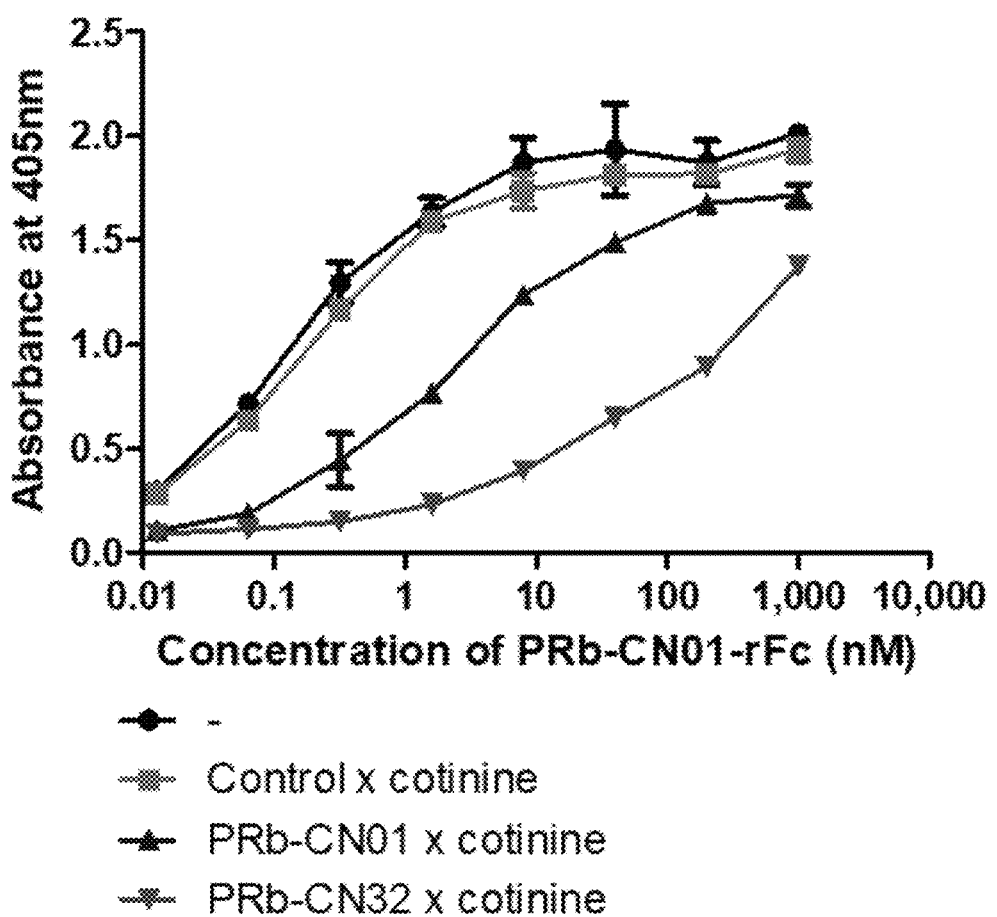
[Fig. 19a]

[Fig. 19b]
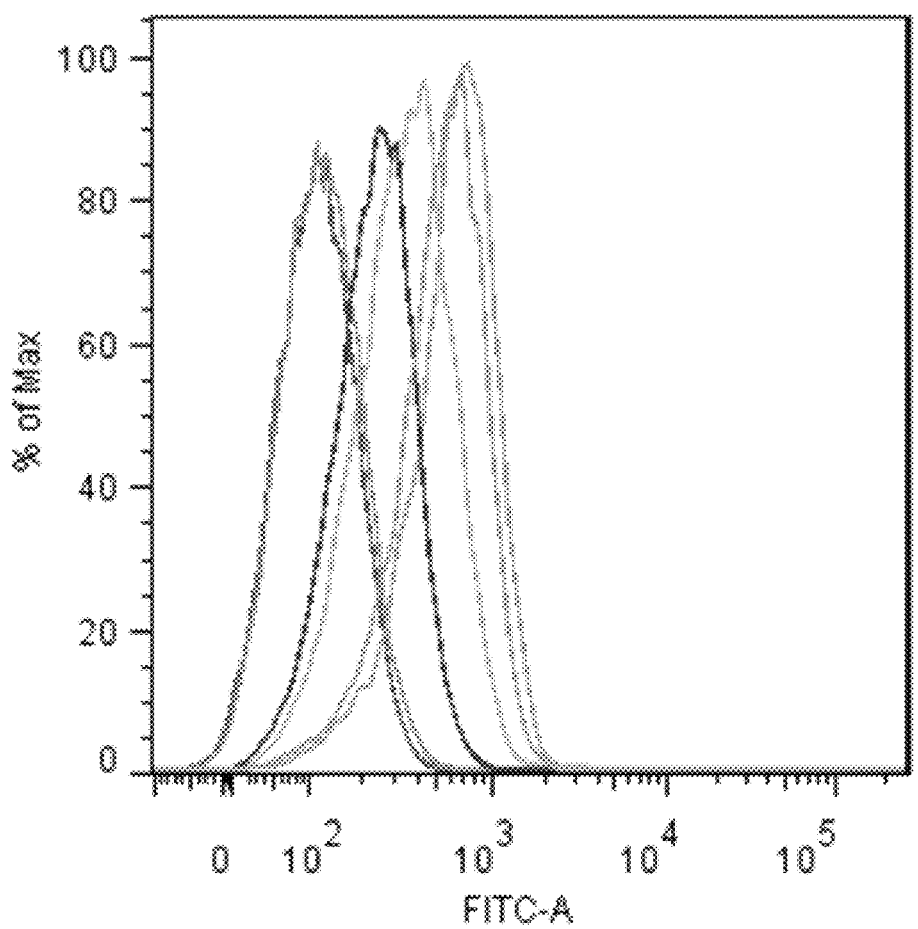

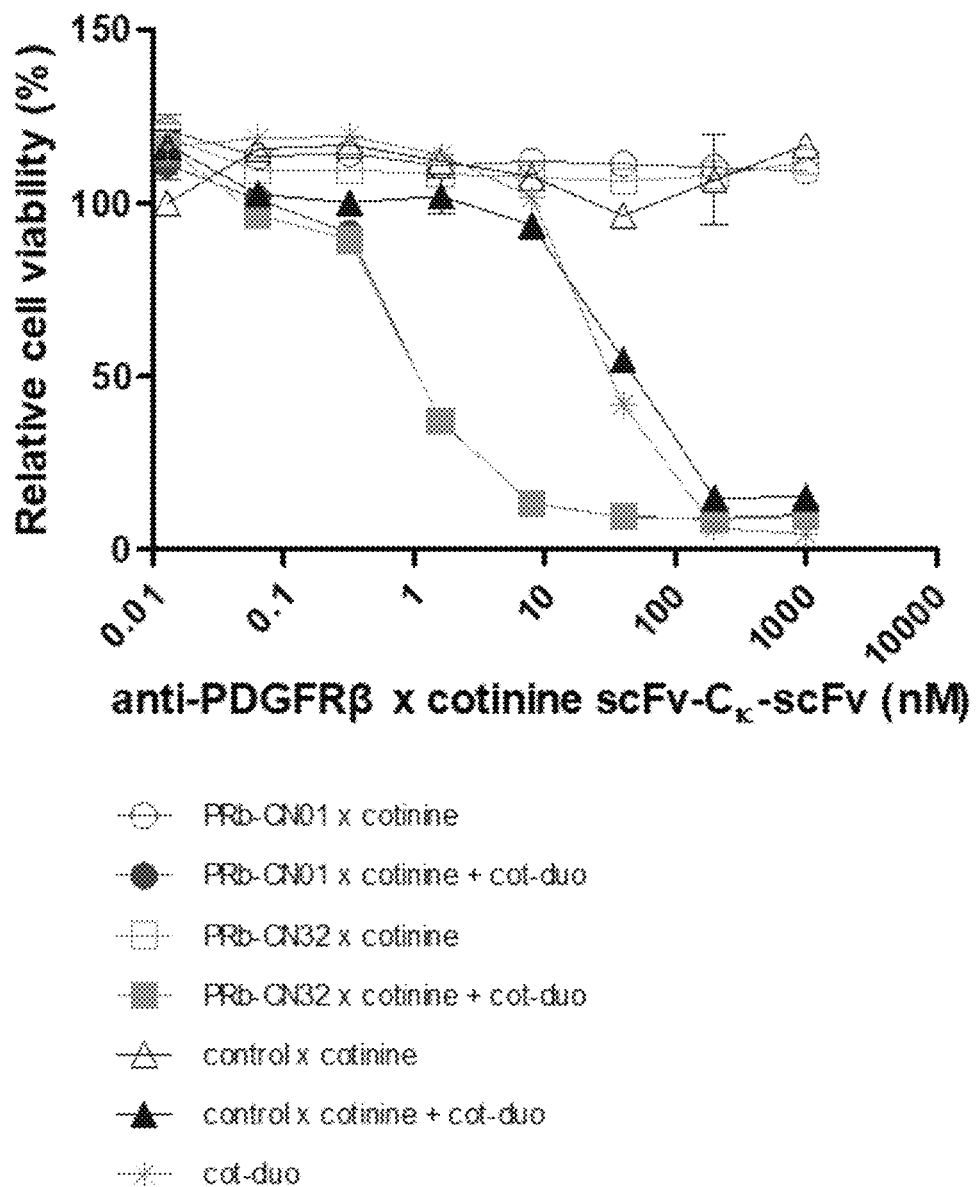

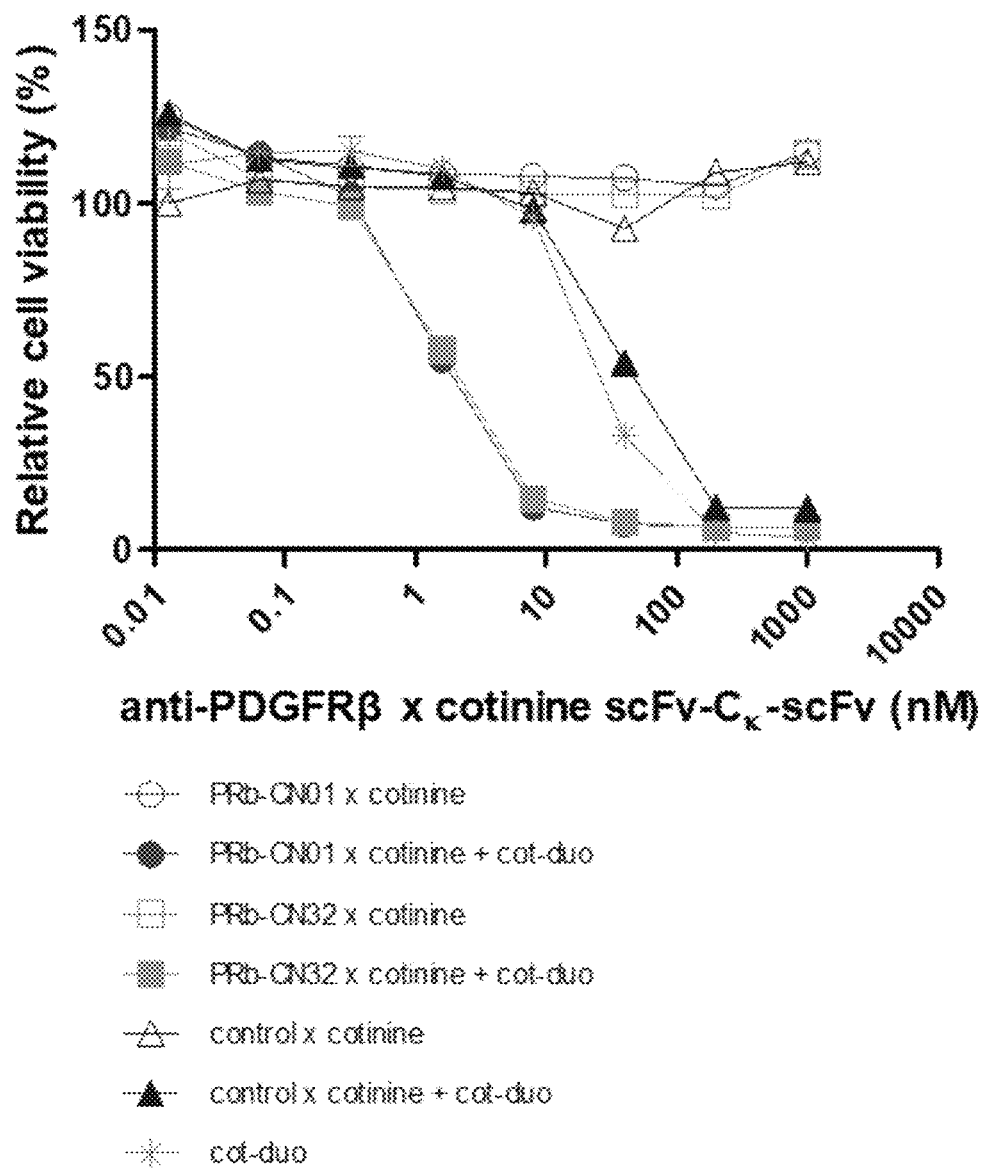
[Fig. 20b]

PDGF RECEPTOR ANTIBODY AND USE THEREOF

TECHNICAL FIELD

The present invention relates to an antibody against a PDGF receptor, an antibody-drug conjugate in which a chemotherapeutic agent is conjugated to the antibody against a PDGF receptor, and a prophylactic or therapeutic use for ocular neovascular diseases using the same.

RELATED ART

Angiogenesis, also called as neovascularization, involves the step of formation of protrusions from existing blood vessels and their infiltrating into surrounding tissues. Vasculogenesis, a process related to this, involves the differentiation of endothelial cells and hemangioblasts that already exist in the entire tissue, and then the formation of blood vessels as they connect together.

Angiogenesis occurs extensively during development, and also during wound healing to restore blood flow to tissues after injury or injury, even in a healthy body. However, angiogenesis is also associated with cancer and tumor formation.

Various ocular disorders involve alterations in angiogenesis. For example, diabetic retinopathy, one of the causes of blindness in adults, is associated with excessive angiogenesis. Non-proliferative retinopathy involves the selective loss of perivascular cells in the retina, and the associated capillaries expand and blood flow increases due to this loss. In the expanded capillary, endothelial cells proliferate and form cystic protrusions to become microaneurysms, and adjacent capillaries are blocked, so that perfusion does not occur in the retinal region around these microaneurysms. In fact, shunt blood vessels appear between adjacent regions of microaneurysms, and the clinical symptom of early diabetic retinopathy appears to have microaneurysms and non-perfused retinal regions. The leak occurs and capillaries can burst in microaneurysms, which can lead to effusion and bleeding. Proliferative diabetic retinopathy occurs when some areas of the retina continue to lose capillaries and become unperfused, resulting in new blood vessels appearing in discs and other areas on the retina. These new blood vessels easily grow into the vitreous and bleeding sites, causing preretinal hemorrhage. As proliferative diabetic retinopathy develops, excessive vitreous bleeding can fill most of the vitreous cavity. In addition, new blood vessels are accompanied by fibrous tissue proliferation that can cause traction retinal detachment.

Early treatment of macular edema and proliferative diabetic retinopathy prevents blindness for 5 years in 95% of patients, but delayed treatment prevents blindness in only 50% of patients. Therefore, early diagnosis and early treatment are essential.

Another ocular disorder accompanied with angiogenesis is senile macular degeneration (AMD). AMD is characterized by a series of pathological changes that occur in the macula of the central region of the retina, and is accompanied by vision problems that specifically affect central vision. The retinal pigment epithelium resides on Bruck's membrane, which is a basement membrane complex being thickened and hardened in AMD. New blood vessels can be formed as they pass through Bruch's membrane from the lower choroid which contains an abundant layer of blood vessels. These blood vessels can then leak fluid or cause bleeding between the retinal pigment epithelium and the sensory retina, as well as under the retinal pigment epithelium. Subsequent fibrous scar formation causes loss of central vision by blocking the nutrients supply to photoreceptor cells and killing these cells. This type of senile maculopathy is called "wet type", because of leaking blood vessels and subretinal edema or blood. "Dry type" of senile maculopathy involves the collapse of the retinal pigment epithelium with the loss of the photoreceptor cells located over the retinal pigment epithelium. This dry type degrades vision.

Among these angiogenesis regulators, the role of PDGF-B members belonging to the PDGF family of signaling molecules is being studied, because they are believed to play a certain role in the formation, proliferation and proper functioning of parietal cells such as perivascular cells which are called as vascular smooth muscle or intervascular cells.

The PDGF family consists of the monomers of PDGF-A, PDGF-B, PDGF-C and PDGF-D and the dimers of PDGF-AA, PDGF-AB, PDGF-BB, PDGF-CC, and PDGF-DD. Upon binding of the PDGF dimer, PDGF binds to the PDGF receptors $\alpha$ and $\beta$. The PDGF receptor is a kind of tyrosine kinase enzyme, and can form a three combination of $\alpha\alpha$, $\beta\beta$ and $\alpha\beta$ dimers. The extracellular region of the PDGF receptor is composed of five immunoglobulin-like regions, and the intracellular region contains a tyrosine phosphorylation region. The ligand binding site of the PDGF receptor is located in the first three immunoglobulin-like regions. PDGF binds to the immunoglobulin-like domains 2 and 3 of the PDGF receptor to induce dimerization of the receptor, and induces the direct receptor-receptor interactions including immunoglobulin-like domains 4 and 5 for further stabilization.

PDGF-CC specifically interacts with PDGF receptor-$\alpha\alpha$ and PDGF receptor-$\alpha\beta$, but does not interact with PDGFR-$\beta\beta$. Thus, it is similar to PDGF-AB. PDGF-DD is considered as being specific for PDGFR-$\beta\beta$, because it binds to PDGFR-$\beta\beta$ with high affinity and to PDGF receptor-$\alpha\beta$ with much lower degree. PDGF-AA only binds to the PDGF receptor-$\alpha\alpha$. PDGF-BB uniquely binds all three combinations of receptors with high affinity.

Excessive signaling between PDGF and PDGF receptor plays an important role in many cancers such as renal cell carcinoma, lung cancer, glioblastoma, chronic lymphocytic leukemia, and prostate cancer. The PDGF receptor promotes tumor growth by promoting tumor persistence by directly affecting tumor growth related blood vessels, stromal fibroblasts (somatic fibroblasts) and the like.

As a monoclonal antibody targeting the signaling of PDGF and PDGF receptor, Olaratumab (IMC-3G3, Lartruvo™) is a recombinant human IgG1 antibody against PDGFR-$\alpha$ that specifically binds to PDGF receptor $\alpha$, blocks the binding of PDGF-AA, PDGF-BB and PDGF-CC and activation of the receptor, and dose not cross-react with PDGFR-$\beta$. Olaratumab was first approved for cancer treatment in the U.S.A. in October 2016, based on the results of a stage Ib/II studies of late soft tissue sarcoma that showed that the combination of Olaratumab and doxorubicin significantly improved overall mean survival compared to doxorubicin alone.

Antibody-drug conjugates (ADCs) are therapeutic agents containing cytotoxic drugs-monoclonal antibodies, and delivering a toxic agent to cancer cells expressing target antigens with minimizing off-target toxicity.

In order to develop an optimized antibody-drug conjugate, there are complicated considerations such as antibody, linker, binding site, tumor type, antigen expression rate, toxin, drug to antibody ratio (DAR) and the like. For example, the binding site affects the binding rate, affinity, and stability. Because drug-conjugates internalize into cells and release drugs, toxic effects are important in how effectively they deliver drugs into cells. In addition, the internalization efficiency is different between antibodies that attach to the same target antigen located on the cell surface. Thus, the selection of an antibody internalizing efficiently is very important to the efficacy of the antibody-drug complex. Because there are many factors, such as the recycling of the antibody-drug conjugate to the target antigen, and intracellular trafficking affecting the cytotoxic effect of drugs, the method of accurately measures the toxicity rate of internalized antibodies can be checked after making the antibody-drug conjugate. Unfortunately, a lot of effort and time has been spent making candidates of antibody-drug conjugates using different types of antibodies.

Currently available PDGFR-β therapeutic agents focus on the antagonistic effect of PDGF ligand and cannot provide an efficient internalization of PDGFR-β. Accordingly, there is a need to develop an antibody that can efficiently internalize PDGFR-β to deliver an antibody or antibody-drug conjugate into cells expressing PDGFR-β.

DISCLOSURE

Technical Problem

An embodiment of the present invention relates to an anti-PDGF receptor antibody or an antibody or its antigen-binding fragment that recognizes PDGF receptor, specifically PDGF receptor-β.

A further embodiment of the present invention relates to an antibody-drug conjugate in which a drug is conjugated to the anti-PDGF receptor antibody or antigen-binding fragment of the antibody. The antibody-drug conjugate may be a conjugate in which a drug is bound to an anti-PDGF receptor antibody through a non-covalent bond or a covalent bond.

Another embodiment of the present invention is a bispecific antibody comprising the anti-PDGF receptor antibody or antigen-binding fragment thereof, and an antibody or antigen-binding fragment thereof specifically recognizing a hapten capable of conjugating with a drug.

The antigen-binding fragment of the antibody refers to a fragment of the antibody having at least one CDR, and may be scFv, (scFv)$_2$, scFv-Fc, Fab, Fab' or F(ab')$_2$.

An embodiment of the present invention relates to a use of a drug delivery system for delivering a drug to cells or tissues expressing a PDGF receptor, specifically PDGF receptor-β on the cell surface, and comprising an anti-PDGF receptor antibody. The drug delivery system may be a bispecific antibody comprising an anti-PDGF receptor antibody or antigen-binding fragment thereof and an antibody or antigen-binding fragment thereof against hapten for a chemotherapeutic drug. When the drug delivery system includes the antibody or antigen-binding fragment thereof recognizing hapten, the drug may be connected to hapten which is connected to the anti-PDGF receptor antibody or an antigen binding fragment thereof, and be delivered to target cells or tissues. The drug delivered to the target cells may be a drug for preventing, ameliorating or treating diseases associated with PDGF or PDGF receptor such as neovascular disease. The drug may be an immunotherapeutic agent or a chemotherapeutic agent, and the immunotherapeutic agent may be an antibody.

An embodiment of the present invention relates to a pharmaceutical composition for preventing, ameliorating or treating neovascular diseases, comprising an antibody-drug conjugate in which a drug is conjugated to the anti-PDGF receptor antibody or antigen-binding fragment thereof, or an antibody-drug conjugate in which a drug is conjugated via hapten to the anti-PDGF receptor antibody or antigen-binding fragment thereof.

An embodiment of the present invention is a method of treating a subject diagnosed as suffering from a neovascular disease or having a risk of occurrence of a neovascular disease, comprising administering an antibody-drug conjugate in which a drug is conjugated to the anti-PDGF receptor antibody or antigen-binding fragment thereof, or an antibody-drug conjugate in which a drug is conjugated via hapten to the anti-PDGF receptor antibody or antigen-binding fragment thereof, to the subject at a sufficient amount of preventing, improving or treating the diseases in the subject as a first therapeutic agent or an auxiliary therapeutic agent.

Technical Solution

Hereinafter, the present invention will be described in more detail.

An embodiment of the present invention relates to an antibody or antigen-binding fragment of an antibody that specifically recognizes a PDGF receptor, specifically, PDGF receptor-β (PDGFR-β).

"Antibody" as used in the present disclosure is a substance produced through antigen stimulation. Examples of antibodies include, but are not limited to, animal antibodies, chimeric antibodies, humanized antibodies, and the like.

In addition, the isolated antigen-binding fragment is also within the scope of the antibody of the present invention. The complementary-determining region (CDR) refers to a variable region of an antibody that is important for antigen specificity. The antigen-binding fragment described above refers to a fragment of an antibody having at least one CDR, which may be scFv, (scFv)$_2$, scFv-Fc, Fab, Fab' and F(ab')$_2$, or preferably scFv. The antibody may be a polyclonal antibody or a monoclonal antibody. The antibody may be selected from immunoglobulins of all subtypes (e.g., IgA, IgD, IgE, IgG (IgG1, IgG2, IgG3, IgG4), IgM, etc.). The IgG type antibody may be an IgG1, IgG2, IgG3, or IgG4 subtype, such as an IgG1 or IgG2 subtype.

As used in the present invention, the "antigen-binding fragment" of the chain (heavy chain or light chain) of an antibody or immunoglobulin is devoid of some amino acids compared to the full-length chain, but contains a portion of an antibody capable of specifically binding to an antigen. These antigen-binding fragments can be biologically active in that they can specifically bind to a target antigen or compete with other antibodies or antigen-binding fragments in order to bind to a specific epitope. Specifically, the antigen-binding fragment is an antibody fragment comprising one or more of the complementarity determining regions, and for example may be one selected from the group consisting of scFv, (scFv)$_2$, scFv-Fc, Fab, Fab' and F(ab')$_2$, but is not limited thereto. These biologically active fragments can be produced by recombinant DNA technology or, for example, by enzymatic or chemical cleavage of intact antibodies Immunologically functional fragments of immunoglobulin are not limited thereto.

"Humanized" forms of non-human (e.g., chicken, mouse, rat, etc.) antibodies are specific chimeric immunoglobulins, immunoglobulin chains or fragments thereof that contain minimal sequences derived from non-human immunoglobulins (e.g., For example, Fv, Fab, Fab', F(ab)$_2$ or other antigen-binding products of the antibody). Generally, a humanized antibody is a human immunoglobulin (recipient antibody) in which the residues obtained from CDR of the recipient antibody is replaced with the residues having desired specificity, affinity and ability from CDRs of the non-human species antibody (donor antibody) such as mice, rat or rabbit. In some instances, Fv framework region (FR) residues of human immunoglobulins are replaced with corresponding non-human FR residues. In addition, the humanized antibody may contain residues which are not found in the CDR or FR sequences introduced to the recipient antibody. These modifications can be made to further refine and optimize antibody performance. In general, all or substantially all of the CDR regions in humanized antibodies correspond to regions of a non-human immunoglobulin, and all or substantially all of the FR residues may include at least entire of one, commonly two of variable domains residues of a human immunoglobulin consensus sequence. The humanized antibody will also optimally include at least a portion of an immunoglobulin constant region (Fc), typically at least a portion of a human immunoglobulin.

The present invention relates to an antibody against an extracellular domain of the PDGFR-β isoform. PDGF receptor is a kind of tyrosine kinase enzyme, and includes two isoforms of PDGFR-α and PDGFR-β which can form three types of combinations of αα, ββ and αβ dimers. The structure of the PDGF receptor includes an extracellular region composed of five immunoglobulin-like domains, a transmembrane region, and an intracellular region (tyrosine kinase region). The ligand binding region of the receptor is located in the front three immunoglobulin-like regions among the five immunoglobulin-like domains of the extracellular region. PDGF is known to induce dimerization of the receptors by binding to immunoglobulin-like domains 2 and 3 of the PDGF receptor, and to direct receptor-receptor interaction including immunoglobulin-like domains 4 and 5 for additional stabilization.

The antibodies according to the invention may be human antibodies and antibody fragments produced from the gene repertoire of immunoglobulin variable (V) domains from non-immunized donors in vitro, by using phage display technology (McCafferty et al., (1990) Nature, 348: 552-553).

The present invention relates to an isolated antibody or antigen-binding fragment thereof that specifically binds to PDGFR-β, wherein the antibody or antigen-binding fragment may be a polypeptide, protein or antibody or an antigen-binding fragment thereof including a complementarity determining region of a heavy chain and a complementarity determining region of a light chain, to specifically bind to PDGFR-β.

In a specific example, the anti-PDGFR-β antibody and antigen-binding fragment thereof may include:
(i) at least one heavy chain complementarity determining region selected from the group consisting of H-CDR1, H-CDR2 and H-CDR3, or a heavy chain variable region including the at least one heavy chain complementarity determining region;
(ii) at least one light chain complementarity determining region selected from the group consisting of L-CDR1, L-CDR2, and L-CDR3, or a light chain variable region including the at least one light chain complementarity determining region;
a combination of the at least one heavy chain complementarity determining region and the at least one light chain complementarity determining region; or a combination of the heavy chain variable region and the light chain variable region.

Additionally, in the heavy chain variable region, the light chain variable region, or a combination of the heavy chain variable region and the light chain variable region, the heavy chain variable region may include one or more heavy chain frameworks selected from the group consisting of H-FR1, H-FR3 and H-FR4, and the light chain variable region may include one or more light chain frameworks selected from the group consisting of L-FR1, L-FR2, L-FR3, and L-FR4.

The heavy chain complementarity determining region of (i) H-CDR1, H-CDR2 or H-CDR3 according to the present invention is selected from amino acid sequences shown in Tables 1 and 2 below, or includes at least one amino acid sequence having substantial sequence identity with the selected amino acid sequence. In addition, (ii) the light chain complementarity determining region of L-CDR1, L-CDR2 or L-CDR3 is selected from amino acid sequences shown in Tables 1 and 2 below, or includes at least one amino acid sequence having substantial sequence identity with the selected amino acid sequence.

In the present invention, the single-chain Fv is a single polypeptide chain of an antigen-binding region in which the heavy variable region and light chain variable region are connected directly or by a linker, and can be at least one selected from scFv of the heavy chain variable region and the light chain variable region are linked in a single chain form, scFv dimers (di-scFv), and scFv-Fc in which a heavy chain variable region, a light chain variable region, and Fc are linked in a single chain form. The scFv may be the heavy chain variable region and light chain variable region connected by a linker that is not particularly limited, and for example, may be a linker sequence having an amino acid sequence of SEQ ID NO: 57 in Table 2 below.

The present invention includes an antibody against a platelet-derived growth factor receptor beta (PDGFR-β) of mouse or human as an example of target antigen, and scFv of the antibody can be used for producing a bispecific antibody. For example, the scFv may be an antibody in which a heavy chain having CDR1 to CDR3 and a light chain having CDR1 to CDR3 of an antibody are connected by a linker. Additionally, as a bispecific antibody, the fusion protein of (scFv of anti-PDGFR-β antibody)-Cκ-(scFv of anti-cotinine antibody) may include three (3) CDRs of the heavy chain and three (3) CDRs of the light chain of each antibody which can be linked to Cκ as specified in Table 2 below.

In a specific example, specific examples of antibodies against mouse PDGFR-β (mPDGFR-β) as an example of a target antigen according to the present invention, are PRb-CN01, PRb-CC01, PRb-CC02 and PRb-CC03, and their heavy chain variable region, light chain variable region, and CDR sequences of these regions are shown in Table 1 below.

TABLE 1

| Clone/name | Part | Amino acid sequence (N→C) | SEQ ID NO |
|---|---|---|---|
| PRb-CN01 | CDR1-VH | GFTFSDRAMH | 1 |
| PRb-CN01 | CDR2-VH | LITNTGGSTNYGAAVKG | 2 |
| PRb-CN01 | CDR3-VH | GVGSWAHGGRIDA | 3 |

TABLE 1-continued

| Clone/name | Part | Amino acid sequence (N→C) | SEQ ID NO |
|---|---|---|---|
| PRb-CN01 | CDR1-VL | SGGSGSYG | 4 |
| PRb-CN01 | CDR2-VL | SNNQRPS | 5 |
| PRb-CN01 | CDR3-VL | GTRDSSYVGI | 6 |
| PRb-CN01 | VH | AVTLDESGGGLQTPGGALSLVCKASGFTFSDRAMHWVRQAPGKGLEWVGLITNTGGSTNYGAAVKGRATISRDNGQSTVRLQLNNLRAEDTGTYYCTRGVGSWAHGGRIDAWGHGTEVIVSS | 7 |
| PRb-CN01 | VL | LTQPSSVSANPGETVKITCSGGSGSYGWFQQKSPGSAPVTVIYSNNQRPSDIPSRFSGSKSGSTNTLTITGVQAEDEAIYYCGTRDSSYVGIFGAGTTLTVL | 8 |
| PRb-CC01 | CDR1-VH | SGFTFSSYNMG | 9 |
| PRb-CC01 | CDR2-VH | GISAADNSTAYGAAVDG | 10 |
| PRb-CC01 | CDR3-VH | GGGSIDA | 11 |
| PRb-CC01 | CDR1-VL | SGGGSYYG | 12 |
| PRb-CC01 | CDR2-VL | YNDKRPS | 13 |
| PRb-CC01 | CDR3-VL | GAWDNSAGYAG | 14 |
| PRb-CC01 | VH | AVTLDESGGGLQTPGGALSLVCKGSGFTFSSYNMGWVRQAPGKGLEFVAGISAADNSTAYGAAVDGRATISRDNGQSTVRLQLNNLRAEDTATYFCIRGGGSIDAWGHGTEVIVSS | 15 |
| PRb-CC01 | VL | LTQPSSVSANLGGTVKITCSGGGSYYGWYQQKSPGSAPVTLIYYNDKRPSDIPSRFSGSKSGSTGTLTITGVQAEDEAVYFCGAWDNSAGYAGFGAGTTLTVL | 16 |
| PRb-CC02 | CDR1-VH | GFTFSSYGMF | 17 |
| PRb-CC02 | CDR2-VH | GIDTGSGTNYGSAVKG | 18 |
| PRb-CC02 | CDR3-VH | GYAGTIDA | 19 |
| PRb-CC02 | CDR1-VL | SGGGGSYG | 20 |
| PRb-CC02 | CDR2-VL | YNDKRPS | 21 |
| PRb-CC02 | CDR3-VL | GSYNSSDSL | 22 |
| PRb-CC02 | VH | AVTLDESGGGLQTPGGALSLVCKASGFTFSSYGMFWVRQAPGKGLEWVAGIDTGSGTNYGSAVKGRATISRDNGQSTVRLQLNNLRAEDTGTYFCTRGYAGTIDAWGHGTEVIVSSTS | 23 |
| PRb-CC02 | VL | LTQPSSVSANPGETVKITCSGGGGSYGWYQQKSPGSAPVTVIYYNDKRPSDIPSRFSGSKSGSTGTLTITGVQAEDEAVYFCGSYNSSDSLFGAGTTLTVL | 24 |
| PRb-CC03 | CDR1-VH | GFTFSSYAMG | 25 |
| PRb-CC03 | CDR2-VH | GIDTAGGTAYGPAVKG | 26 |
| PRb-CC03 | CDR3-VH | SSYIDT | 27 |
| PRb-CC03 | CDR1-VL | SGGTYNYG | 28 |
| PRb-CC03 | CDR2-VL | WNDKRPS | 29 |
| PRb-CC03 | CDR3-VL | GSSDSSGLI | 30 |
| PRb-CC03 | VH | AVTLDESGGGLQTPGGTLSLVCKASGFTFSSYAMGWVRQAPGKGLEWVAGIDTAGGTAYGPAVKGRATISRDNGQSTVRLQLNNLRAEDTATYYCTRSSYIDTWGHGTEVIVSSTS | 31 |
| PRb-CC03 | VL | LTQPSSVSANPGETVKITCSGGTYNYGWYQQKSPGSAPVTVIYWNDKRPSDIPSRFSGSKSGSTGTLTITGVQAEDEAVYYCGSSDSSGLIFGAGTTLTVL | 32 |

Among PRb-CN01, PRb-CC01, PRb-CC02 and PRb-CC03 antibodies, PRb-CC01, PRb-CC0, and PRb-CC03 compete with mPDGF-BB, and the binding site is immunoglobulin-like domain 2 or 3 of PDGFR-β, but PRb-CN01 does not compete with mPDGF-BB and is expected to bind to the immunoglobulin-like domain 1, 4 or 5 of PDGFR-β. It was confirmed that both PRb-CN01 and PRb-32 showed the equivalent cytotoxicity regardless of the presence or absence of mPDGF-BB and that PRb-CN01 and PRb-32 were surrogate antibodies (FIG. 20a and FIG. 20b).

The novel antibodies according to the present invention, such as PRb-CN01, PRb-CC01, PRb-CC02 and PRb-CC03 antibodies, antibody fragments thereof, mixtures thereof or derivatives thereof have binding affinity in the range of $1 \times 10^{-7}$ M to $1 \times 10^{-10}$ M for the PDGF receptor, when they are used for producing a bispecific antibody with an anti-cotinine antibody.

It was confirmed that the PRb-CN01, PRb-CC02 and PRb-CC03 antibodies internalized into cells through endosomes, but PRb-CC01 was not internalized. Because antibody-drug conjugates internalize into cells and release drugs, toxic effects are important in how effectively they deliver drugs into cells. In addition, the internalization efficiency is different between antibodies that attach to the same target antigen on the cell surface. Thus, the selection of an antibody internalizing efficiently is very important in the efficacy of the antibody-drug complex.

In addition, the PRb-CN01, PRb-CC01, PRb-CC02 and PRb-CC03 antibodies exhibit cytotoxicity, and PRb-CN01 among the four antibodies has the highest cytotoxicity when it forms a complex with cotinine-duocarmycin. Therefore, it can be considered as the most effective targeting vehicle for drugs such as duocarmycin. Even after adding mPDGF-BB, the cytotoxicity of the bispecific including PRb-CN01 complexed with cot-duo or cot-duo-cot was still high. However, when mPDGF-BB was added, the toxicity of the three antibodies (PRb-CC01, PRb-CC02 and PRb-CC03) complexed with cot-duo or cot-duo-cot competing with mPDGF-BB was slightly reduced. In the present invention, the bispecific antibody related with PRb-CN01 did not compete with PDGF-BB and induced cytotoxicity regardless of the presence of PDGF-BB (FIGS. 5a to 5b).

Specific examples of antibodies against human PDGFR-β (hPDGFR-β) which are examples of target antigens according to the present invention are PRb-CN16, PRb-CN32, and PRb-CN26. The CDR sequences of these antibodies are shown in Table 2 below.

TABLE 2

| Clone/name | Part | Sequence | SEQ ID NO |
|---|---|---|---|
| PRb-CN16 | CDR1-VH | GFTFSSFNMA | 33 |
| PRb-CN16 | CDR2-VH | EISNTAGSTFYAPAVKG | 34 |
| PRb-CN16 | CDR3-VH | AAGTCYSHSCTGYIDA | 35 |
| PRb-CN16 | CDR1-VL | SGSSSSYG | 36 |
| PRb-CN16 | CDR2-VL | ENNQRPS | 37 |
| PRb-CN16 | CDR3-VL | GNADRSNSAGT | 38 |
| PRb-CN16 | VH | AVTLDESGGGLQTPGTALSLVCKASGFTFSSFNMAWVRQAPGKGLEFVGEISNTAGSTFYAPAVKGRATISRDNGQSTVRLQLNNLRAEDTAIYYCAKAAGTCYSHSCTGYIDAWGHGTEVIVSSTS | 39 |
| PRb-CN16 | VL | LTQPSSVSANPGETVKITCSGSSSSYGWYQQKSPGSAPVTLIYENNQRPSNIPSRFSGSKSGSTGTLTITGVQAEDEAVYYCGNADRSNSAGTFGAGTTLTVL | 40 |
| PRb-CN32 | CDR1-VH | GFTFSSFNMF | 41 |
| PRb-CN32 | CDR2-VH | GISTTGRYTGYGSAVQG | 42 |
| PRb-CN32 | CDR3-VH | SAGSTYSYWDSDAGLIDA | 43 |
| PRb-CN32 | CDR1-VL | SGGSNAGSYYYG | 44 |
| PRb-CN32 | CDR2-VL | SNNQRPS | 45 |
| PRb-CN32 | CDR3-VL | GSGDSSSIAA | 46 |
| PRb-CN32 | VH | AVTLDESGGGLQTPRGTLSLVCKASGFTFSSFNMFWVRQAPGKGLEFVAGISTTGRYTGYGSAVQGRGTISRDNGQSTVRLQLNNLRAEDTGTYYCAKSAGSTYSYWDSDAGLIDAWGHGTEVIVSSTS | 47 |
| PRb-CN32 | VL | LTQPSSVSANLGETVKITCSGGSNAGSYYYGWYQQKSPGSAPVTVIYSNNQRPSDIPSRFSGSTSGSTSLTITGVQVDDEAVYFCGSGDSSSIAAFGAGTTLTVL | 48 |
| PRb-CN26 | CDR1-VH | GFTFSDRGIH | 49 |
| PRb-CN26 | CDR2-VH | GIGNTGSYTAYAPAVKG | 50 |
| PRb-CN26 | CDR3-VH | RGFMDAGGIDA | 51 |
| PRb-CN26 | CDR1-VL | SGGGSYAGSYYYG | 52 |
| PRb-CN26 | CDR2-VL | DNTNRPS | 53 |
| PRb-CN26 | CDR3-VL | GGYDGISDTGI | 54 |
| PRb-CN26 | VH | AVTLDESGGGLQTPGGGLSLVCKASGFTFSDRGIHWVRQAPGKGLEWVAGIGNTGSYTAYAPAVKGRATISRDNGQSTVRLQLNNLRAEDTATYYCAKRGFMDAGGIDAWGHGTEVIVSSTS | 55 |
| PRb-CN26 | VL | LTQPSSVSANPGETVKITCSGGGSYAGSYYYGWYQQKSPGSAPVTVIYDNTNRPSNIPSRFSGSLSGSTDTLTITGVQAEDEAVYFCGGYDGISDTGIFGAGTTLTVL | 56 |
| Linker (for producing scFv) | VL-VH | GQSSRSSGGGGSSGGGGS | 57 |
| Kappa constant (Ck) | * | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSLPVTKSFNRGES | 58 |
| Linker (for producing bispecific antibody) | scFv-Ck | (GGGGS)3 | 59 |

The PRb-CN16, PRb-CN32, and PRb-CN26 antibodies do not compete with hPDGF-BB, and thus, are expected to bind to immunoglobulin-like domains 1, 4 or 5 of hPDGFR-β. All of PRb-CN16, PRb-CN32 and PRb-CN26 antibodies are confirmed to bind to hPDGFR-β, mPDGFRβ, Rhesus PDGFRβ, Cynomolgus monkey PDGFRβ, and Sus crowfa PDGFRβ. It was confirmed that both PRb-CN01 and PRb-32 showed the equivalent cytotoxicity regardless of the presence/absence of mPDGF-BB, and PRb-CN01 and PRb-32 were surrogate antibodies (FIG. 20a and FIG. 20b).

The novel antibodies according to the present invention, such as PRb-CN16, PRb-CN32, and PRb-CN26 antibodies, antibody fragments, mixtures thereof or derivatives thereof, have binding affinity $1 \times 10^{-7}$ M to $1 \times 10^{-11}$ M to PDGF receptor, in the case that they are used for preparing a bispecific antibody with an anti-cotinine antibody.

In the evaluation of the cellular internalization performance of an antibody against human PDGFR-β (hPDGFR-β) as an example of a target antigen according to the present invention in the absence of hPDGF-BB, PRb-CN32 internalizes most effectively to human pericyte cells, PRb-CN16 is the second performance, and PRb-CN26 is not internalized. Also, in the evaluation of the cellular internalization performance with treatment by hPDGF-BB, all of PRb-CN16, PRb-CN32, and PRb-CN26 antibodies have excellent cell internalization performance. When preparing an antibody-drug conjugate, it is internalized into the cell and releases drug. Therefore, the hPDGFR-β antibody according to the present invention moves to the target cell and internalizes well. When the antibody-drug conjugate is prepared using the antibody, it is internalized into the cell and releases the drug, resulting in contributing to the increased drug efficacy. Patients with diseases associated with problematic wet type AMD and PDGFR-β have increased expression level of PDGFR-β and/or increased expression level of PDGF-BB, and these increased expression levels tend to inhibit internalization or efficacy of antibodies. In this regard, the anti-PDGFR-β antibody according to the present invention has an advantage that the internalization level of the antibody is not suppressed or the internalization is further increased, even if the expression level of PDGF-BB is increased.

When PRb-CN32 and PRb-CN26 form a complex with cotinine-duocarmycin among the PRb-CN16, PRb-CN32 and PRb-CN26 antibodies, they exhibit the highest cytotoxicity. Therefore, they can be considered as most effective targeting vehicle for drugs such as duocarmycin.

All of PRb-CN16, PRb-CN32, and PRb-CN26 showed higher cytotoxicity than the control anti-mCD154 x cotinine scFv-Cκ-scFv in PDGFR-β-expressing cell lines with or without hPDGF-BB, and especially, PRb-CN26 and PRb-CN32 showed high cytotoxicity (FIGS. 14a and 14b). In addition, all of PRb-CN16, PRb-CN32, and PRb-CN26 have equivalent cytotoxicity in a cell line that does not express hPDGFR-β, compared to the control anti-mCD154 x cotinine scFv-Cκ-scFv. Therefore, the bispecific antibody-drug ($IC_{50}$) has different toxicity in cell lines not expressing hPDGFR-β and cell lines expressing hPDGFR-β, shows toxicity at a lower concentration in hPDGFR-β expressing cell lines, and at that concentration, has higher toxicity in pathological cells or tissues expressing much hPDGFR-β, with minimizing toxicity in normal cells or normal tissues. In addition, patients with diseases related problematic Wet type AMD and PDGFR-β have increased PDGFR-β expression levels (C. Zehetner et al., Invest Ophthalmol Vis Sci. 55 (2014) 337-44) and/or increased PDGF-BB expression level (C. Zehetner, R. Kirchmair, S B Neururer, M T Kralinger, N E Bechrakis, G F Kieselbach, Systemic upregulation of PDGF-B in patients with neovascular AMD, Invest Ophthalmol Vis Sci. 55 (2014) 337-44)), and these increased expression levels tend to inhibit the internalization or efficacy of the antibody. In this regard, the anti-PDGFR-β antibody according to the present invention has the advantage that the internalization level of the antibody is not suppressed or the internalization is further increased, even if the expression level of PDGF-BB is increased.

More specifically, the antibody according to the present invention specifically binds to platelet-derived growth factor receptor beta (PDGFR-β), and may be anti-PDGF receptor antibody or antigen binding fragment thereof including a heavy chain variable region and a light chain variable region, wherein the heavy chain variable region of the anti-PDGF receptor antibody includes VH-CDR1 comprising an amino acid sequence of SEQ ID NO: 1, 9, 17, 25, 33, 41, or 49, VH-CDR2 comprising an amino acid sequence of SEQ ID NO: 2, 10, 18, 26, 34, 42 or 50, and VH-CDR3 comprising an amino acid sequence of SEQ ID NO: 3, 11, 19, 27, 35, 43 or 51, and wherein the light chain variable region of the anti-PDGF receptor antibody is VL-CDR1 comprising an amino acid sequence of SEQ ID NO: 4, 12, 20, 28, 36, 44, or 52, VL-CDR2 comprising an amino acid sequence of SEQ ID NO: 5, 13, 21, 29, 37, 45, or 53, and VL-CDR3 comprising an amino acid sequence of SEQ ID NOs: 6, 14, 22, 30, 38, 46 or 54.

The anti-PDGF receptor antibody or antigen-binding fragment thereof binds non-competitively to PDGF-BB, and includes, for example, the heavy chain variable region includes VH-CDR1 comprising an amino acid sequence of SEQ ID NO: 1, 33, 41 or 49, VH-CDR2 comprising an amino acid sequence of SEQ ID NO: 2, 34, 42 or 50, and VH-CDR3 comprising an amino acid sequence of SEQ ID NO: 3, 35, 43 or 51, and the light chain variable region including VL-CDR1 comprising an amino acid sequence of SEQ ID NO: 4, 36, 44, or 52, VL-CDR2 comprising an amino acid sequence of SEQ ID NO: 5, 37, 45, or 53, VL-CDR3 comprising an amino acid sequence of SEQ ID NO: 6, 38, 46 or 54.

The anti-PDGF receptor antibody or antigen-binding fragment thereof may be internalized by a cell expressing PDGFR-β, and include, for example, the heavy chain variable region includes VH-CDR1 comprising an amino acid sequence of SEQ ID NO: 1, 17, 25, 33, 41, or 49, VH-CDR2 comprising an amino acid sequence of SEQ ID NO: 2, 18, 26, 34, 42 or 50, and VH-CDR3 comprising an amino acid sequence of SEQ ID NO: 3, 19, 27, 35, 43 or 51, and the light chain variable region includes VL-CDR1 comprising an amino acid sequence of SEQ ID NO: 4, 20, 28, 36, 44, or 52, VL-CDR2 comprising an amino acid sequence of SEQ ID NO: 5, 21, 29, 37, 45, or 53, and VL-CDR3 comprising an amino acid sequence of SEQ ID NO: 6, 22, 30, 38, 46 or 54.

Specific anti-PDGF receptor antibody or antigen-binding fragment thereof of the present invention may include:
(a) VH-CDR1 to VH-CDR3 each comprising an amino acid sequence of SEQ ID NOs: 1 to 3 and VL-CDR1 to VL-CDR3 each comprising an amino acid sequence of SEQ ID NOs: 4 to 6,
(b) VH-CDR1 to VH-CDR3 each comprising an amino acid sequence of SEQ ID NOs: 9 to 11 and VL-CDR1 to VL-CDR3 each comprising an amino acid sequence of SEQ ID NOs: 12 to 14,
(c) VH-CDR1 to VH-CDR3 each comprising an amino acid sequence of SEQ ID NOs: 17 to 19 and VL-CDR1 to VL-CDR3 each comprising an amino acid sequence of SEQ ID NOs: 20 to 22,
(d) VH-CDR1 to VH-CDR3 each comprising an amino acid sequence of SEQ ID NOs: 25 to 27 and VL-CDR1 to VL-CDR3 each comprising an amino acid sequence of SEQ ID NOs: 28 to 30,
(e) VH-CDR1 to VH-CDR3 each comprising an amino acid sequence of SEQ ID NOs: 33 to 35 and VL-CDR1 to VL-CDR3 each comprising an amino acid sequence of SEQ ID NOs: 36 to 38,
(f) VH-CDR1 to VH-CDR3 each comprising an amino acid sequence of SEQ ID NOs: 41 to 43 and VL-CDR1 to VL-CDR3 each comprising an amino acid sequence of SEQ ID NOs: 44 to 46, or
(g) VH-CDR1 to VH-CDR3 each comprising an amino acid sequence of SEQ ID NOs: 49 to 50 and VL-CDR1 to VL-CDR3 each comprising an amino acid sequence of SEQ ID NOs: 52 to 54.

An embodiment of the present invention relates to a use of a drug delivery system that delivers a drug to cells or tissues having PDGF receptor, specifically PDGF receptor-β on a cell surface, and includes an anti-PDGF receptor antibody. The anti-PDGF receptor antibody or antigen-binding fragment thereof is targeted to a target cell having PDGF receptor and is internalized to the inside of target cell, so as to efficiently deliver substances conjugated to the antibody or antigen-binding fragment thereof into the target cell. The drug to be delivered is a drug capable of binding to an anti-PDGF receptor antibody directly or through a linker, so as to form an antibody-drug conjugate, or a hapten-drug conjugate to bind to an anti-PDGF receptor antibody through a hapten.

An embodiment of the present invention provides a complex including an anti-PDGF receptor antibody or antigen-binding fragment thereof being capable of a conjugating compound such as a chemotherapeutic drug, enzyme, peptide, aptamer, toxin, affinity ligand, or detection label, and a conjugating compound. Depending on the type of the conjugating compound, the complex may be variously applied to diagnosis or treatment of a disease.

A further embodiment of the present invention relates to an antibody-drug conjugate in which a drug is conjugated to the anti-PDGF receptor antibody or antigen-binding fragment of the antibody. The antibody-drug conjugate may be a conjugate in which a drug is bound to an anti-PDGF receptor antibody by a non-covalent bond or covalent bond.

As used herein, "conjugating body" or "conjugate" refers to an antibody or antigen-binding fragment thereof and other molecule disclosed hereafter, particularly a chimeric molecule of a therapeutic agent described below. In the conjugate, the antibody or antigen-binding fragment thereof according to the present invention is linked physically to the other molecule by covalent bond or physical force of Van Der Waals force or hydrophobic interaction, encapsulation, embedding or a combination of the above. In the conjugate according to an embodiment, the antibody or antigen-binding fragment thereof according to the present invention may be linked through a peptide linker.

Another embodiment of the present invention may be a bispecific antibody including an anti-PDGF receptor antibody or antigen-binding fragment thereof specifically recognizing hapten that is capable of conjugating with a drug. The antigen-binding fragment of the antibody refers to a fragment of an antibody having at least one CDR, and may be scFv, (scFv)$_2$, scFv-Fc, Fab, Fab' and F(ab')$_2$. In the present invention, "multispecific antigen-binding protein" or "multispecific antibody" targets two or more antigens or epitopes, and includes two or more antigen-binding sites. In the present invention, "bispecific" or "dual specific" antigen binding protein or antibody is a hybrid antigen binding protein or antibody having two different antigen binding sites. Such a bispecific antibody is a kind of multispecific antigen binding protein or multispecific antibody, and can be produced by various known methods, for example, fusion of hybridomas or connection of Fab' fragments.

In case that the drug delivery system according to the present invention includes a hapten-recognizing antibody or antigen-binding fragment thereof, the drug may bind to hapten and then binds to the anti-PDGF receptor antibody or antigen-binding fragment thereof through hapten, so as to be targeted to cells. The drug delivered to the target cell may be a drug for preventing, improving or treating PDGF or PDGF receptor-related diseases, for example, neovacular disorders.

An embodiment of the present invention is a pharmaceutical composition for preventing, improving or treating neovascular disease, comprising an antibody-drug conjugate in which a drug is conjugated to the anti-PDGF receptor antibody or antigen-binding fragment thereof, or an antibody-drug conjugate in which a drug is conjugated to the anti-PDGF receptor antibody or antigen-binding fragment thereof through hapten.

An embodiment of the present invention relates to a method of treating a subject diagnosed as suffering from a neovacular disease or having a risk of occurrence of a neovacular disease, comprising a step of administering an antibody-drug conjugate in which a drug is conjugated to the anti-PDGF receptor antibody or antigen-binding fragment thereof, or an antibody-drug conjugate in which a drug is conjugated via hapten to the anti-PDGF receptor antibody or antigen-binding fragment thereof, to the subject at a sufficient amount of preventing, improving or treating the diseases in the subject as a first therapeutic agent or an auxiliary therapeutic agent.

In another embodiment, the pharmaceutical composition of the present invention provides a means for preventing, improving, inhibiting or treating an ocular neovascular disease.

Ocular neovascular diseases that can be treated or suppressed by the pharmaceutical composition of the present invention include ischemic retinopathy, iris neovascularization, intraocular neovascularization, senile Age-related macular degeneration, corneal neovascularization, retinal neovascularization, choroidal neovascularization, diabetic retinal ischemia, or proliferative diabetic retinopathy.

Specifically, an animal model with the oxygen-induced retinal disease is an animal model of retinopathy of premature baby (A. Hellström, L E Smith, D. Dammann, Retinopathy of prematurity, Lancet. 382 (2013) 1445-57). An animal model with laser-induced choroidal neovascularization is an animal model of wet type senile macular degeneration (V. Lambert, J. Lecomte, S. Hansen, S. Blacher, M L. Gonzalez, et al, Laser-induced choroidal neovascularization model to study age-related macular degeneration in mice, Nat Protoc. 8 (2013) 2197-211). Both of them are diseases caused by an important mechanism of angiogenesis. Like proliferative diabetic retinopathy, it can also be used as a therapeutic agent for diseases such as proliferative diabetic retinopathy, in which angiogenesis is an important mechanism (Y. Qazi, Mediators of ocular angiogenesis, J. Genet. 88 (2009) 495-515)).

In another embodiment, the pharmaceutical composition of the present invention provides a means for preventing, ameliorating, inhibiting or treating neovascular diseases neovascular disease such as cancer or tumor. The cancer is a cancer having a problem with PDGFR-β, and includes retinoblastoma, glioma, testicular cancer, breast cancer, ovarian cancer, melanoma, lung cancer, and prostate cancer, but is not limited to.

In addition, the diseases having a problem with PDGFR-β which shows cytotoxicity in NIH3T3 expressing mPDGFRb and human pericyte cells expressing hPDGFR-β include retinoblastoma (Z K Goldsmith et al., Invest. Ophthalmol. Vis. Sci. 59 (2018) 4486-4495), glioma (I. Nazarenko et al., J. Med. Sci. 117 (2012) 99-112), colorectal cancer (S. Fujino et al., Oncol. Rep. 39 (2018) 2178-2184), testicular cancer (S. Basciani et al., Endocrinology. 149 (2008) 6226-35), breast cancer (J. Paulsson et al., J. Pathol) Clin. Res. 3 (2017) 38-43), ovarian cancer (S. Avril et al., Oncotarget. 8 (2017) 97851-97861), melanoma, lung cancer, prostate cancer (M. Raica et al., Pharmaceuticals (Basels). 3 (2010) 572-599), and the like.

As used herein, the terms "angiogenesis" and "neovascularization" are used interchangeably. Angiogenesis and neovascularization refer to the development of new blood vessels into cells, tissues, or organs. The regulation of angiogenesis typically changes in certain disease states, and in many cases, the pathological damage associated with this disease is associated with altered, unregulated or uncontrolled angiogenesis. Persistent, unregulated angiogenesis occurs in a number of disease states including those characterized by abnormal growth of endothelial cells, and supports the pathological damage observed in these conditions including leakage and permeability of blood vessels.

In the present specification, "ocular neovascular disease" or "ocular neovascular disease" refers to a disease characterized by neovascularizsation that is not changed or controlled in the eye of a subject. Exemplary ocular neovascular diseases include ischemic retinopathy, iris angiogenesis, intraocular angiogenesis, senile macular degeneration, conical angiogenesis, retinal angiogenesis, choroidal angiogenesis, diabetic retinal ischemia, proliferative diabetic retinopathy, and the like.

As used herein, "PDGF" or "platelet-derived growth factor" refers to a mammalian platelet-derived growth factor that affects neovascularization or angiogenesis process. As used herein, the term "PDGF" generally refers to a class of growth factors that induce DNA synthesis and mitosis through binding and activation of platelet-derived growth factor cell surface receptors (ie, PDGF receptors) to reactive cell types.

In the present invention, it is observed that the single-chain variable fragment (scFv) of an antibody against platelet-derived growth factor receptor beta (mPDGFR-β)-kappa constant region (Cκ)-scFv fusion protein, and cotinine-duocarmycin form an antibody-drug conjugate complex to induce cytotoxicity against PDGFR-β-expressing cells. An improved approach for antibody selection in antibody-drug conjugate preparation is demonstrated by preparing a number of anti-mPDGFR-β antibody candidates in the bispecific scFv-Cκ-scFv fusion protein format and testing their ability to deliver cytotoxic drugs binding to cotinine.

An embodiment of the present invention relates to a method of selecting an antibody that efficiently delivers a drug into a target cell using a hapten-drug conjugate and a bispecific antibody.

A further embodiment of the present invention relates to a drug-antibody conjugate comprising the selected antibody and a drug, or a complex comprising the selected antibody and a drug-hapten.

The hapten-drug conjugate used in the method of the present invention refers to a conjugate in which a target drug to be delivered to a target cell and a hapten are connected. The hapten is a substance that does not exist naturally in body to prevent binding to cells, does not de novo biosynthesized in body, does not cause physiological activity, and has a chemical functional group for effective binding with a substance to be conjugated with. Hapten usable in the present invention is not particularly limited, but for example, can be selected from cotinine, organic molecules with small molecular weight such as DNP (2,4-dinitrophenol), TNP (2,4,6-trinitrophenol), biotin, and digoxigenin.

As an example of the hapten, cotinine is an ideal hapten to be used in this platform because of exogeneity, non-toxicity, and physiological inertness as a major metabolite of nicotine. Trans-4-cotininecarboxylic acid can bind to several substances. The cotinine-drug conjugate can be easily synthesized, and has higher purity than that of the existing antibody-drug conjugate, and can be synthesized as a cotinine-drug conjugate having various drugs and linkers. In addition, since the drug is not directly conjugated to the antibody, it does not affect the affinity and stability of the antibody. The antibody-drug conjugates are made by simply reacting a bispecific antibody with a cotinine-drug conjugate.

Drugs applicable to the present invention are substances to be delivered to a target using antibodies and are not particularly limited, but for example, include DNA synthesis inhibitors (e.g., calicheamicin, pyrrolobenzodiazepine (PBD), duocarmyin derivative, anthracycline/Nemorubicin, doxorubicin, Irinotecan, amatoxin), Microtubule inhibitors (e.g., auristatin, maytansine, tubulysin), Topo-isomerase inhibitor (SN-38), photosensitizer (e.g., 5-Aminolaevulinic acid (ALA), Benzoporphyrin derivative monoacid ring A (BPD-MA), Chlorins, Tetra (m-hydroxyphenyl)chlorin (mTHPC), Lutetium texaphyrin), and the like. The photosensitizing agent alone does not exert its efficacy, but it is delivered locally or systemically to target cells or tissues or delivered, and activates the delivered drug by irradiating a laser to a specific area, for example, a lesion site such as eyeball or eye, thereby exerting the efficacy of the drug. Accordingly, the photosensitizing agent may be conjugated to an antibody and administered to a subject in need of, and then a step of exerting a medicinal effect by irradiating a laser may be additionally performed.

The method according to the present invention may use a bispecific antibody that binds specifically binds to the target antigen present in the target tissue or cell to which the drug is delivered, and can also specifically bind to the hapten included in the hapten-drug conjugate. For example, bispecific antibody applicable to the present invention may have a structure of first antibody-linker-second antibody, in which the first antibody and the second antibody are antibodies that specifically bind to a hapten or a target antigen, respectively. The bispecific antibody having the structure of the first antibody-linker-second antibody may be a fusion protein of the first antibody (scFv)-Cκ(kappa constant)-second antibody (scFv). For example, it can be connected in the order of VH-GQSSRSSGGGGSSGGGS (SEQ ID NO: 57)-VL from the N-terminus, and the linker connects C-terminus of VH to N-terminus of VL. It can be a structure of (ScFv of anti-PDGFR-β antibody)-(GGGGS)$_3$ (SEQ ID NO: 59)-Ck-(GGGGS)$_3$ (SEQ ID NO: 59)-(scFv of anti-cotinine antibody). An amino acid sequence or nucleotide sequence of cotinine applicable to the present invention is widely known in the art, and for example, is referred to U.S. Pat. No. 8,008,448B.

In an embodiment of the present invention, when the target antigen is platelet-derived growth factor receptor beta (PDGFR-β) and the hapten is cotinine, the bispecific antibody can be an antibody in which an antibody against a target antigen (anti-PDGFR-β antibody) and an antibody against hapten (anti-hapten antibody) is linked with a linker, and specifically, a fusion protein having the structure of the first antibody (scFv of anti-PDGFR-β antibody)-Cκ-the second antibody (scFv of anti-hapten antibody).

The present inventors tested the feasibility of this platform using a bispecific antibody fusion protein of (scFv of anti-human platelet-derived growth factor receptor beta (hPDGFRβ)×Cκ×(scFv of anti-cotinine antibody). The present inventors constructed monovalent or bivalent cotinine-duocarmycin, which are named as cotinine-duocarmycin (cot-duo) or cotinine-duocarmycin-cotinine (cot-duo-cot) (FIG. 1b). The present invention indicates that the platform can be used to screen optimal combination of antibodies and drug for development of antibody-drug conjugate, compared to conventional platform.

A complex including bispecific antibody (for example, anti-PDGFRβ x cotinine scFv-C, scFv fusion protein) and hapten-drug conjugate (for example, cotinine-conjugated duocarmycin), shows specific cytotoxicity in NIH3T3 cell lines expressing target antigen (for example, mPDGFR-β). The present invention can be used to select the combination of internalizing antibody and drug in the development of antibody-drug conjugate. For example, four antibody clones bound to mPDGFR-β coated in bottom in a dose-dependent manner (FIG. 3a), while they had no reactivity against negative control-human Fc protein. The present inventors confirmed the binding activity of individual clones to NIH3T3 cell lines expressing mPDGFRβ and found that biotin-mPDGF-BB bound to the cells with using a flow cytometry (FIG. 4b).

Antibody clones (PRb-CC01, PRb-CC02, and PRb-CC03) against three types of mouse antigens according to the present invention may bind to domain 2 or 3 of mPDGFR-β by competing with mPDGF-BB which is a ligand of mPDGFR-β. One antibody clone (PRb-CN01) may bind to domains 1, 4, or 5 instead of domains 2 and 3, because it does not compete with mPDGF-BB. The binding abilities of PRb-CC01, PRb-CC02, and PRb-CC03 to mPDGFR-β were inhibited by mPDGF-BB (FIG. 4a), but the binding ability of PRb-CN01 was not inhibited by mPDGF-BB. The present inventors measured the cell binding ability of each clone using flow cytometry, when mPDGF-BB was present in NIH3T3 cells expressing mPDGFR-β. The present inventors found that the bispecific antibody of scFv-Cκ-scFv fusion protein and biotin-mPDGF-BB bound to the cells. Like the result of competition enzyme immunoassay, only PRb-CN01 was able to bind to mPDGFR-β in the presence of mPDGF-BB-biotin (FIG. 4b), and the binding capacity of the other three clones was blocked by mPDGF-BB.

When the antibodies of the present invention were expressed in the form of a bispecific antibody of scFv-Cκ-scFv, the bispecific antibodies were capable of binding to both mPDGFR-β and cotinine. In addition, the bispecific antibodies could be conjugated with several cotinine drugs such as cotinine-duocarmycin (cot-duo) and cotinine-duocarmycin-cotinine (cot-duo-cot). When conducting toxicity tests with complexes such as cot-duo and cot-duo-cot, the complexes are toxic. The four bispecific antibodies of scFv-Cκ-scFv fusion proteins (PRb-CC01, PRb-CN01, PRb-CC02, PRb-CC03) were capable of simultaneously binding to mPDGFR-β and cotinine, unlike the control bispecific antibody (FIG. 3d).

To evaluate the toxicity of the four types of bispecific antibodies of scFv-Cκ-scFv and cotinine-duocarmycin conjugates, NIH3T3 cells were cultured together with the conjugates under two conditions with or without mPDGF-BB, and were tested for the relative cell viability using intracellular adenosine triphosphate (ATP). The toxicity of the PRb-CN01 and cot-duo complex or the PRb-CN011 and cot-duo-cot complex was also high with the addition of mPDGF-BB, but toxicity rate of the fusion proteins (PRb-CC01, PRb-CC02, PRb-CC03) competing with mPDGF-BB and cot-duo complex or cot-duo-cot complex decreased with the addition of mPDGF-BB (FIG. 5).

In the present invention, the scFv-Cκ-scFv bispecific antibody fusion protein and cotinine-duocarmycin (cot-duo) were prepared respectively (FIG. 1b), and then conjugate of the bispecific antibodies scFv-Cκ-scFv and cotinine-duocarmycin was prepared and performed for the toxicity test. As a result, they showed characteristic toxicity in human pericyte cells expressing hPDGFR-β. The result of the present invention indicates that it is possible to select an optimal antibody and drug combination for the development of antibody-drug conjugates compared to the convention platforms.

For example, it was shown that three antibody clones binding to hPDGFR-β of an example of a target antigen according to the present invention, bound to hPDGFR-β in a concentration-dependent manner. The three fusion proteins were concentration-dependently bound to hPDGFR-β coated on the bottom (FIG. 12a), while the negative control did not bind to the coated human Fc protein (FIG. 12b). In the present invention, it was confirmed that the ability of each clone binding to human pericyte cells expressing hPDGFR-β in the presence of hPDGF-BB was analyzed using a flow cytometer, resulting in biotin-hPDGF-BB bound to the cells (FIG. 13b).

The three types of antibody clones against hPDGFR-β according to the present invention (PRb-CN16, PRb-CN32, PRb-CN26) did not compete with hPDGF-BB of a ligand of hPDGFR-β, and thus was expected to bind to domains 1, 4 or 5 instead of domains 2 and 3. The binding ability of PRb-CN16, PRb-CN32, and PRb-CN26 to hPDGFR-β was not inhibited by hPDGF-BB (FIG. 13a).

In the present invention, when hPDGF-BB is present in human pericyte cells expressing hPDGFR-β, the cell binding ability of each clone was measured using flow cytometry. It was confirmed that the bispecific antibody of scFv-Cκ-scFv fusion protein and biotin-hPDGF-BB were bound. Like the result of competitive enzyme immunoassay method, three kinds of antibody clones (PRb-CN16, PRb-CN32, PRb-CN26) were able to bind to hPDGFR-β in the presence of hPDGF-BB-biotin (FIG. 13b). When the antibody against the target antigen according to the present invention is expressed in the form of a bispecific antibody of scFv-Cκ-scFv, the bispecific antibody can bind to both the target antigen and the hapten. In addition, the bispecific antibodies can be complexed with several cotinine-drug conjugates such as cotinine-duocarmycin (cot-duo). When conducting toxicity tests with the conjugates such as cot-duo, the complexes are toxic.

The three bispecific antibodies of scFv-Cκ-scFv fusion proteins (PRb-CN16, PRb-CN32, PRb-CN26) against human PDGFR-β according to the present invention were capable of simultaneously binding hPDGFR-β and cotinine unlike the control bispecific antibody (FIG. 12d). To evaluate the toxicity of the bispecific antibody of scFv-Cκ-scFv and cotinine-duocarmycin conjugates prepared by using three types of hPDGFR-β antibodies, human pericyte cells were cultured with the conjugates under two different conditions with or without hPDGF-BB, and the relative cell viability was measured with intracellular adenosine triphosphate (ATP). The toxicity of the complexes consisting of anti-hPDGFR-βantibody of PRb-CN16, PRb-CN32, PRb-CN26, and the cot-duo was also high with the addition of hPDGF-BB (FIGS. 14a and 14b).

The present inventors tested a new platform for developing antibody-drug conjugate consisting of bispecific scFv-Cκ-scFv fusion protein and cotinine-cytotoxic drug, which simplifies the process for selecting antibody and drug for the optimal antibody-drug conjugate. Ideally, it is practical to select antibodies that ensure efficient internalization and cytotoxic drug release. However, since the production of individual specific antibody-drug conjugate molecules using candidate antibodies requires considerable work to optimize and characterize including DAR (drug-antibody ratio), antibodies have been screened based on the speed and efficiency of internalization in the initial screening step. Moreover, as the process by which antibody-drug conjugates act on cells is understood better, it can be seen that internalization of antibodies is not the only factor determining the efficacy of antibody-drug conjugates.

Cotinine is not toxic and has an $LD_{50}$ value of 4±0.1 g/kg in rats. In addition, no adverse side effects were induced in persons treated with up to 1,800 mg of cotinine for 4 consecutive days. The present inventors have observed that there is a slight difference between the cytotoxicity of free duocarmycin and cotinine-duocarmycin conjugates in an ex vivo environment. The formation of a complex between the anti-HER2 antibody x cotinine of scFv-Cκ-scFv fusion protein and the cotinine-duocarmycin conjugate lowers the toxicity of duocaramycin in the ex vivo environment. It implies that the bispecific antibody forms a complex with the drug and decreases the absorption of the drug into the cell. In conventional studies, it was reported that duocarmycin induced significantly weight loss in mice. However in vivo experiment using a tetravalent bispecific antibody of the present invention, there was no significant weight loss in mice which a cotinine-duocarmycin conjugate mixed with a negative control IgG was injected into. This fact opens up the possibility of introducing various types of linkers between cotinine and a toxic drug (duocarmycin), and releasing toxins from cotinine only in the tumor environment like metalloproteases. Because the cotinine-drug conjugate is released without degradation in the tumor environment, it will be quickly removed from the blood flow without damaging normal cells.

Even after the addition of mPDGF-BB, the cytotoxicity of PRb-CN01-containing bispecific antibody complexed with cot-duo or cot-duo-cot was still high, but the addition of mPDGF-BB, which promotes cell proliferation, the toxicity of the three antibodies (PRb-CC01, PRb-CC02 and PRb-CC03), which competes with mPDGF-BB, complexed with either cot-duo or cot-duo-cot was slightly reduced. mPDGF-BB may strengthen the internalization of receptor by binding to PDGFR-β which has been already bound to PRb-CN01, thereby promoting the cytotoxic effects of cot-duo and cot-duo-cot. In the present invention, the PRb-CN01 construct did not compete with PDGF-BB and induced cytotoxicity independently of PDGF-BB (FIGS. 5a to 5d). PDGFR-β is highly associated with angiogenesis, and is mainly overexpressed in pericytes.

Effect of the Invention

In the antibody against the PDGF receptor according to the present invention, the antibody-drug conjugate in which a chemotherapeutic agent is conjugated to the antibody and the use of preventing or treating ocular neovascular diseases by using the same, the antibody against the PDGF receptor exhibits more toxicity specifically at a certain concentration to pathological cells or tissues that express a lot of hPDGFR-β, while minimizing toxicity to normal cells or normal tissues, thereby being applicable for an excellent therapeutic agent. In addition, the antibody against the PDGF receptor has an advantage that the internalization level of the antibody is not suppressed or is increased, even if the expression level of PDGFR-β and/or PDGF-BB increases.

BRIEF DESCRIPTION OF DRAWINGS

FIG. 1a and FIG. 1b are diagrams showing a bispecific antibody related to an anti-mPDGFR-β antibody and cotinine-duocarmycin according to an example of the present invention. The linker (GGGGS)$_3$ of FIG. 1a is shown in SEQ ID NO: 59 and the linker (GQSSRSSGGGGSSGGGGS) is shown in SEQ ID NO: 57.

FIG. 2 shows the result of SDS-polyacrylamide gel electrophoresis of the bispecific antibody related with the anti-mPDGFR-β antibody according to an example of the present invention. Lane 1, reduced PRb-CC03 x cotinine; Lane 2, non-reduced PRb-CC03 x cotinine; Lane 3, reduced PRb-CC01 x cotinine; Lane 4, non-reduced PRb-CC01 x cotinine; Lane 5, reduced PRb-CN01 x cotinine; Lane 6, non-reduced PRb-CN01 x cotinine; Lane 7, reduced PRb-CC02 x cotinine; Lane 8, non-reduced PRb-CC02 x cotinine; Lane 9, reduced anti-HER2 x cotinine (control); Lane 10, non-reduced anti-HER2 x cotinine (control). M: molecular weight marker.

FIG. 3a is a graph showing the binding ability of the bispecific antibody related with the anti-mPDGFR-β antibody according to an embodiment of the present invention, in which the bispecific antibody PRb-CC01 (●), PRb-CN01 (■), PRb-CC02 (▲), PRb-CC03 (▼) and a negative control (♦) were incubated on a plate coated with mPDGFR-β chimera. Each well was reacted with HRP-anti human Cκ antibody and TMB. The results show the mean value±standard error of the duplicate experiments. FIG. 3b shows the TNF-α receptor extracellular region-human Fc fusion protein used as a negative control antigen for enzyme immunoassay. In FIG. 3c, in order to confirm the binding ability of the bispecific antibody scFv-Cκ-scFv fusion protein to cotinine, the bispecific antibody scFv-Cκ-scFv was reacted to the plate coated with cotinine-BSA, and reacted with HRP-anti-human Cκ antibody and TMB. In FIG. 3d, in order to confirm the simultaneous binding ability of the bispecific antibody scFv-Cκ-scFv fusion protein to cotinine and mPDGFR-β, mPDGFR-β-Fc chimera was reacted to the plate coated with cotinine-BSA, and HRP-anti-human Fc Antibodies and TMB were treated. The results show the mean value±standard error of three repetitive experiments. ***$p<0.001$ was compared to the control group.

FIG. 4a to FIG. 4c are graphs confirming competition and intracellular internalization of PDGF-BB and bispecific antibodies related with anti-mPDGFR-β antibody. In FIG. 4a, the PDGFR-β-Fc chimera coated plate was reacted with scFv-Cκ-scFv in the absence (left) or presence (right) of mPDGF-BB (100 nM) and then the bound bispecific antibody fusion Protein was measured by HRP-anti-human Cκ antibody and TMB. In FIG. 4b, the bispecific antibody scFv-Cκ-scFv fusion protein (100 nM) in the flow cytometry buffer was reacted to NIH3T3 cells expressing mPDGFR-β with or without mPDGF-BB-biotin. The cells were treated with APC-anti human Cκ antibody and streptavidin-PE. The bispecific antibody anti-HER2 x cotinine scFv-Cκ-scFv fusion protein was used as a negative control. The internalization of the bispecific antibody scFv-Cκ-scFv fusion protein was visualized with confocal microscope. After NIH3T3 cells were treated by the fusion protein, antibodies bound on the cell surface were removed. After cell fixation, the fusion protein was stained with FITC-anti human Cκ antibody (green). To image early endosomes, the cells were stained with anti-Rab5 antibody and Alexa Fluor 546-goat anti-rabbit antibody IgG (red). The part indicated by the arrow shows the enlarged part in which the fluorescence of the anti-PDGFR-β x cotinine scFv-Cκ-scFv fusion protein and the initial endosome are co-localized. DNA was stained with DAPI (blue) (Scale bar, 10 μm)

FIG. 5a to FIG. 5d are graphs confirming the cytotoxic ability of the bispecific antibody against anti-mPDGFR-β and cotinine-duocarmycin complexes to cells expressing PDGFR-β. FIG. 5a shows that NIH3T3 cells were treated with a bispecific antibody scFv-Cκ-scFv fusion protein and a cot-duo complex without mPDGF-BB. Cellular ATP was measured to assess relative cell viability. The bispecific antibody anti-HER2 x cotinine scFv-Cκ-scFv fusion protein was used as a negative control. In FIG. 5b, the experiment was repeated in the presence of mPDGF-BB. In FIG. 5c, NIH3T3 cells were treated with a complex of bispecific antibody and cot-duo-cot without mPDGF-BB. In FIG. 5d, the experiment was repeated in the presence of mPDGF-BB. DMSO was used as a vehicle control for cot-duo and cot-duo-cot. The results show the mean value±standard error of three repetitive experiments.

FIG. 6 is a graph showing the experimental result of the binding ability of a bispecific antibody related with an anti-mPDGFR-β antibody according to the present invention to MOLT-4 cells not expressing PDGFR-β with a flow cytometer. MOLT-4 cells were treated with the bispecific antibody (100 nM) and stained with an APC-anti human Cκ antibody (clone TB28-2, BD Biosciences, San Jose, CA, USA).

FIG. 7 is a graph confirming the cytotoxic ability of the bispecific antibody related to the anti-mPDGFR-β antibody and cot-duo complexes in the cells not expressing PDGFR-β. In FIG. 7a, MOLT-4 cells were reacted with the bispecific antibody and cot-duo complex (DAR4). The cellular ATP was measured to evaluate the relative cell viability. In FIG. 7b, MOLT-4 cells were reacted with the bispecific antibody and cot-duo complex (DAR2). The bispecific antibody anti-HER2 x cotinine scFv-Cκ-scFv was used as a negative control. DMSO was used as a vehicle control for cot-duo. The results show the mean value±standard error of three repetitive experiments.

FIG. 8 shows a result of size exclusion chromatography of a bispecific antibody containing an anti-mPDGFR-β antibody according to the present invention. The bispecific antibodies, the complex of bispecific antibodies and cot-duo, the complex of bispecific antibodies and cot-duo-cot according to the present invention were analyzed with the size exclusion chromatography-HPLC using Dionex Ultimate 3000 equipped with a Sepax SRT-C SEC-300 column. The mobile phase was used as PBS, and the mobile solvent was eluted at 1 mL/min for 15 minutes. The ultraviolet detector was adjusted to 254 nm and the results were monitored by mAU. HMW is a high molecular weight species.

FIG. 9 is a result showing that the bispecific antibody related to the anti-mPDGFR-β antibody and cot-duo complexes according to the present invention inhibit angiogenesis in an oxygen-induced retinal disease animal model.

FIG. 10 shows that the bispecific antibody related with anti-mPDGFR-β antibody and cot-duo complexes according to the present invention inhibits angiogenesis in a laser-induced choroidal neovascularization animal model.

FIG. 11 is a result of SDS-polyacrylamide gel electrophoresis of a cotinine scFv-Cκ-scFv fusion protein as a bispecific antibody related with the anti-hPDGFR-β antibody according to the present invention: Lane 1, reduced PRb-CN16 x cotinine; Lane 2, non-reduced PRb-CN16 x cotinine; Lane 3, reduced PRb-CN26 x cotinine; Lane 4, non-reduced PRb-CN26 x cotinine; Lane 5, reduced PRb-CN32 x cotinine; Lane 6, non-reduced PRb-CN32 x cotinine; Lane 7, reduced anti-mCD154 x cotinine (control); Lane 8, non-reduced anti-mCD154 x cotinine (control); M, molecular weight marker.

In FIG. 12a, the bispecific antibodies of scFv-CκscFv fusion protein such as PRb-CN16 (●) PRb-CN32 (■), and PRb-CN26 (▲) and the negative control (♦), and cotinine scFv-Ck-ScFv fusion protein were reacted at various concentrations on hPDGFRβ chimera-coated microtiter plates. FIG. 12b is a result of reaction of HRP-anti-human Cκ antibody and TMB in each well, in which the results are shown as mean value±standard error from the duplicate experiments. In FIG. 12c, TNF-α receptor extracellular domain-human Fc fusion protein was used as a negative control antigen in an enzyme immunoassay. In FIG. 12d, in order to confirm the binding ability of the bispecific antibody related with the anti-hPDGFR-β antibody according to the present invention, the bispecific antibody scFv-Cκ-scFv fusion protein was cultured on a plate coated with cotinine-BSA, and was treated with HRP-conjugated anti-human Cκ antibody and TMB. In order to confirm the simultaneous binding of bispecific scFv-Cκ-scFv fusion proteins to cotinine and hPDGFRβ, hPDGFRβ-Fc chimera was cultured on microtiter wells coated with cotinine-BSA and was treated with HRP-conjugated anti-human Fc antibody, and TMB. The results are shown as the mean±SD from triplicate experiments. ***p<0.001 is compared to controls.

FIG. 13a to FIG. 13d are graphs confirming the competition and the cellular internalization of the bispecific antibody related with anti-hPDGFRβ according to the present invention with PDGF-BB. In FIG. 13a, bispecific scFv-Cκ-scFv fusion proteins were incubated on the hPDGFRβ-Fc chimera-coated microtiter plates without (left) or with (right) hPDGF-BB (100 nM), and the amount of bound bispecific antibody fusion protein was determined using HRP-conjugated anti-human Cκ antibody and TMB. In FIG. 13b, human pericyte cells expressing hPDGFR-β were treated with bispecific scFv-Cκ-scFv fusion proteins (100 nM) in flow cytometric assay buffer without or with hPDGF-BB-biotin. The cells were probed with APC-conjugated anti-human Cκ antibody and streptavidin-PE. Bispecific anti-mCD154 x cotinine scFv-Cκ-scFv fusion protein was used as a negative control. In FIG. 13c, the confocal microscopy visualized the internalization of bispecific scFv-Cκ-scFv fusion protein. After human pericyte cells were incubated with fusion proteins, surface-bound antibodies were removed. After cell fixation, the fusion proteins were stained with FITC-conjugated anti-human Cκ antibody (green). To image the early endosome, the cells were incubated with anti-Rab5 antibodies and Alexa Fluor 546-conjugated goat anti-rabbit IgG (red). The part indicated shows the enlarged part which shows co-localization of anti-hPDGFRβ x cotinine scFv-Cκ-scFv fusion proteins and early endosomes. DNA was stained with DAPI (blue). Images were merged after initial capture. Scale bar, 10 μm. FIG. 3d shows that assay was repeated with the addition of hPDGF-BB.

FIG. 14a and FIG. 14b are graphs showing that cytotoxicity assays of bispecific antibody related with anti-hPDGFRβ antibody according to the present invention complexed with cot-duo on PDGFRβ-expressing cells. In FIG. 14a, human pericyte cells were treated with the bispecific scFv-Cκ-scFv fusion protein and cot-duo complex. In FIG. 14b, the assay was repeated with the addition of hPDGF-BB. The cellular ATP levels were measured to determine relative cell viability. The bispecific anti-mCD154 x cotinine scFv-Cκ-scFv fusion protein was used as a negative control. DMSO was used as a vehicle control for cot-duo. Results are shown as the mean±SD from three repetitive experiments.

FIG. 15 is a graph showing Flow cytometry analysis on reactivity of bispecific antibody reacted with anti-hPDGFR-β antibody on the cells not expressing hPDGFR-β. A-431 cells were incubated with bispecific anti-hPDGFR-β x cotinine scFv-Cκ-scFv fusion proteins (100 nM) and probed with APC-conjugated anti-human Cκ antibody (clone TB28-2, BD Biosciences, San Jose, CA, USA).

FIG. 16 is a graph showing that cytotoxicity assays of bispecific antibody related with anti-hPDGFR-β antibody complexed with cot-duo complexes on the cells not expressing hPDGFR-β. A-431 cells were treated with anti-hPDGFR-β x cotinine fusion protein and cot-duo (DAR4). The cellular ATP levels were measured to determine relative cell viability. Bispecific anti-mCD154 x cotinine scFv-Cκ-scFv fusion protein was used as a negative control. DMSO was used as a vehicle control of cot-duo. Results are shown as the mean±SD acquired from three repetitive experiments.

FIG. 17 is a graph showing cross-species test of bispecific antibody related with anti-hPDGFR-β antibody. hPDGFR-β, mPDGFR-β, Rhesus PDGFRβ, Cynomolgus monkey PDGFRβ, Sus scrofa PDGFRβ and control Fc coated microtiter plates were incubated with bispecific antibody containing anti-hPDGFRβ antibody (100 nM) and the amount of bound bispecific fusion protein was determined using HRP-conjugated anti-human C<sub>κ</sub> antibody and TMB.

FIG. 18 shows that the bispecific antibody scFv-Cκ-scFv fusion protein (100 nM) in flow cytometry buffer was incubated on NIH3T3 cells expressing mPDGFR-β. The cells were treated with APC-anti human Cκ antibody. The bispecific antibody anti-HER2 x cotinine scFv-Cκ-scFv fusion protein was used as a negative control.

FIG. 19a to FIG. 19b are results confirming the competition for PRb-CN01 surrogate antibody. In FIG. 19a, various concentrations of PRb-CN01-rabbit Fc (0.01 nM-1 μM), PRb-CN01, anti-HER2 control antibody, and PRb-CN32 bispecific antibody scFv-Cκ-scFv (100 nM) diluted in 3% BSA/PBS were reacted on the plate coated with mPDGFR-β-hFc chimeric protein, and were reacted at each well at 37° C. for 2 hours. Then, the bound PRb-CN01-rabbit Fc protein was measured with HRP-anti rabbit Fc antibody and ABTS. In FIG. 19b, the mPDGFR-β-expressing NIH3T3 cells were reacted with PRb-CN01-rabbit Fc (50 nM) and PRb-CN01, a control antibody, and PRb-CN32 bispecific antibody scFv-Cκ-scFv (1 μM). The cells were incubated with FITC-anti rabbit Fc antibody. The bispecific antibody anti-HER2 x cotinine scFv-Cκ-scFv fusion protein was used as a negative control.

FIG. 20a to FIG. 20b are graphs confirming the difference in cytotoxic activity of PRb-CN01 and PRb-CN32 bispecific antibodies and cotinine-duocarmycin complexes in the cells expressing PDGFR-β. In FIG. 20a, NIH3T3 cells were treated with a bispecific antibody scFv-Cκ-scFv fusion protein and a cot-duo complex without mPDGF-BB. The cellular ATP was measured to assess relative cell viability. The bispecific antibody anti-HER2 x cotinine scFv-Cκ-scFv fusion protein was used as a negative control. In FIG. 20b, the experiment was repeated in the presence of mPDGF-BB.

MODE FOR INVENTION

The present invention will be described in more detail with reference to the following examples, but the scope of the present invention is not intended to be limited to the following examples.

Example 1. Expression and Purification of mPDGFR-β and Cκ Fusion Proteins

The extracellular region of mPDGFR-β is a peptide having an amino acid sequence of SEQ ID NO: 60 in the following table and a nucleotide sequence encoding it was prepared, and were chemically synthesized by adding a SfiI endonuclease recognition sites (GenScript Biotech, Jiangsu, China) to the end of the nucleotide. It was digested with SfiI enzyme and cloned into pCEP4 vector to prepare a recombinant pCEP4 expression vector, which was expressed by a previously reported method [Y. Lee, H. Kim et al., Exp. Mol. Med. 46 (2014) e114].

TABLE 3

| name | An amino acid sequence | SEQ ID NO |
|---|---|---|
| hPDGFR-β | MRLPGAMPALALKGELLLLSLLLLLEPQISQGLVVT PPGPELVLNVSSTFVLTCSGSAPVVWERMSQEPPQE MAKAQDGTFSSVLTLTNLTGLDTGEYFCTHNDSRG LETDERKRLYIFVPDPTVGFLPNDAEELFIFLTEITEI TIPCRVTDPQLVVTLHEKKGDVALPVPYDHQRGFS | 60 |

TABLE 3-continued

| name | An amino acid sequence | SEQ ID NO |
|---|---|---|
|  | GIFEDRSYICKTTIGDREVDSDAYYVRLQVSSINV SVNAVQTVVRQGENITLMCIVIGNEVVNFEWTYPR KESGRLVEPVTDFLLDMPYHIRSILHIPSAELEDSGT YTCNVTESVNDHQDEKAINITVVESGYVRLLGEVG TLQFAELHRSRTLQVVFEAYPPPTVLWFKDNRTLG DSSAGEIALSTRNVSETRYVSELTLVRVKVAEAGH YTMRAFHEDAEVQLSFQLQINVPVRVLELSESHPD SGEQTVRCRGRGMPQPNIIWSACRDLKRCPRELPPT LLGNSSEEESQLETNVTYWEEEQEFEVVSTLRLQH VDRPLSVRCTLRNAVGQDTQEVIVVPHSLPFK |  |
| mPDGFR-β | LVITPPGPEFVLNISSTFVLTCSGSAPVMWEQMSQV PWQEAAMNQDGTFSSVLTLTNVTGGDTGEYFCVY NNSLGPELSERKRIYIFVPDPTMGFLPMDSEDLFIFV TDVTETTIPCRVTDPQLEVTLHEKKVDIPLHVPYDH QRGFTGTFEDKTYICKTTIGDREVDSDTYYVYSLQ VSSINVSVNAVQTVVRQGESITIRCIVMGNDVVNFQ WTYPRMKSGRLVEPVTDYLFGVPSRIGSILHIPTAE LSDSGTYTCNVSVSVNDHGDEKAINISVIENGYVRL LETLGDVEIAELHRSRTLRVVFEAYPMPSVLWLKD NRTLGDSGAGELVLSTRNMSETRYVSELILVRVKV SEAGYYTMRAFHEDDEVQLSFKLQVNVPVRVLEL SESHPANGEQTIRCRGRGMPQPNVTWSTCRDLKRC PRKLSPTPLGNSSKEESQLETNVTFWEEDQEYEVVS TLRLRHVDQPLSVRCMLQNSMGGDSQEVTVVPHS LPFK | 61 |
| Cynomolgus Monkey PDGFR-β | MRLPGAMPALALKGQLLLLPLLLLLEPQVSQGLVI TPPGPELILNVSSTFVLTCSGSAPVVWERMSQELPQ EMAKAQDNTFSSVLTLTNLTGLDTGEYFCTYNDSR GLEPDERKRLYIFVPDPTVGFLPNDAEELFIFLTEITE ITIPCRVTDPQLVVTLHEKKGDIALPVPYDHQRGFS GIFEDRSYICKTTIGDREVDSDAYYVYRLQVSSINV SVNAVQTVVRQGENITLMCIVIGNEVVNFEWMYP RKESGRLVEPVTDFLLDMPYHIRSILHIPSAELEDSG TYTCNVTESVNDHQDEKAINITVVESGYVRLLGEV GALQFAELHRSRTLQVVFEAYPPPTVLWFKDNRTL GDSSAGEIALSTRNVSETRYVSELTLVRVKVAEAG HYTMRAFHEDAEVQLSFQLQINVPVRVLELSESHP DSGEQTVRCRGRGMPQPNIIWSACRDLKRCPRELP PMLLGNSSEEESQLETNVTYWEEEQEFEVVSTLRL QHVDRPLSVRCTLRNAVGQDMQEVIVVPHSLPFK | 62 |
| Sus scrofa PDGFR-β | MQLPRAVPASVLIGQVLLLPPLLLLGPQASWGLVIT PPGPELVLNLSSTFVLTCSGPAPVVWERMSQKPPQE MTGTQDGTFSSVLTLANVTGLDTGEYFCTYKGSPG LEASERKRLYIFVPDPAVGFLPVDPEELFIFLTEITAT TIPCRVTDPRLVVTLHEKKVDVPLPISYDHQRGFSG TFEDKTYVCKTTIGDREVDSDAYYVYSLQVSSINV SVGAVQTVVRQGENITVMCIVTGNEVVNFEWTYP RLETGRLVEPVTDFLFEMPHIRSILHIPSAELGDSGT YICNVSESVSDHRDEKAINVTVVESGYVRLIGELDA VQFAELHRSRTLQVVFEAYPPPTVIWFKDNRTLGD SGAGEIALSTRNVSETRYVSELTLVRVKVAEAGRY TMRAFHEDAEAQISFQLQVNVPVRVLELSESHPAS GEQTVRCRGRGMPQPHLTWSTCSDLKRCPRELPPT PLGNSSEEESQLETNVTYWPQEQEFEVVSTLRLRR VDQPLSVRCTLHNLLGHDAQEVTVVPHSLPFQ | 63 |

Specifically, the recombinant pCEP4 expression vector was transduced into human fetal kidney 293F cell line (Invitrogen, Carlsbad, CA, USA) by using polyethyleneimine (Polysciences, Warrington, PA, USA) according to the previously reported method [S. E. Reed et al., J. Vriol. Methods. 138 (2006) 85-98]. The transduced cells were cultured in GIBCO Freestyle 293 expression medium containing 10,000 IU/L of penicillin and 100 mg/L of streptomycin [S. Yoon et al., J. Cancer. Res. Clin. Oncol. 140 (2014) 227-33]. In six days after transduction, the culture supernatant was collected and mPDGFR-β-Cκ fusion protein was purified by affinity chromatography using KappaSelect resin (GE Healthcare, Buckinghamshire, UK) according to the manufacturer's instructions. In the fusion protein, the mPDGFR-β amino acid sequence is from Leu at $32^{nd}$ residue to Lys at $530^{th}$ residue of mPDGFR-β, which corresponds to the extracellular region, and is linked to Cκ at the C-terminus of the mPDGFR-β amino acid sequence through a linker-(GGGGS)3 (SEQ ID NO: 59).

Example 2. Expression and Purification of Bispecific Antibody (scFv-$C_\kappa$-scFv)

2-1. Preparation of Combinatorial scFv-Displayed Phage Library and Bio-Panning

Anti-mPDGFR-β antibodies were selected from a phage library expressing scFvs on the surface made from immunized chickens.

Chickens were immunized at total 4 times with the mPDGFR-β-Cκ fusion protein obtained in Example 1 above. Serum obtained from blood collection from wing veins before and during immunization was used to test the animal's immune state by using enzyme immunoassay and flow cytometry. One week after the fourth immunization, they were sacrificed, and the spleen, bursa of Fabricius, and bone marrow were harvested, and RNA was isolated using a TRI reagent (Invitrogen).

Using the isolated RNA as a template, cDNA was synthesized using Superscript® III First-Strand Synthesis system (Invitrogen), and then a phage library expressing scFv was produced according to the previously reported method [M. S. Lee et al., Hybridoma (Larchmt). 27 (2008) 18-24]. That is, four phage libraries expressing $7.5 \times 10^8$, $6.9 \times 10^8$, $2.1 \times 10^9$, and $2.2 \times 10^9$ scFv were prepared using the cDNA. The biopanning was performed at total five times on the magnetic beads to which mPDGFR-β-Cκ was bound with the library [Y. Lee et al., Exp. Mol. Med. 46 (2014) e114].

At the 5th output titer, scFv clones were randomly selected and phage enzyme immunoassay was performed on mPDGFR-β-Cκ-coated microtiter plates (3690; Corning Life Sciences, Corning, NY, USA) [C. F. Barbas III, D. R. Burton, J. K. Scott, G. J. Silverman, Phage display—a laboratory manual, Cold Spring Harbor Laboratory Press, New York, 2001].

Clones with binding capacity to mPDGFR-β-Cκ (A405>1.5) were asked Macrogen Inc. to perform sequence analysis with OmpSeq primers [W. Yang et al., Exp. Mol. Med. 49 (2017) e308]. After analyzing an amino acid sequence, a total of 9 types of antibody clones were found (Table 3). In consideration of the expression rate and binding ability, a total of four clones (PRb-CN01, PRb-CC01, PRb-CC02, PRb-CC03) were selected, and were performed for the subsequent experiments.

Table 4 below shows H-CDR3 amino acid sequence of anti-mPDGFR-β scFv clones. VH and VL and their CDR amino acid sequence information for the obtained four clones are shown in Table 1.

TABLE 4

| Clone | H-CDR3 sequences | SEQ ID NO |
|---|---|---|
| PRb-CN01 | GVGSWAHGGRIDA | 3 |
| PRb-CC01 | GGGSIDA | 11 |
| PRb-CC02 | GYAGTIDA | 19 |
| PRb-CC03 | SSYIDT | 27 |

2-2: Expression and Purification of a Bispecific Antibody (scFv-Cκ-scFv)

Using the anti-mPDGFR-β scFv clone prepared in Example 1, pCEP4 expression vector containing a gene encoding a (anti-mPDGFR-β scFv)-Cκ-(anti-cotinine scFv) bispecific antibody was prepared.

The specific structure of the prepared (anti-mPDGFR-β scFv)-Cκ-(anti-cotinine scFv) bispecific antibody and the binding positions of each linker are shown in FIG. 1a. Specifically, the anti-mPDGFR-β scFv and anti-cotinine scFv are each joined in the order of VL-GQSSRSSGGGGSSGGGGS (SEQ ID NO: 57 in Table 2)-VH from the N terminal, and that is, the C terminal of VL and the N terminal of VH are connected. From the N-terminus, anti-mPDGFR-β scFv, Ck and anti-cotinine scFv are linked using each linker, and the linker connecting the scFv is (GGGGS)3 of SEQ ID NO: 59 in Table 2, and Ck amino acids is shown in SEQ ID NO: 58 in Table 2.

As a specific method of preparing a fusion protein of a bispecific antibody, the gene encoding anti-mPDGFR-β scFv and the gene encoding anti-cotinine scfv were digested with SfiI, AgeI, and NotI (New England Biolabs) and ligated to the expression vector. The gene encoding the anti-mPDGFR-βscFv was linked from the N-terminus to the C-terminus in the order of VL-linker-VH in Table 1, and the linker was a peptide prepared by using the sequence of SEQ ID NO: 57 in Table 2, to obtain a nucleotide sequence encoding it. The gene encoding the anti-cotinine scfv was obtained based on the contents described in US8008448B, and the obtained amino acid sequence of the cotinine is shown in the following table.

TABLE 5

| Part | Amino acid sequence | SEQ ID NO |
|---|---|---|
| CDR1-VH | GHLRRRDWM | 64 |
| CDR2-VH | IGRSGDT | 65 |
| CDR3-VH | IPYFGWNNGDI | 66 |
| CDR1-VL | QSSQSPYSNEWLS | 67 |
| CDR2-VL | RISTLAS | 68 |
| CDR3-VL | AGGYNFGLFLFG | 69 |
| VH | EVQLVESGGGLVQPGGSLRLSCAASGHLRRR DWMNWVRQAPGKGLEWVAAIGRSGDTYYA TWAKGRFTISADTSKNTAYLQMNSLRAEDTA VYYCSRIPYFGWNNGDIWGQGTLVTVSS | 70 |
| VL | DIQMTQSPSSLSASVGDRVTITCQSSQSPYSNE WLSWYQQKPGKAPKLLIYRISTLASGVPSRFS GSRSGTDFTLTISSLQPEDFATYYCAGGYNFG LFLFGQGTKVEIK | 71 |

Trastuzumab scFv was cloned into an expression vector as a control for anti-mPDGFR-β scFv. Cysteine at the C-terminal portion of Cκ was excluded to remove the dimerization by disulfide bonds. After transducing the obtained DNA construct into HEK293F cells, a scFv-Cκ-scFv fusion protein was produced, and a bispecific antibody (scFv-Cκ-scFv) was purified by affinity chromatography using KappaSelect resin.

To confirm the protein purity of the expressed bispecific antibodies, SDS-polyacrylamide gel electrophoresis was performed using NuPage 4-12% Bis-Tris gel (Invitrogen) according to the manufacturer's instructions. 1 μg of protein was added to the LDS sample buffer with or without a reducing agent, and then reacted at 95° C. for 10 minutes.

Then, electrophoresis was performed, and the gel was stained with Ezway Protein-Blue II staining solution (Koma Biotech, Seoul, Korea) to visualize the protein. SDS-polyacrylamide gel electrophoresis was performed (FIG. 2). A photograph of the result of the electrophoresis is shown in FIG. 2.

As shown in FIG. 2, the protein reduced by using a reducing agent was 67 kDa, and the non-reduced protein was stained at 60 kDa. The molecular weight of the fusion protein calculated by using the computer was 66.77 kDa. No multimeric bands were seen. It was expected that the non-reduced protein moved faster than the reduced protein, because the non-reduced protein was less resistant to the movement on the gel due to its dense intrinsic morphology.

In SEC-HPLC (FIG. 8), which is a result of size exclusion chromatography of a bispecific antibody containing an antibody against mPDGFR-β according to an embodiment of the present invention, PRb-CC01, PRb-CC02, and PRb-CC03 all showed monomeric and trimeric bands unlike PRb-CN01. When their conjugates were formed with cot-duo, a large amount of high molecular weight species (HMWs) were observed in all of PRb-CC01, PRb-CC02, and PRb-CC03. In the case of PRb-CN01, little HMW was observed. Cot-duo-cot did not make HMWs for all four clones.

Example 3. Binding Affinity Analysis of Antibody to mPDGFR-β and Cotinine (Enzyme Immunoassays)

100 ng of mPDGFR-β-Fc chimera or TNF-α receptor extracellular domain-human Fc fusion protein contained in a coating buffer (0.1 M sodium bicarbonate, pH 8.6) was coated on a microtiter plate at 4° C. O/N. Each well was blocked with 150 μL of 3% (w/v) BSA (bovine serum albumin) in PBS as a blocking agent at 37° C. for 1 hour. Various concentrations (1:500-1:62,500) of chicken serum diluted in 3% BSA/PBS was treated and incubated at 37° C. for 2 hours. The microtiter plate was washed 3 times with 0.05% PBST, treated with horseradish peroxidase (HRP)-anti chicken IgY antibody (Millipore, Billerica, MA, USA), and incubated at 37° C. for 1 hour. The microtiter plate was once again washed with 0.05% PBST, and then cultured using 2,2'-azino-bis-3-ethylbenzothiazoline-6-sulfonic acid solutions (ABTS) (Pierce, Rockford, IL, USA). Then, the absorbance was measured at 405 nm with a Multiscan Ascent microplate instrument (Labsystems, Helsinki, Finland).

100 ng of mPDGFR-β-Fc chimera in the coating buffer or extracellular region of TNF-α receptor-human Fc fusion protein was coated on a microtiter plate at 4° C. O/N. Each well was blocked with 150 μL of 3% (w/v) BSA (bovine serum albumin) in PBS as a blocking agent at 37° C. for 1 hour. After treatment with various concentrations of bispecific antibodies (0.06 nM-1 μM) diluted in 3% BSA/PBS, they were incubated at 37° C. for 2 hours. The plate was washed 3 times with PBST and incubated for 1 hour at 37° C. using HRP-anti-human Cκ antibody (Millipore). After washing the plate 3 times with PBST, 3,3',5,5'-tetramethyl benzidine substrate solution (TMB) (GenDEPOT, Barker, TX, USA) was reacted. Then, the absorbance was measured at 650 nm with a Multiscan Ascent microplate instrument (Labsystems).

In order to confirm the competition between the bispecific antibody according to the present invention and mPDGF-BB, the microtiter plate was coated with mPDGFR-β-Fc chimera as mentioned above and then blocked. The microtiter plate was treated with various concentrations of the bispecific antibody (0.06 nM-1 μM) with or without addition of mPDGF-BB (100 nM), and then incubated at 37° C. for 2 hours. The washing, incubation, and detection were performed in the same manner as the enzyme immunoassay described above.

Enzyme immunoassay was performed to confirm the simultaneous binding ability of the bispecific antibody of scFv-Cκ-scFv fusion protein to mPDGFR-β and cotinine. The four kinds of bispecific antibodies did not bind to the control-human Fc protein (FIG. 3b), but bound to mPDGFR-β-Fc chimeric protein in a concentration-dependent manner (FIG. 3a).

The bispecific antibody containing the anti-mPDGFR-β antibody according to the present invention had a binding ability to cotinine-BSA, but no binding ability was observed in the case of anti-HER2 x cotinine scFv-Cκ-scFv fusion protein which was used as a control bispecific antibody (FIG. 3c).

In order to confirm whether the bispecific antibody has simultaneous binding ability to both cotinine and mPDGFR-β, anti-mPDGFR-β x cotinine scFv-Cκ-scFv fusion protein was reacted in wells coated with cotinine-BSA. Washing was performed for each process, and mPDGFR-β-Fc chimeric protein and HRP-anti human Fc antibody were sequentially incubated. Unlike other control groups, the four types of bispecific antibodies of scFv-Cκ-scFv (PRb-CC01, PRb-CN01, PRb-CC02, PRb-CC03) simultaneously bound to mPDGFR-β and cotinine (FIG. 3d).

A competition enzyme immunoassay was developed to examine the effect of mPDGF-BB on the binding ability of anti-mPDGFR-β x cotinine scFv-Cκ-scFv fusion protein. The serially diluted bispecific antibodies (anti-mPDGFR-β scFv-Cκ-cotinine scFv) were incubated on wells coated with mPDGFR-β-Fc chimeric fusion protein with or without mPDGF-BB. HRP-anti-human Cκ antibody was incubated and then TMB was added. The binding ability of PRb-CC01, PRb-CC02, and PRb-CC03 to mPDGFR-β was inhibited in the presence of mPDGF-BB (FIG. 4a). However, the binding ability of PRb-CN01 was not inhibited, so it confirmed that PRb-CN01 binds to mPDGFR-β in a noncompetitive manner to mPDGF-BB.

Example 4. Internalization Analysis of Antibody (Confocal Microscopy Analysis)

The bispecific antibody of scFv-Cκ-scFv fusion protein was analyzed with a confocal microscope for visualizing internalization. NIH3T3 cells were treated with the bispecific antibody of scFv-Cκ-scFv (10 μg/mL) diluted in DMEM containing 10% FBS, and internalized at 37° C. for 30 minutes. After washing the cells 3 times with cold PBS, acidic buffer (0.2 M acetic acid, 0.5 M sodium chloride) was treated at room temperature for 5 minutes to remove the antibody bound to the cell surface. Cells were washed twice with cold PBS, fixed with 4% paraformaldehyde for 10 minutes, and then subjected to immunofluorescence staining as previously described [J. M. Lim et al., J. Cell. Biol. 210 (2015) 23].

Briefly, to block antibodies having non-specific reaction, cells were incubated in PBS containing 5% horse serum and 0.1% Triton X-100 for 30 minutes, and 2 μg/mL FITC-anti human Cκ antibody (TB28-2, BD Biosciences) was added at room temperature for 30 minutes. To image the initial endosomes, the cells were washed 3 times with PBS, incubated with PBS containing 5% horse serum and 0.1% Triton X-100 for 30 minutes, and then incubated with ati-RabS antibody diluted to 1:200 (C8B1, Cell Signaling Technology, Danvers, MA, USA). Alexa Fluor 546 goat anti-rabbit IgG (A-11035, Invitrogen) was sequentially treated. Cells were treated with 0.2 µg/mL DAPI to detect DNA. Confocal microscopy images were obtained using a Zeiss LSM 880 microscope, and images were analyzed with Zen software (Carl Zeiss, Thornwood, NY, USA).

It was confirmed that three types of anti-mPDGFR-β x cotinine scFv-Cκ-scFv fusion proteins were internalized to cells through endosomes.

To measure the cellular internalization of the bispecific antibody of scFv-Cκ-scFv, anti-mPDGFR-β x cotinine scFv-Cκ-scFv fusion protein was incubated in NIH3T3 cells, and then treated with FITC-anti-human Cκ antibody and endosome-specific antibody. It was imaged using a confocal microscope. Intracellular fluorescence was detected fro only in cells cultured with PRb-CN01, PRb-CC02, and PRb-CC03 (FIG. 4c). PRb-CC01 was not internalized. When the images were merged, the present inventors confirmed that the fluorescence of the three antibody clones and the endosome-specific antibody were co-localized.

Example 5. Binding Ability Analysis of a Bispecific Antibody to mPDGFR-β and Cotinine (Flow Cytometry Analysis)

NIH3T3 cells were incubated with chicken serum diluted 1:100 in flow cytometry buffer (1% [w/v] BSA/PBS in 0.05% [w/v] sodium azide) at 4° C. for 1 hour and washed twice with flow cytometry buffer. The cells were treated with Alexa Fluor 488-anti chicken IgY antibody (703-545-155, Jackson Immunoresearch, West Grove, PA, USA) in flow cytometry buffer. After washing, it was classified and analyzed with a FACS Canto II instrument (BD Biosciences, San Jose, CA, USA). 10,000 cells were used for each measurement, and the results were analyzed by FlowJo (Tree Star, Ashland, OR, USA). The NIH3T3 cells were prepared by being purchased from Korea Cell Line Bank and incubated in Dulbecco's modified Eagle's medium (DMEM; Welgene, Seoul, Korea) with added by 10% fetal bovine serum (FBS; GIBCO, Grand Island, NY, USA), 1% penicillin, and streptomycin [S. Park et el., Exp. Mol. Med. 44 (2012) 554-61].

mPDGF-BB was biotinylated using a biotin-xx microscale protein labeling kit (Invitrogen) according to the manufacturer's instructions. NIH3T3 cells were cultured at 4° C. for 1 hour using the bispecific antibody of scFv-Cκ-scFv fusion protein (100 nM) under two different conditions with or without mPDGF-BB-biotin (100 nM). The cells were washed 4 times with flow cytometry buffer and cultured with allophycocyanin (APC)-anti-human Cκ antibody (clone TB28-2; BD Biosciences, San Jose, CA, USA) and streptavidin-phycoerythrin (PE) (12-4317-87; eBioscience, ThermoFisher). After washing, it was classified and analyzed with a FACS Canto II instrument (BD Biosciences, San Jose, CA, USA). 10,000 cells were used for each measurement, and the results were analyzed by FlowJo (Tree Star, Ashland, OR, USA). Like the result from the enzyme immunoassay method, only PRb-CN01 was bound to PDGFR-β present on the cell surface (FIG. 4B), when mPDGF-BB was added (FIG. 4b). The binding ability of the other three clones was inhibited by mPDGF-BB.

The present inventors tested the binding ability of the bispecific antibody of scFv-Cκ-scFv fusion proteins in MOLT-4 cells not expressing mPDGFR-β by flow cytometry analysis. MOLT-4 cells were cultured with a bispecific antibody of scFv-Cκ-scFv fusion protein (100 nM) at 4° C. for 1 hour. After washing as described above, the detection was conducted by treating with an APC-anti human Cκ antibody. The MOLT-4 cells were purchased from the Korea Cell Line Bank and prepared by culturing in RPMI-1640 (Welgene, Seoul, Korea) medium added by 10% fetal bovine serum, 1% penicillin, and streptomycin. It was confirmed that neither PRb-CN01 nor the anti-HER2 bispecific antibody of scFv-Cκ-scFv fusion antibody binds to the corresponding cells (FIG. 6).

Example 6. Complex Formation of Bispecific Antibody and Cotinine-Duocarmycin (Cot-Duo)

6-1: Cotinine-Duocarmycin Conjugate Synthesis

The present invention prepared valine-citrulline-PAB-duocarmycin, valine-citrulline-PAB-monomethyl auristatin E (MMAE) or valine-citrulline-PAB-mailimidomethyl cyclohexane-1-carboxial Rate (mcc) mertansine (DM1) which were conjugated with cotinine. In the present invention, as a result of testing the cotinine-cytotoxic drugs of DAR1 and DAR4, it was confirmed that the DAR4 cotinine-cytotoxic drug was more potent than DAR1, and also found that duocarmycin was the most potent when bound to cotinine. For this reason, cotinine-duocarmycin was used in the experiment.

Trans-4-cotinine carbonyl-(GSK)4 peptide was synthesized by Fmoc solid phase peptide synthesis 9SPSS using ASP48S auto peptide synthesizer in Peptron (Daejeon, Korea). Trans-4-cotinine carboxylic acid (Sigma-Aldrich, St Louis, MO, USA) was attached to the N-terminus of the peptide using the Fmoc-amino acid coupling method.

After the synthesis was completed, the crude product was separated from the resin by treating TFA/EDT/thioanisole/TIS/DW (90/2.5/2.5/2.5/2.5 volume) for 2 hours. The solution was precipitated by performing centrifugation using cold ether. The precipitates were air dried. The crude product was purified by reverse phase HPLC using an ACE 10 C18-300 reverse phase column (250 mm×21.2 mm, 10 µM). It was eluted with a water-acetonitrile linear gradient (10-75% (v/v) acetonitrile) containing 0.1% (v/v) trifluoroacetic acid (Alfa Aesar, Warm Hill, MA, USA). The purified peptide (Cot-(GSK)4 peptide) was collected and dried.

Valine-citrulline p-aminobenzyloxycarbonyl (PAB)-linked dimethylaminoethyl duocarmycin was linked to free four amino acids of lysine in cotinine-(GSK)4 by Levena Biopharma (San Diego, CA, USA). Cot-(GSK)4 peptide (3.5 mg, 2 µmol) was dissolved in acetonitrile/water (6/4, v/v, 1 mL). NHS ester of PAB-dimethylaminoethyl duocarmycin PEG3-valine-citrulline was added, and 9 µL of saturated aqueous NaHCO3 was sequentially added. The mixture was mixed at room temperature for 4 hours, and purified by reverse phase HPLC technique using a Phenomenex Gemini® C18-100 Å column (100 mm×2 mm×5 µM). The complex (cotinine-[GSK(duocarmycin]4, DAR4) was designated as "cot-duo". Bivalent-cotinine-(GSK)4K was linked to duocarmycin by the method described previously [J. Jin et al., Exp. Mol. Med. 50 (2018) 67]. Briefly, two trans-4-cotinine carboxylic acid molecules from Peptron were linked to the free amino acid at the N-terminus of GSKGSKGSKGSKK (SEQ ID NO: 74) and the epsilon amino acid at the C-terminus of lysine using a basic Fmoc-amino acid coupling method. In Levena Biopharma, four PAB-duocarmycins were linked with bivalent cotinine-GSKGSKGSKGSKK (SEQ ID NO: 74) peptides to form a complex named cotinine-[GSK(duocarmycin)]4K-cotinine (DAR2) or cot-duo-cot. FIG. 1a shows the fusion protein of the bispecific antibody and cotinine-duocarmycin conjugate (cot-duo, cot-duo-cot), and FIG. 1b shows the chemical structures of cot-duo and cot-duo-cot. "R" is valine-citrulline PAB-linked dimethyl aminoethyl duocarmycin.

6-2: Complex Formation with a Bispecific Antibody

Anti-PDGFR-β x cotinine scFv-Cκ-scFv fusion protein (15 μM) dissolved in PBS obtained in Example 2 was mixed at a ratio of 1:1 with cot-duo (15 μM) dissolved in DMSO, and mixed at a ratio of 2:1 with cot-duo-cot (7.5 μM). After 30 minutes of complex formation at room temperature, the complexes were diluted 5-fold in DMEM medium containing 10% FBS and 1% penicillin/streptomycin (25.6 pM-2 μM).

6-3: Confirmation of Complex Formation with a Bispecific Antibody

To confirm the complex formation, the (anti-mPDGFR-β scFv)-Cκ-(anti-cotinine scFv) of bispecific antibody and cotinine-duocarmycin conjugates prepared in Example 2 were analyzed by Y-Biologics (Daejeon, Korea) using size exclusion chromatography and HPLC.

For the analysis, a Dionex Ultimate 3000 (Thermo Fisher Scientific Inc., MA, USA) equipped with a Sepax SRT-C SEC-300 column (7.8×300 mm) filled with 300 Å-sized pores in 5 μm particles was used. The mobile phase was PBS (phosphate-buffered saline), and 20 μL of a sample (1 mg/mL) was injected, and the eluate was eluted at 1 mL/min for 15 minutes. The eluate from the column was monitored with an ultraviolet detector at 254 nm with mAU values.

FIG. 8 is a result of size exclusion chromatography of a bispecific antibody containing an anti-mPDGFR-β antibody according to the present invention. The bispecific antibodies, the complex of bispecific antibodies and cot-duo, the complex of bispecific antibodies and cot-duo-cot according to the present invention were analyzed with the size exclusion chromatography-HPLC using Dionex Ultimate 3000 equipped with a Sepax SRT-C SEC-300 column. The mobile phase was used as PBS, and the mobile solvent was eluted at 1 mL/min for 15 minutes. The ultraviolet detector was adjusted to 254 nm and the results were monitored by mAU. HMW is a high molecular weight species.

Example 7. Anti-Proliferative Analysis in PDGFR-β-Expressing Cell Lines (Cytotoxicity Test)

NIH3T3 cells were added to 50 μL of DMEM supplemented with 10% FBS and 1% penicillin/streptomycin, placed in a 96-well plate (CLS3595, Corning) and incubated overnight in 5% CO2 at 37° C. incubator. In each well containing 50 μL of cells, 50 μL of 50 anti-PDGFR-β x cotinine scFv-Cκ-scFv fusion protein (25.6 pM-2 μM) complexed with cot-duo or cot-duo-cot obtained in Experimental Example 10 was added and incubated for 72 hours in 5% CO2 at 37° C. incubator. To test mPDGF-BB on the toxic effect of the bispecific antibody of scFv-Cκ-scFv and the cotinine-duocarmycin complex, mPDGF-BB (2 nM) was added together with 50 μL of the bispecific antibody scFv-Cκ-scFv and the cotinine-duocarmycin complex. The mixed complexes were added to 50 μL of NIH3T3 cells.

The bispecific antibody of anti-HER2 x cotinine scFv-Cκ-scFv was used as a control. After 72 hours of incubation in the cells, 100 μL of Cell Titer-Glo reagents (Promega Corp., Madison, WI, USA) were added to all wells according to the manufacturer's instructions, and luminescence was measured in a luminometer (PerkinElmer, Waltham, MA, USA). The experiment was repeated 3 times. Relative viability was calculated with the following formula: [% viability=(luminescence of experimental well-luminescence of background well)/(luminescence of control-luminescence of background well)×100]. The wells containing only new medium were used as background wells.

It was confirmed that the complex of anti-mPDGFR-β x cotinine scFv-Cκ-scFv fusion antibody and cotinine duocarmycin (cot-duo, cot-duo-cot) had antiproliferative effects on mouse fibroblasts expressing PDGFR-β.

To evaluate the toxicity of the complex of anti-mPDGFR-B x cotinine scFv-Cκ-scFv bispecific antibodies and cotinine duocarmycin (cot-duo, cot-duo-cot), the complexes were added to NIH3T3 cells in the presence/absence of mPDGF-BB. The ATP of the cells was measured for relative cell viability. The toxicity of the bispecific antibody of scFv-Cκ-scFv fusion antibody was shown by $IC_{50}$ in Table 6 and FIG. 5. Table 6 below shows $IC_{50}$ of the in vitro titer and 95% confidence interval of the complex of the anti-mPDGFR-β x cotinine scFv-Cκ-scFv fusion antibody cotinine duocarmycin.

TABLE 6

| Bispecifi anti-mPDGFRβ x anti- | Cot-duo | | Cot-duo-cot | |
|---|---|---|---|---|
| cotinine scFv-Ck | IC50 (nM) | 95% Cl | IC50 (nM) | 95% Cl |
| PRB-CC01 | | | | |
| with mPDGF-BB | 27.1 | 19.1-38.5 | 67.2 | 52.0-86.9 |
| without mPDGF-BB | 25.0 | 18.1-34.7 | 87.6 | 54.4-141.1 |
| PRB-CN01 | | | | |
| with mPDGF-BB | 9.7 | 8.4-11.1 | 30.5 | 25.1-37.1 |
| without mPDGF-BB | 8.3 | 5.1-7.9 | 20.1 | 13.8-29.4 |
| Pb-CC02 | | | | |
| with mPDGF-BB | 20.6 | 16.2-26.3 | 89.0 | 54.2-57.9 |
| without mPDGF-BB | 20.1 | 15.2-26.5 | 125.4 | 47.4-328.7 |
| PRS-CC03 | | | | |
| with mPDGF-BB | 20.7 | 15.7-27.3 | 50.2 | 39.5-63.9 |
| without mPDGF-BB | 27.3 | 8.9-34.3 | 67.3 | 39.0-116.2 |
| Anti-HER2 | | | | |
| with mPDGF-BB | 23.2 | 17.4-31.0 | 60.8 | 48.4-78.4 |
| without mPDGF-BB | 36.7 | 27.9-48.3 | 93.7 | 55.3-155.9 |
| Cotinine duocarmycin conjugates | | | | |
| with mPDGF-BB | 22.3 | 16.8-31.4 | 56.7 | 44.3-72.6 |
| without mPDGF-BB | 15.5 | 11.7-20.3 | 45.4 | 29.8-83.2 |
| Free duocarmycin | | | | |
| with mPDGF-BB | 23.8 | 18.2-31.0 | 60.3 | 41.1-88.5 |
| without mPDGF-BB | 9.7 | 7.3-12.9 | 35.7 | 23.4-54.4 |

Of the four tested antibodies, PRb-CN01 showed the highest toxicity with or without mPDGF-BB, compared to the control group of anti-HER2 x cotinine scFv-Cκ-scFv ($p<0.01$; FIG. 5). PRb-CC02 and PRb-CC03 showed toxicity compared to the control antibody and the non-internalizing antibody (PRb-CC01), but did not show statistical significance. However, in the presence of mPDGF-BB, cotinine-duocarmycin was significantly more toxic than free duocarmycin, when complexed with PRb-CN01 ($p<0.01$). As a control experiment, the toxicity experiments were performed on MOLT-4 cells that do not express mPDGFR-β with the bispecific antibody of scFv-Cκ-scFv fusion protein and cot-duo complex. PRb-CN01 had no difference in toxicity from the control antibody of anti-HER2 x cotinine scFv-Cκ-scFv fusion protein (FIG. 7).

As shown in FIG. 5, scFv-Cκ-scFv did not kill the cells even when the antibody concentration increases, so the $IC_{50}$ value cannot be calculated. In table 6, the result of addition of cot-duo or cot-duo-cot together was indicated instead of $IC_{50}$ of scFv-Cκ-scFv alone. In addition, since MOLT-4 cells do not express mPDGFR-β, there is no difference in toxicity between the PRb-CN01-drug complex and the control antibody-drug complex.

Example 8. Analysis of Neovascularization In Vivo

It was confirmed that the complex of anti-mPDGFR-β x cotinine scFv-Cκ-scFv fusion antibody conjugated with cot-duo inhibited neovascularization in vivo.
8-1: Experiment of Animal with Oxygen-Induced Retinal Disease C57BL/6 mice on 7th day after birth were reared in a high-concentration oxygen (75%) chamber for 5 days, and transferred to a normal oxygen breeding facility on 12th day to create an environment for retinopathy of premature baby.

On the 14th day after birth, 1 uL of each bispecific antibody scFv-Cκ-scFv, and the complex of the bispecific antibody scFv-Cκ-scFv fusion protein and cot-duo were injected into the vitreous cavity at a concentration of 1 nM and 10 nM, respectively. To label blood vessels, isolectin B4-594 (1:100; 121413, Invitrogen) was treated on the retinal flat mount.

In an oxygen-induced retinal disease animal model, the complex of the PRb-CN01 x cotinine scFv-Cκ-scFv fusion antibody cot-duo inhibited neovascularization in a concentration-dependent manner (FIG. 9).
8-2: Laser-Induced Choroidal Neovascularization Animal Model After anesthetizing the mice, the retina of the mouse was irradiated with an indirect ophthalmoscope system (ILOODA) laser in a 300 um spot size with 400 mW intensity, 50 ms duration, and 810 nm wavelength to induce destruction of Bruch's membrane.

After 4 days of laser irradiation, 1 uL of each bispecific antibody scFv-Cκ-scFv, and complex of the bispecific antibody scFv-Cκ-scFv fusion protein and the cot-duo was injected into the vitreous cavity at a concentration of 10 nM. After 7 days of laser irradiation, the eyes were removed to obtain retinal pigment epithelial-choroid-scleral tissue, and immunofluorescence staining was performed with isolectin B4 antibody conjugated to Alexa Fluor 594 to determine the extent of the choroidal neovascular membrane. The neovascularization inhibition ability of the scFv-Cκ-scFv fusion protein and the cot-duo complex was confirmed. To quantitatively analyze the extent of the choroidal neovascular membrane, the ImageJ program (NIH) was used.

In the laser-induced choroidal neovascularization animal model, the PRb-CN01x cotinine scFv-Cκ-scFv fusion antibody cot-duo complex inhibited neovascularization (FIG. 10).

The toxicity of the bispecific antibody scFv-Cκ-scFv was calculated as $IC_{50}$ (50% of the maximum inhibitory ability), and statistics analysis were performed by unpaired Student's t-tests or one-way analysis of variance. Tukey's post hoc multiple comparison test was used to see the statistical significance of the bispecific antibodies scFv-Cκ-scFv. P-value of 0.05 or less was considered statistically significant. All analyzes were performed using Prism v5.0 (GraphPad Software, Inc., San Diego, CA, USA).

Example 9. Expression and Purification of hPDGFR-β-Cκ Fusion Protein

An amino acid sequences for the extracellular regions of hPDGFR-β, Cynomolgus monkey PDGFR-β, and Sus scrofa PDGFR-β are shown in SEQ ID NOs: 61, 62, and 63 in Table 3 above, but rhesus PDGFR-β is commercially available and purchased as the antigens (Cat: 90215-C02H). The prepared nucleotide sequences (Ginscript Biotag, Jangsuseong, China) were synthesized with addition of SfiI restriction recognition sequence at the end of the prepared nucleotide sequence, digested with SfiI enzyme, and cloned into pCEP4 vector. Then, the proteins were expressed in the form of Cκ or hFc according to the previously reported method [Y. Lee, H. Kim et al., Exp. Mol. Med. 46 (2014) e114, S. Park, D. Lee et al., Clin Chim Acta 411 (2010) 1238].

The proteins were transfected and purified according to the same method of mPDGFR-β in Example 1, but modified to purify the hFc fusion protein using Protein A gel affinity chromatography according to the manufacturer's instructions (Repligen Corp., Cambridge, MA). The fusion protein has a structure in which Cκ is linked to the C-terminus of an amino acid sequence hPDGFR-β through a linker-(GGGGS)3 (SEQ ID NO: 59).

Example 10. Expression and Purification of Bispecific Antibodies (scFv-Cκ-scFv)

10-1: Preparation of combinatorial scFv-displayed phage library and bio-panning according to the same method of Preparation of combinatorial scFv-displayed phage library and bio-panning in Example 2, an anti-hPDGFR-β scFv-expressing phage library was produced using the hPDGFR-β-Cκ fusion protein in Example 9 and was performed biopanning At the 5th output titer, scFv clones were randomly selected and phage enzyme immunoassay was performed on mPDGFR-β-Cκ-coated microtiter plates. After analyzing an amino acid sequence, all 3 types of antibody clones were identified (Table 7). Table 7 below shows the H-CDR3 sequences of anti-hPDGFR-β scFv clones. Table 2 shows the VH and VL and their CDR amino acid sequence information for the obtained three clones.

TABLE 7

| Clone | Amino acid sequence of VH-CDR3 | SEQ ID NO |
|---|---|---|
| PRb-CN16 | AAGTCYSHSCTGYIDA | 35 |
| PRb-CN32 | SAGSTYSYWDSDAGLIDA | 43 |
| PRb-CN26 | RGFMDAGGIDA | 51 |

10-2: Expression and Purification of a Bispecific Antibody scFv-Cκ-scFv Fusion Protein Using the anti-hPDGFR-β scFv clone prepared in Example 9, (anti-hPDGFR-β scFv)-Cκ-(anti-cotinine scFv) A pCEP4 expression vector containing a gene encoding a bispecific antibody was prepared according to the same method as the preparation of anti-mPDGFR-β scFv in Example 2.

The specific structure of the prepared (anti-hPDGFR-β scFv)-Cκ-(anti-cotinine scFv) bispecific antibody and the binding positions of each linker are shown in FIG. 1a. Specifically, the anti-hPDGFR-β scFv and anti-cotinine scFv are each joined in the order of VL-GQSSRSSGGGGSSGGGGS (SEQ ID NO: 57 in Table 2)-VH from the N terminal, and that is, the C terminal of VL and the N terminal of VH are connected. From the N-terminus, anti-hPDGFR-β scFv, Cκ and anti-cotinine scFv are linked using each linker, and the linker connecting the scFv is (GGGGS)3 of SEQ ID NO: 59 in Table 2, and Cκ amino acids is shown in SEQ ID NO: 58 in Table 2.

The specific method of preparing a fusion protein of a bispecific antibody, the purification and the purity measurement of the expressed bispecific antibodies were performed in the substantially same method of Example 2. The result of SDS-polyacrylamide gel electrophoresis is shown in FIG. 11. FIG. 11 is a result of SDS-polyacrylamide gel electrophoresis of a cotinine scFv-Cκ-scFv fusion protein as a bispecific antibody against the anti-hPDGFR-β according to the present invention.

As shown in FIG. 11, the protein reduced using a reducing agent at lane 1 (PRb-CN16 x cotinine bispecific antibody), lane 3 (PRb-CN26 x cotinine bispecific antibody) and lane 5 (PRb-CN32 x cotinine bispecific antibody) was stained at 69.0 kDa, the reduced protein was stained at 67 kDa, and the non-reducing protein was stained at 60 kDa. The computer-calculated fusion protein size was 66.77 kDa. No multimeric bands were observed.

Example 11. Binding Affinity Analysis of Bispecific Antibodies to hPDGFR-β and Cotinine 100 ng of hPDGFR-β-Fc chimera or TNF-α receptor extracellular domain-human Fc fusion protein contained in a coating buffer (0.1 M sodium bicarbonate, pH 8.6) was coated on a microtiter plate at 4° C. O/N. Each well was blocked with 150 µL of 3% (w/v) BSA (bovine serum albumin) in PBS as a blocking agent at 37° C. for 1 hour. Various concentrations (1:500-1:62,500) of chicken serum diluted in 3% BSA/PBS was treated and incubated at 37° C. for 2 hours, and analyzed according to the same method of the protocol for testing the anti-mPDGFR-β immune chicken serum binding ability.

100 ng of hPDGFR-β-Fc chimera in the coating buffer or extracellular region of TNF-α receptor-human Fc fusion protein was coated on a microtiter plate at 4° C. O/N. Each well was blocked with 150 µL of 3% (w/v) BSA (bovine serum albumin) in PBS as a blocking agent at 37° C. for 1 hour. After treatment with various concentrations of bispecific antibodies of scFv-Cκ-scFv fusion protein (0.01 nM-1 µM), the analysis was performed in the same protocol of the concentration-dependent binding ability of anti-mPDG-FRR-β scFv-Cκ-scFv fusion protein.

In order to confirm the competition between the bispecific antibody scFv-Cκ-scFv and hPDGF-BB, as in Example 3, hPDGFR-β-Fc chimera was coated on a microtiter plate and then blocked. The microtiter plate was treated with various concentrations of the bispecific antibody (0.01 nM-1 µM) with or without addition of hPDGF-BB (100 nM; 220-BB; R&D systems), and then incubated at 37° C. for 2 hours. The washing, incubation, and detection were performed in the same manner as the enzyme immunoassay described above. The binding ability of PRb-CN16, PRb-CN32, and PRb-CN26 to hPDGFR-β was not inhibited in the presence of hPDGF-BB (FIG. 12a).

100 ng of hPDGFR-β, mPDGFR-β, rhesus PDGFR-β (90215-C02H, Sino Biological Inc. Beijing, China), cynomolgus monkey PDGFR-β, Sus scrofa PDGFR-β-Fc chimera or TNF-α receptor extracellular domain-human Fc fusion protein was coated with 4° C. temperature O/N. After blocking the wells, sequential culture of the anti-hPDGFR-β scFv-Cκ-scFv fusion protein and the HRP conjugated anti-human Cκ antibody was followed in the same manner as in Example 3.

Enzyme immunoassay was performed to confirm the simultaneous binding ability of the bispecific antibody of scFv-Cκ-scFv fusion protein to hPDGFR-β and cotinine. The four kinds of bispecific antibodies did not bind to the control-human Fc protein (FIG. 12b), but bound to hPDGFR-β-Fc chimeric protein in a concentration-dependent manner (FIG. 12a).

Both the anti-hPDGFR-β x cotinine scFv-Cκ-scFv fusion protein and the control bispecific antibody of anti-mCD154 x cotinine scFv-Cκ-scFv fusion protein had the binding ability to cotinine-BSA (FIG. 12c). In order to determine of the simultaneous binding ability of cotinine and hPDGFR-β, an anti-hPDGFR-β x cotinine scFv-Cκ-scFv fusion protein was cultured in wells coated with cotinine-BSA. Washing was performed for each process, and hPDGFR-β-Fc chimeric protein and HRP-anti human Fc antibody were incubated in order. The three kinds of bispecific antibody scFv-Cκ-scFv fusion proteins simultaneously bound to hPDGFR-β and cotinine (FIG. 12d).

It was confirmed that the anti-hPDGFR-β x cotinine scFv-Cκ-scFv fusion protein could simultaneously bind to hPDGFR-β and cotinine even in the presence of hPDGF-BB (FIG. 13a).

Enzyme immunoassay was used to test the cross-species binding of the anti-hPDGFR-β x cotinine scFv-Cκ-scFv fusion protein. All three clones except the control x cotinine scFv-Cκ-scFv fusion protein successfully bound to hPDGFR-β, mPDGFR-β, Rhesus PDGFR-β, Cynomolgus monkey PDGFR-β, and Sus scrofa PDGFR-β (FIG. 17).

FIG. 17 is a graph showing an experiment of the cross-species reaction of the bispecific antibody against the anti-hPDGFR-β antibody according to the present invention. On the microtiter plates coated with hPDGFR-β, mPDGFR-β, Rhesus PDGFR-β, Cynomolgus monkey PDGFR-β, Sus scrofa PDGFR-β and control Fc coated, the bispecific antibody containing anti-hPDGFR-β antibody according to the present invention (100 nM) was reacted and the amount of bound bispecific antibody was measured using HRP conjugated anti-human Cκ antibody and TMB.

Example 12. Internalization Analysis of Bispecific Antibody

Human pericyte cells were treated with the diluted bispecific antibody scFv-Cκ-scFv (10 µg/mL) in pericyte growth medium supplemented with 10% FBS, and internalized at 37° C. for 30 minutes. The analysis was performed in the same manner according to the protocol of the confocal microscope of the anti-mPDGFR-β x cotinine scFv-Cκ-scFv fusion protein of Example 4. After the addition of hPDGF-BB (50 ng/mL) to the bispecific antibody scFv-Cκ-scFv fusion protein, the confocal microscopy experiments were performed according to the same protocol.

It was confirmed that the anti-hPDGFR-β x cotinine scFv-Cκ-scFv fusion protein was internalized to cells through endosomes.

The internalization of the bispecific antibody scFv-Cκ-scFv fusion protein was visualized. After treatment of human pericyte cells with the fusion protein, antibodies bound to the cell surface were removed. After cell fixation, the fusion protein was stained with FITC-anti human Cκ antibody (green). To visualize early endosomes, the cells were stained with anti-Rab5 antibody and Alexa Fluor 546-goat anti-rabbit antibody IgG (red). The part indicated by the arrow shows the enlarged part in which the fluorescence of the anti-hPDGFR-β x cotinine scFv-Cκ-scFv fusion protein and the initial endosome were co-localized. DNA was stained with DAPI (blue)(Scale bar, 10 µm). FIG. 13d was repeated with hPDGF-BB.

To measure the cellular internalization of the bispecific antibody of scFv-Cκ-scFv, anti-hPDGFR-β x cotinine scFv-Cκ-scFv fusion protein was incubated in human pericyte cells, and then treated with FITC-anti-human Cκ antibody and endosome-specific antibody. It was imaged using a confocal microscope. Intracellular fluorescence was detected from only in cells cultured with PRb-CN32 and PRb-CN16 (FIG. 13c). When the images were merged, the present inventors confirmed that the fluorescence of the two antibody clones and the endosome-specific antibody were co-localized. When PRb-CN32, PRb-CN16, and PRb-CN26 were treated with hPDGF-BB, they were co-localized with endosome-specific antibody (FIG. 13d). PRb-CN26 was internalized in a large amount within 30 minutes when PDGF-BB was treated together. Internalization of the antibody is very important for delivery of drug into the target cell. In case that the level of PDGF-BB was elevated in some diseases, even increased the level of PDGF-BB did not affect the internalization of the antibody according to the present invention. Therefore, it is useful for intracellular delivery of drug to patients with diseases.

Example 13. Binding Ability Analysis of a Bispecific Antibody to hPDGFR-β and Cotinine Human pericyte cells were incubated with chicken serum diluted 1:100 in flow cytometry buffer (1% [w/v] BSA/PBS in 0.05% [w/v] sodium azide) at 4° C. for 1 hour and washed four times with flow cytometry buffer. The experiment followed the same protocol of that testing anti-mPDGFR-β in Example 4, The human percyte cells were prepared by being purchased from PromoCell (Heidelberg, Germany) and cultured in Dulbecco's modified Eagle's medium (DMEM; Welgene, Seoul, Korea) supplemented with 10% fetal bovine serum (FBS; GIBCO, Grand Island, NY, USA), 1% penicillin, and streptomycin [S. Park et el., Exp. Mol. Med. 44 (2012) 554-61].

Human pericyte cells were cultured at 4° C. for 1 hour using the bispecific antibody of scFv-Cκ-scFv fusion protein (100 nM) under two different conditions with or without hPDGF-BB-biotin (100 nM, BT220; R&D systems). The cells were washed 4 times with flow cytometry buffer and cultured with allophycocyanin (APC)-anti-human Cκ antibody (clone TB28-2; BD Biosciences, San Jose, CA, USA) and streptavidin-phycoerythrin (PE) (12-4317-87; eBioscience, ThermoFisher). After washing, it was classified and analyzed with a FACS Canto II instrument (BD Biosciences, San Jose, CA, USA). 10,000 cells were used for each measurement, and the results were analyzed by FlowJo (Tree Star, Ashland, OR, USA).

The bispecific antibody scFv-Cκ-scFv fusion protein (100 nM) was incubated at 4° C. for 1 hour in A-431 cells. After washing as described above, the detection was conducted by treatment with an APC-anti human Cκ antibody. The A-431 cells were purchased from the Korea Cell Line Bank and cultured in Dulbecco's modified Eagle's medium (DMEM; Welgene, Seoul, Korea) medium containing 10% fetal bovine serum (GIBCO), 1% penicillin, and streptomycin.

The present inventors tested the binding ability of each clone in human pericyte cells in the presence of hPDGF-BB by flow cytometry analysis, and confirmed that anti-hPDGFR-β x cotinine scFv-Cκ-scFv fusion protein and hPDGF-BB-biotin bound to the cells. When hPDGF-BB was added, all three clones were bound to PDGFR-β present on the cell surface, which was similar to that of the enzyme immunoassay method (FIG. 13b). The present inventors confirmed the binding ability of the bispecific antibody scFv-Cκ-scFv fusion proteins to A-431 cells that do not express hPDGFR-β by flow cytometry, and that all of the anti-hPDGFR-β x cotinine scFv-Cκ-scFv fusion proteins and the control bispecific antibody of anti-mCD154 x cotinine scFv-Cκ-scFv fusion protein did not bind to the corresponding cells (FIG. 15).

Example 14. Complex Formation of Bispecific Antibody and Cotinine-Duocarmycin (Cot-Duo)

The experiment was performed in the substantially same method of Example 6, except that the bispecific antibody containing the anti-mPDGFR-β antibody, a bispecific antibody related to the anti-hPDGFR-β antibody prepared in Example 10 was used. As described in the preparation and transduction of the anti-mPDGFR-β x cotinine scFv-Cκ-scFv fusion protein in Example 6, HEK293F cells were transduced in the same manner. The bispecific antibody of scFv-Cκ-scFv fusion protein was purified from the supernatant by affinity chromatography and subjected to SDS-polyacrylamide gel electrophoresis (FIG. 11).

Example 15. Anti-Proliferative Analysis in PDGFR-β-Expressing Cell Lines (Cytotoxicity Test)

Human pericyte cells were added to 50 μL of DMEM supplemented with 10% FBS and 1% penicillin/streptomycin, placed in a 96-well plate (CLS3595, Corning) and incubated overnight in 5% CO2 at 37° C. incubator. In each well containing 50 μL of cells, 50 μL of 50 anti-hPDGFR-β x cotinine scFv-Cκ-scFv fusion protein (25.6 pM-2 μM) complexed with cot-duo was added and incubated for 72 hours in 5% CO2 and 37° C. incubator.

To evaluate the effect of hPDGF-BB on the toxicity of the complex of the bispecific antibody of scFv-Cκ-scFv and cot-duo, hPDGF-BB (2 nM) was added together with 50 μL of the bispecific antibody scFv-Cκ-scFv and cot-duo complex. The mixed complexes were added to 50 μL of cell-containing solution. The bispecific antibody anti-mCD154 x cotinine scFv-Cκ-scFv was used as a control. Other experimental methods were carried out in the same manner as in the protocol of the anti-mPDGFR-β x cotinine scFv-Cκ-scFv fusion protein in Example 7.

In order to evaluate the toxicity of the anti-hPDGFR-β x cotinine scFv-Cκ-scFv fusion protein and cot-duo complexes, the complex was treated in human pericyte cells with or without hPDGF-BB, and the cells were treated with adenosine triphosphate to measure the relative viability. The toxicity of the bispecific antibody of anti-hPDGFR-β x cotinine scFv-Cκ-scFv fusion protein and cot-duo complex was shown by $IC_{50}$ (Table 8). Table 8 below showed in vitro titer with 95% confidence interval of the complex of the anti-mPDGFR-β x cotinine scFv-Cκ-scFv fusion antibody and cotinine duocarmycin.

TABLE 8

| anti-hPDGFRβ x anti-cotinine scFv-Ck-scFv | Cot-duo | |
|---|---|---|
| | IC50 (nM) | 95% Cl |
| PRb-CN16 | | |
| Without hPDGF-BB | 2.39 | 2.12-2.71 |
| With hPDGF-BB | 1.82 | 1.58-2.10 |

TABLE 8-continued

| anti-hPDGFRβ x anti-cotinine scFv-Cκ-scFv | IC50 (nM) | 95% CI |
|---|---|---|
| PRb-CN32 | | |
| Without hPDGF-BB | 0.78 | 0.75-0.81 |
| With hPDGF-BB | 0.87 | 0.58-0.76 |
| PRb-CN26 | | |
| Without hPDGF-BB | 0.90 | 0.84-0.98 |
| With hPDGF-B8 | 0.87 | 0.78-0.96 |
| Control | | |
| Without hPDGF-BB | 4.47 | 6.73-13.87 |
| With hPDGF-BB | 3.48 | 3.05-3.97 |
| Without hPDGF-BB | 13.70 | 12.58-14.93 |
| With hPDGF-BB | 12.42 | 10.42-14.80 |

As shown in the results of Table 8, all of three tested antibodies (PRb-CN16, PRb-CN32, PRb-CN26) showed higher toxicity than control anti-mCD154 x cotinine scFv-Cκ-scFv with or without hPDGF-BB ($p<0.05$; FIG. 14a and FIG. 14b). As a control experiment, the toxicity experiments were performed on A-431 cells that did not express hPDGFR-β, with the bispecific antibody scFv-Cκ-scFv fusion protein and cot-duo complex. All of the anti-hPDGFR-β x cotinine scFv-Cκ-scFv fusion proteins had not higher toxicity than the control antibody anti-mCD154 x cotinine scFv-Cκ-scFv fusion protein (FIG. 16). Therefore, as a result of anti-proliferative analysis result, the bispecific antibody/cot-duo complex had higher cytotoxicity in the human pericyte cell lines expressing hPDGFR-β, compared to the control anti-mCD154 x cotinine scFv-Cκ-scFv, but there was no difference in cytotoxicity in A-431 not expressing hPDGFR-β, compared to the control anti-mCD154 x cotinine scFv-Cκ-scFv. This cytotoxicity result is caused by the efficacy of duocarmycin delivered by hPDGFR-β, which suggests the bispecific antibody scFv-Cκ-scFv effectively delivers the hapten-drug (cot-duo) to target cells and effectively releases drugs intracellularly.

Example 16

First, using the PRb-CN01 scFv prepared in Example 2, a pCEP4 expression vector containing a gene encoding scFv-rabbit Fc antibody was constructed. An amino acid sequence of the rabbit Fc antibody used in the experiment is shown in SEQ ID NO: 72 in the sequence listing.

Specifically, it was linked to the rabbit Fc using a hinge (QEPKSSDKTHTSPPSP: SEQ ID NO: 73) at the C-terminus of the anti-mPDGFR-β scFv. As a specific method for preparing scFv-rabbit-Fc, the gene encoding anti-mPDGFR-β was digested with SfiI (New England Biolabs) and ligated to an expression vector. Transfection and purification were performed according to the method for mPDGFR-β in the Examples, but it was modified to purify the rabbit Fc fusion protein using Protein A gel affinity chromatography according to the manufacturer's instructions (Repligen Corp., Cambridge, MA).

By performing substantially the same method as the flow cytometry for antibody binding ability of Example 5, it was confirmed that both PRb-CN01 and PRb-CN32 bispecific antibodies scFv-Cκ-scFv bound to NIH3T3 cells (FIG. 18). Specifically, the bispecific antibody scFv-Cκ-scFv fusion protein (100 nM) in flow cytometry buffer was cultured on NIH3T3 cells expressing mPDGFR-β. The cells were treated with APC-anti human Cκ antibody. The bispecific antibody anti-HER2 x cotinine scFv-Cκ-scFv fusion protein was used as a negative control.

It was carried out in substantially the same manner as the enzyme immunoassay method for antibody binding ability of Example 3, except that mPDGFR-β-hFc chimeric protein was coated with O/N on a microtiter plate at a temperature of 4° C. After incubating the blocking agent in each well, various concentrations of PRb-CN01-rabbit Fc (0.01 nM-1 μM) and PRb-CN01, control anti-HER2 antibody, and PRb-CN32 bispecific scFv-Cκ-scFv (100 nM) diluted in 3% BSA/PBS were reacted in each well at 37° C. for 2 hours. After washing the plate three times with PBST, the HRP-anti rabbit Fc antibody was reacted at 37° C. for 1 hour, and after washing, the reaction was performed using ABTS. Then, the absorbance was measured at 405 nm with a Multiscan Ascent microplate device (Labsystems, Helsinki, Finland) (FIG. 19A). FIG. 19a is the result of confirming the competition for the PRb-CN01 surrogate antibody. As shown in FIG. 19a, the binding ability of mPDGFR-β-hFc chimeric protein and PRb-CN01-rabbit Fc was inhibited by PRb-CN01 and PRb-CN32 bispecific scFv-Cκ-scFv.

According to the same manner as in Example 5, PRb-CN01-rabbit Fc (50 nM) and PRb-CN01, control antibody, PRb-CN32 bispecific antibody scFv-Cκ-scFv (1 μM) were cultured on NIH3T3 cells for 1 hour. After washing, it was reacted with FITC-anti rabbit Fc antibody (172-1506, KPL, Gaithersburg, Maryland, USA) at 4° C. for 1 hour. After washing, it was classified and analyzed with a FACS Canto II instrument (BD Biosciences, San Jose, CA, USA). 10,000 cells were identified for each measurement. The results were analyzed by FlowJo (Tree Star, Ashland, OR, USA) (FIG. 19b).

As shown in FIG. 19b, the binding ability of mPDGFR-β and PRb-CN01-rabbit Fc present on the cell surface was inhibited by the PRb-CN01 and PRb-CN32 bispecific antibody scFv-Cκ-scFv.

It was carried out in the same manner as in Example 7, except that the bispecific antibody related with the anti-mPDGFR-β antibody and the bispecific antibody related with the anti-hPDGFR-β antibody prepared in Example 10 were used. FIG. 20a to FIG. 20b are graphs showing the difference in cytotoxic activity of PRb-CN01 and PRb-CN32 bispecific antibodies and cotinine-duocarmycin complexes in the cells expressing PDGFR-β. In FIG. 20b, an experiment was repeated in the presence of mPDGF-BB.

As shown in FIG. 20a and FIG. 20b, both of the two tested antibodies (PRb-CN01, PRb-32) showed the equivalent cytotoxicity regardless of the presence/absence of mPDGF-BB. Therefore, it was confirmed that PRb-CN01 and PRb-32 are surrogate antibodies.

The invention claimed is:

1. An anti-PDGF receptor antibody or antigen-binding fragment thereof that specifically binds to platelet-derived growth factor receptor beta (PDGFR-β) comprising a heavy chain variable region and a light chain variable region,
Wherein the anti-PDGF receptor antibody or antigen-binding fragment thereof comprises
   a) HCDRs comprising the amino sequences of SEQ ID NO: 1, 2 and 3 and LCDRs comprising the amino sequences of SEQ ID NO: 4, 5 and 6
   b) HCDRs comprising the amino sequences of SEQ ID NO: 9, 10 and 11 and LCDRs comprising the amino sequences of SEQ ID NO: 12, 13 and 14
   c) HCDRs comprising the amino sequences of SEQ ID NO: 17, 18, 19 and LCDRs comprising the amino sequences of SEQ ID NO: 20, 21 and 22
   d) HCDRs comprising the amino sequences of SEQ ID NO: 25, 26, 27 and LCDRs comprising the amino sequences of SEQ ID NO: 28, 29 and 30
   e) HCDRs comprising the amino sequences of SEQ ID NO: 33, 34 and 35 and LCDRs comprising the amino sequences of SEQ ID NO: 36, 37 and 38
   f) HCDRs comprising the amino sequences of SEQ ID NO: 41, 42 and 43 and LCDRs comprising the amino sequences of SEQ ID NO: 44, 45 and 46 or
   g) HCDRs comprising the amino sequences of SEQ ID NO: 49, 50 and 51 and LCDRs comprising the amino sequences of SEQ ID NO: 52, 53 and 54.

2. The anti-PDGF receptor antibody or antigen-binding fragment thereof according to claim 1, wherein the anti-PDGF receptor antibody or antigen-binding fragment thereof specifically binds to an extracellular region of PDGFR-β.

3. The anti-PDGF receptor antibody or antigen-binding fragment thereof according to claim 1, wherein the anti-PDGF receptor antibody or antigen-binding fragment thereof binds non-competitively with PDGF-BB.

4. The anti-PDGF receptor antibody or antigen binding fragment thereof according to claim 3, wherein the anti-PDGF receptor antibody or antigen-binding fragment thereof comprises:
   a) HCDRs comprising the amino sequences of SEQ ID NO: 1, 2 and 3 and LCDRs comprising the amino sequences of SEQ ID NO: 4, 5 and 6
   b) HCDRs comprising the amino sequences of SEQ ID NO: 33, 34 and 35 and LCDRs comprising the amino sequences of SEQ ID NO: 36, 37 and 38
   c) HCDRs comprising the amino sequences of SEQ ID NO: 41, 42 and 43 and LCDRs comprising the amino sequences of SEQ ID NO: 44, 45 and 46 or
   d) HCDRs comprising the amino sequences of SEQ ID NO: 49, 50 and 51 and LCDRs comprising the amino sequences of SEQ ID NO: 52, 53 and 54.

5. The anti-PDGF receptor antibody or antigen binding fragment thereof according to claim 1, wherein the anti-PDGF receptor antibody or antigen-binding fragment thereof is internalized by a cell expressing PDGFR-β.

6. The anti-PDGF receptor antibody or antigen binding fragment thereof according to claim 5, wherein
   a) HCDRs comprising the amino sequences of SEQ ID NO: 1, 2 and 3 and LCDRs comprising the amino sequences of SEQ ID NO: 4, 5 and 6
   b) HCDRs comprising the amino sequences of SEQ ID NO: 17, 18, 19 and LCDRs comprising the amino sequences of SEQ ID NO: 20, 21 and 22
   c) HCDRs comprising the amino sequences of SEQ ID NO: 25, 26, 27 and LCDRs comprising the amino sequences of SEQ ID NO: 28, 29 and 30
   d) HCDRs comprising the amino sequences of SEQ ID NO: 33, 34 and 35 and LCDRs comprising the amino sequences of SEQ ID NO: 36, 37 and 38
   e) HCDRs comprising the amino sequences of SEQ ID NO: 41, 42 and 43 and LCDRs comprising the amino sequences of SEQ ID NO: 44, 45 and 46 or
   f) HCDRs comprising the amino sequences of SEQ ID NO: 49, 50 and 51 and LCDRs comprising the amino sequences of SEQ ID NO: 52, 53 and 54.

7. The anti-PDGF receptor antibody or antigen-binding fragment thereof according to claim 1, wherein the anti-PDGF receptor antibody is an intact antibody in the form of IgG1, IgG2, IgG3 or IgG4.

8. The anti-PDGF receptor antibody or antigen binding fragment thereof according to claim 1, wherein the antigen-binding fragment of antibody is selected from the group consisting of scFv, (scFv)$_2$, scFv-Fc, Fab, Fab' and F(ab')$_2$.

9. The anti-PDGF receptor antibody or antigen-binding fragment thereof according to claim 8, wherein the antigen-binding fragment of antibody is a scFv comprising a light chain variable region (VL), a linker, and a heavy chain variable region (VH) sequentially from N-terminal to C-terminal direction.

10. The anti-PDGF receptor antibody or antigen-binding fragment thereof according to claim 8, wherein the anti-PDGF receptor antibody or antigen-binding fragment thereof is conjugated with a chemotherapeutic drug, a hapten, an enzyme, a peptide, an aptamer, a toxin, an affinity ligand, or a detection label.

11. The anti-PDGF receptor antibody or antigen-binding fragment thereof according to claim 10, wherein the hapten specifically binds to PDGFR-β.

12. The anti-PDGF receptor antibody or antigen-binding fragment thereof according to claim 10, wherein the hapten is cotinine, DNP (2,4-dinitrophenol), TNP (2,4,6-trinitrophenol), biotin, or digoxigenin.

13. The anti-PDGF receptor antibody or antigen-binding fragment thereof according to claim 10, wherein the hapten is bound to a chemotherapeutic drug.

14. A bispecific antibody, comprising the anti-PDGF receptor antibody or antigen-binding fragment thereof according to claim 1 which specifically binds to platelet-derived growth factor receptor beta (PDGFR-β), and an antibody or antigen-binding fragment thereof against hapten for a chemotherapeutic drug.

15. The bispecific antibody according to claim 14, comprising an antigen-binding fragment of an anti-PDGF receptor antibody, and an antigen-binding fragment of an antibody binding to a hapten.

16. The bispecific antibody according to claim 15, wherein a scFv of the anti-PDGF receptor antibody and a scFv of the antibody against a hapten for a chemotherapeutic drug are connected directly or through a first linker.

17. The bispecific antibody of claim 16, wherein C-terminus of the scFv of the anti-PDGF receptor antibody and N-terminus of the scFv of the antibody against the hapten for a chemotherapeutic drug are connected through a first linker.

18. The bispecific antibody of claim 17, wherein the scFv of the anti-PDGF receptor antibody in which a heavy chain variable region and a light chain variable region of the anti-PDGF receptor antibody are connected through a second linker, and the scFv in which a heavy chain variable region and a light chain variable region of the anti-hapten antibody are connected through a third linker are connected with the first linker,
  a) HCDRs comprising the amino sequences of SEQ ID NO: 1, 2 and 3 and LCDRs comprising the amino sequences of SEQ ID NO: 4, 5 and 6
  b) HCDRs comprising the amino sequences of SEQ ID NO: 9, 10 and 11 and LCDRs comprising the amino sequences of SEQ ID NO: 12, 13 and 14
  c) HCDRs comprising the amino sequences of SEQ ID NO: 17, 18, 19 and LCDRs comprising the amino sequences of SEQ ID NO: 20, 21 and 22
  d) HCDRs comprising the amino sequences of SEQ ID NO: 25, 26, 27 and LCDRs comprising the amino sequences of SEQ ID NO: 28, 29 and 30
  e) HCDRs comprising the amino sequences of SEQ ID NO: 33, 34 and 35 and LCDRs comprising the amino sequences of SEQ ID NO: 36, 37 and 38
  f) HCDRs comprising the amino sequences of SEQ ID NO: 41, 42 and 43 and LCDRs comprising the amino sequences of SEQ ID NO: 44, 45 and 46 or
  g) HCDRs comprising the amino sequences of SEQ ID NO: 49, 50 and 51 and LCDRs comprising the amino sequences of SEQ ID NO: 52, 53 and 54.

19. The bispecific antibody of claim 14, wherein the chemotherapeutic drug is duocarmycin, calicheamicin, pyrrolobenzodiazepine (PBD), anthracycline, nemorubicin, doxorubicin, Irinotecan, amatoxin, auristatin, maytansine, tubulysin, SN-38, 5-Aminolaevulinic acid (ALA), Benzoporphyrin derivative monoacid ring A (BPD-MA), Chlorins, Tetra (m-hydroxyphenyl)chlorin (mTHPC), or Lutetium texaphyrin.

20. A drug delivery system for delivering a drug to cells expressing a PDGF receptor, comprising the anti-PDGF receptor antibody or antigen-binding fragment thereof according to claim 1.

21. The drug delivery system according to claim 20, which the drug is an immunotherapeutic agent further comprising a chemotherapeutic agent.

22. The drug delivery system of claim 20, further comprising an antibody or antigen-binding fragment thereof against hapten for a chemotherapeutic drug, wherein specifically binds to the anti-PDGF receptor and the hapten.

23. A pharmaceutical composition comprising an anti-PDGF receptor antibody or antigen-binding fragment thereof according to claim 1, or a bispecific antibody which specifically binds to PDGF receptor and hapten and comprises the anti-PDGF receptor antibody or antigen-binding fragment thereof and an antibody or antigen-binding fragment thereof against hapten for a chemotherapeutic drug.

* * * * *

SEQUENCE LISTING

<160> NUMBER OF SEQ ID NOS: 74

<210> SEQ ID NO 1
<211> LENGTH: 10
<212> TYPE: PRT
<213> ORGANISM: Artificial Sequence
<220> FEATURE:
<223> OTHER INFORMATION: CDR1-VH of PRb-CN01

<400> SEQUENCE: 1

Gly Phe Thr Phe Ser Asp Arg Ala Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2-VH of PRb-CN01

<400> SEQUENCE: 2

Leu Ile Thr Asn Thr Gly Gly Ser Thr Asn Tyr Gly Ala Ala Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: CDR3-VH of PRb-CN01

<400> SEQUENCE: 3

Gly Val Gly Ser Trp Ala His Gly Gly Arg Ile Asp Ala
1               5                   10

<210> SEQ ID NO 4
<211> LENGTH: 8
<212> TYPE: PRT
<213> ORGANISM: Artificial Sequence
<220> FEATURE:
<223> OTHER INFORMATION: CDR1-VL of PRb-CN01

<400> SEQUENCE: 4

Ser Gly Gly Ser Gly Ser Tyr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: CDR2-VL of PRb-CN01

<400> SEQUENCE: 5

Ser Asn Asn Gln Arg Pro Ser
1               5

<210> SEQ ID NO 6
<211> LENGTH: 10
<212> TYPE: PRT
<213> ORGANISM: Artificial Sequence
<220> FEATURE:
<223> OTHER INFORMATION: CDR3-VL of PRb-CN01

<400> SEQUENCE: 6

Gly Thr Arg Asp Ser Ser Tyr Val Gly Ile
1               5                   10

<210> SEQ ID NO 7
<211> LENGTH: 122
<212> TYPE: PRT
<213> ORGANISM: Artificial Sequence
<220> FEATURE:
<223> OTHER INFORMATION: VH of PRb-CN01

<400> SEQUENCE: 7

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Asp Arg
            20                  25                  30

Ala Met His Trp Val Arg Gln Ala Pro Gly Lys Gly Leu Glu Trp Val
        35                  40                  45

Gly Leu Ile Thr Asn Thr Gly Gly Ser Thr Asn Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Thr Arg Gly Val Gly Ser Trp Ala His Gly Gly Arg Ile Asp Ala Trp
            100                 105                 110

Gly His Gly Thr Glu Val Ile Val Ser Ser
        115                 120

<210> SEQ ID NO 8
<211> LENGTH: 102
<212> TYPE: PRT
<213> ORGANISM: Artificial Sequence
<220> FEATURE:
<223> OTHER INFORMATION: VL of PRb-CN01

<400> SEQUENCE: 8

Leu Thr Gln Pro Ser Ser Val Ser Ala Asn Pro Gly Glu Thr Val Lys
1               5                   10                  15

Ile Thr Cys Ser Gly Gly Ser Gly Ser Tyr Gly Trp Phe Gln Gln Lys
            20                  25                  30

Ser Pro Gly Ser Ala Pro Val Thr Val Ile Tyr Ser Asn Asn Gln Arg
        35                  40                  45

Pro Ser Asp Ile Pro Ser Arg Phe Ser Gly Ser Lys Ser Gly Ser Thr
    50                  55                  60

Asn Thr Leu Thr Ile Thr Gly Val Gln Ala Glu Asp Glu Ala Ile Tyr
65                  70                  75                  80

Tyr Cys Gly Thr Arg Asp Ser Ser Tyr Val Gly Ile Phe Gly Ala Gly
                85                  90                  95

Thr Thr Leu Thr Val Leu
            100

<210> SEQ ID NO 9
<211> LENGTH: 11
<212> TYPE: PRT
<213> ORGANISM: Artificial Sequence
<220> FEATURE:
<223> OTHER INFORMATION: CDR1-VH of PRb-CC01

<400> SEQUENCE: 9

Ser Gly Phe Thr Phe Ser Ser Tyr Asn Met Gly

<210> SEQ ID NO 10
<211> LENGTH: 17
<212> TYPE: PRT
<213> ORGANISM: Artificial Sequence
<220> FEATURE:
<223> OTHER INFORMATION: CDR2-VH of PRb-CC01

<400> SEQUENCE: 10

Gly Ile Ser Ala Ala Asp Asn Ser Thr Ala Tyr Gly Ala Ala Val Asp
1               5                   10                  15
Gly

<210> SEQ ID NO 11
<211> LENGTH: 7
<212> TYPE: PRT
<213> ORGANISM: Artificial Sequence
<220> FEATURE:
<223> OTHER INFORMATION: CDR3-VH of PRb-CC01

<400> SEQUENCE: 11

Gly Gly Gly Ser Ile Asp Ala
1               5

<210> SEQ ID NO 12
<211> LENGTH: 8
<212> TYPE: PRT
<213> ORGANISM: Artificial Sequence
<220> FEATURE:
<223> OTHER INFORMATION: CDR1-VL of PRb-CC01

<400> SEQUENCE: 12

Ser Gly Gly Gly Ser Tyr Tyr Gly
1               5

<210> SEQ ID NO 13
<211> LENGTH: 7
<212> TYPE: PRT
<213> ORGANISM: Artificial Sequence
<220> FEATURE:
<223> OTHER INFORMATION: CDR2-VL of PRb-CC01

<400> SEQUENCE: 13

Tyr Asn Asp Lys Arg Pro Ser
1               5

<210> SEQ ID NO 14
<211> LENGTH: 11
<212> TYPE: PRT
<213> ORGANISM: Artificial Sequence
<220> FEATURE:
<223> OTHER INFORMATION: CDR3-VL of PRb-CC01

<400> SEQUENCE: 14

Gly Ala Trp Asp Asn Ser Ala Gly Tyr Ala Gly
1               5                   10

<210> SEQ ID NO 15
<211> LENGTH: 116
<212> TYPE: PRT
<213> ORGANISM: Artificial Sequence
<220> FEATURE:
<223> OTHER INFORMATION: VH of PRb-CC01

<400> SEQUENCE: 15

```
Ala Val Thr Leu Asp Glu Ser Gly Gly Leu Gln Thr Pro Gly Gly
1               5                   10                  15

Ala Leu Ser Leu Val Cys Lys Gly Ser Gly Phe Thr Phe Ser Ser Tyr
                20                  25                  30

Asn Met Gly Trp Val Arg Gln Ala Pro Gly Lys Gly Leu Glu Phe Val
            35                  40                  45

Ala Gly Ile Ser Ala Ala Asp Asn Ser Thr Ala Tyr Gly Ala Ala Val
50                  55                  60

Asp Gly Arg Ala Thr Ile Ser Arg Asp Asn Gln Ser Thr Val Arg
65                  70                  75                  80

Leu Gln Leu Asn Asn Leu Arg Ala Glu Asp Thr Ala Thr Tyr Phe Cys
                85                  90                  95

Ile Arg Gly Gly Gly Ser Ile Asp Ala Trp Gly His Gly Thr Glu Val
            100                 105                 110

Ile Val Ser Ser
            115
```

```
<210> SEQ ID NO 16
<211> LENGTH: 103
<212> TYPE: PRT
<213> ORGANISM: Artificial Sequence
<220> FEATURE:
<223> OTHER INFORMATION: VL of PRb-CC01

<400> SEQUENCE: 16

Leu Thr Gln Pro Ser Ser Val Ser Ala Asn Leu Gly Gly Thr Val Lys
1               5                   10                  15

Ile Thr Cys Ser Gly Gly Gly Ser Tyr Tyr Gly Trp Tyr Gln Gln Lys
                20                  25                  30

Ser Pro Gly Ser Ala Pro Val Thr Leu Ile Tyr Tyr Asn Asp Lys Arg
            35                  40                  45

Pro Ser Asp Ile Pro Ser Arg Phe Ser Gly Ser Lys Ser Gly Ser Thr
50                  55                  60

Gly Thr Leu Thr Ile Thr Gly Val Gln Ala Glu Asp Glu Ala Val Tyr
65                  70                  75                  80

Phe Cys Gly Ala Trp Asp Asn Ser Ala Gly Tyr Ala Gly Phe Gly Ala
                85                  90                  95

Gly Thr Thr Leu Thr Val Leu
            100
```

```
<210> SEQ ID NO 17
<211> LENGTH: 10
<212> TYPE: PRT
<213> ORGANISM: Artificial Sequence
<220> FEATURE:
<223> OTHER INFORMATION: CDR1-VH of PRb-CC02

<400> SEQUENCE: 17

Gly Phe Thr Phe Ser Ser Tyr Gly Met Phe
1               5                   10
```

```
<210> SEQ ID NO 18
<211> LENGTH: 16
<212> TYPE: PRT
<213> ORGANISM: Artificial Sequence
<220> FEATURE:
<223> OTHER INFORMATION: CDR2-VH of PRb-CC02

<400> SEQUENCE: 18

Gly Ile Asp Thr Gly Ser Gly Thr Asn Tyr Gly Ser Ala Val Lys Gly
```

<210> SEQ ID NO 19
<211> LENGTH: 8
<212> TYPE: PRT
<213> ORGANISM: Artificial Sequence
<220> FEATURE:
<223> OTHER INFORMATION: CDR3-VH of PRb-CC02

<400> SEQUENCE: 19

Gly Tyr Ala Gly Thr Ile Asp Ala
1               5

<210> SEQ ID NO 20
<211> LENGTH: 8
<212> TYPE: PRT
<213> ORGANISM: Artificial Sequence
<220> FEATURE:
<223> OTHER INFORMATION: CDR1-V of PRb-CC02

<400> SEQUENCE: 20

Ser Gly Gly Gly Gly Ser Tyr Gly
1               5

<210> SEQ ID NO 21
<211> LENGTH: 7
<212> TYPE: PRT
<213> ORGANISM: Artificial Sequence
<220> FEATURE:
<223> OTHER INFORMATION: CDR2-VL of PRb-CC02

<400> SEQUENCE: 21

Tyr Asn Asp Lys Arg Pro Ser
1               5

<210> SEQ ID NO 22
<211> LENGTH: 9
<212> TYPE: PRT
<213> ORGANISM: Artificial Sequence
<220> FEATURE:
<223> OTHER INFORMATION: CDR3-VL of PRb-CC02

<400> SEQUENCE: 22

Gly Ser Tyr Asn Ser Ser Asp Ser Leu
1               5

<210> SEQ ID NO 23
<211> LENGTH: 118
<212> TYPE: PRT
<213> ORGANISM: Artificial Sequence
<220> FEATURE:
<223> OTHER INFORMATION: VH of PRb-CC02

<400> SEQUENCE: 23

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
                20                  25                  30

Gly Met Phe Trp Val Arg Gln Ala Pro Gly Lys Gly Leu Glu Trp Val
            35                  40                  45

Ala Gly Ile Asp Thr Gly Ser Gly Thr Asn Tyr Gly Ser Ala Val Lys
        50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Gly Thr Tyr Phe Cys Thr
                85                  90                  95

Arg Gly Tyr Ala Gly Thr Ile Asp Ala Trp Gly His Gly Thr Glu Val
            100                 105                 110

Ile Val Ser Ser Thr Ser
            115

<210> SEQ ID NO 24
<211> LENGTH: 101
<212> TYPE: PRT
<213> ORGANISM: Artificial Sequence
<220> FEATURE:
<223> OTHER INFORMATION: VL of PRb-CC02

<400> SEQUENCE: 24

Leu Thr Gln Pro Ser Ser Val Ser Ala Asn Pro Gly Glu Thr Val Lys
1               5                   10                  15

Ile Thr Cys Ser Gly Gly Gly Ser Tyr Gly Trp Tyr Gln Gln Lys
            20                  25                  30

Ser Pro Gly Ser Ala Pro Val Thr Val Ile Tyr Tyr Asn Asp Lys Arg
            35                  40                  45

Pro Ser Asp Ile Pro Ser Arg Phe Ser Gly Ser Lys Ser Gly Ser Thr
    50                  55                  60

Gly Thr Leu Thr Ile Thr Gly Val Gln Ala Glu Asp Glu Ala Val Tyr
65                  70                  75                  80

Phe Cys Gly Ser Tyr Asn Ser Ser Asp Ser Leu Phe Gly Ala Gly Thr
                85                  90                  95

Thr Leu Thr Val Leu
            100

<210> SEQ ID NO 25
<211> LENGTH: 10
<212> TYPE: PRT
<213> ORGANISM: Artificial Sequence
<220> FEATURE:
<223> OTHER INFORMATION: CDR1-VH of PRb-CC03

<400> SEQUENCE: 25

Gly Phe Thr Phe Ser Ser Tyr Ala Met Gly
1               5                   10

<210> SEQ ID NO 26
<211> LENGTH: 16
<212> TYPE: PRT
<213> ORGANISM: Artificial Sequence
<220> FEATURE:
<223> OTHER INFORMATION: CDR2-VH of PRb-CC03

<400> SEQUENCE: 26

Gly Ile Asp Thr Ala Gly Gly Thr Ala Tyr Gly Pro Ala Val Lys Gly
1               5                   10                  15

<210> SEQ ID NO 27
<211> LENGTH: 6
<212> TYPE: PRT
<213> ORGANISM: Artificial Sequence
<220> FEATURE:
<223> OTHER INFORMATION: CDR3-VH of PRb-CC03

<400> SEQUENCE: 27

Ser Ser Tyr Ile Asp Thr
1               5

<210> SEQ ID NO 28
<211> LENGTH: 8
<212> TYPE: PRT
<213> ORGANISM: Artificial Sequence
<220> FEATURE:
<223> OTHER INFORMATION: CDR1-VL of PRb-CC03

<400> SEQUENCE: 28

Ser Gly Gly Thr Tyr Asn Tyr Gly
1               5

<210> SEQ ID NO 29
<211> LENGTH: 7
<212> TYPE: PRT
<213> ORGANISM: Artificial Sequence
<220> FEATURE:
<223> OTHER INFORMATION: CDR2-VL of PRb-CC03

<400> SEQUENCE: 29

Trp Asn Asp Lys Arg Pro Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDR3-VL of PRb-CC03

<400> SEQUENCE: 30

Gly Ser Ser Asp Ser Ser Gly Leu Ile
1               5

<210> SEQ ID NO 31
<211> LENGTH: 116
<212> TYPE: PRT
<213> ORGANISM: Artificial Sequence
<220> FEATURE:
<223> OTHER INFORMATION: VH of PRb-CC03

<400> SEQUENCE: 31

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ala Gly Ile Asp Thr Ala Gly Thr Ala Tyr Gly Pro Ala Val Lys
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Ala Thr Tyr Tyr Cys Thr
                85                  90                  95

Arg Ser Ser Tyr Ile Asp Thr Trp Gly His Gly Thr Glu Val Ile Val
            100                 105                 110

Ser Ser Thr Ser
        115

<210> SEQ ID NO 32
<211> LENGTH: 101
<212> TYPE: PRT
<213> ORGANISM: Artificial Sequence
<220> FEATURE:

<223> OTHER INFORMATION: VL of PRb-CC03

<400> SEQUENCE: 32

Leu Thr Gln Pro Ser Ser Val Ser Ala Asn Pro Gly Glu Thr Val Lys
1               5                   10                  15

Ile Thr Cys Ser Gly Gly Thr Tyr Asn Tyr Gly Trp Tyr Gln Gln Lys
                20                  25                  30

Ser Pro Gly Ser Ala Pro Val Thr Val Ile Tyr Trp Asn Asp Lys Arg
            35                  40                  45

Pro Ser Asp Ile Pro Ser Arg Phe Ser Gly Ser Lys Ser Gly Ser Thr
        50                  55                  60

Gly Thr Leu Thr Ile Thr Gly Val Gln Ala Glu Asp Glu Ala Val Tyr
65                  70                  75                  80

Tyr Cys Gly Ser Ser Asp Ser Ser Gly Leu Ile Phe Gly Ala Gly Thr
                85                  90                  95

Thr Leu Thr Val Leu
            100

<210> SEQ ID NO 33
<211> LENGTH: 10
<212> TYPE: PRT
<213> ORGANISM: Artificial Sequence
<220> FEATURE:
<223> OTHER INFORMATION: CDR1-VH of PRb-CN16

<400> SEQUENCE: 33

Gly Phe Thr Phe Ser Ser Phe Asn Met Ala
1               5                   10

<210> SEQ ID NO 34
<211> LENGTH: 17
<212> TYPE: PRT
<213> ORGANISM: Artificial Sequence
<220> FEATURE:
<223> OTHER INFORMATION: CDR2-VH of PRb-CN16

<400> SEQUENCE: 34

Glu Ile Ser Asn Thr Ala Gly Ser Thr Phe Tyr Ala Pro Ala Val Lys
1               5                   10                  15

Gly

<210> SEQ ID NO 35
<211> LENGTH: 16
<212> TYPE: PRT
<213> ORGANISM: Artificial Sequence
<220> FEATURE:
<223> OTHER INFORMATION: CDR3-VH of PRb-CN16

<400> SEQUENCE: 35

Ala Ala Gly Thr Cys Tyr Ser His Ser Cys Thr Gly Tyr Ile Asp Ala
1               5                   10                  15

<210> SEQ ID NO 36
<211> LENGTH: 8
<212> TYPE: PRT
<213> ORGANISM: Artificial Sequence
<220> FEATURE:
<223> OTHER INFORMATION: CDR1-VL of PRb-CN16

<400> SEQUENCE: 36

Ser Gly Ser Ser Ser Ser Tyr Gly
1               5

<210> SEQ ID NO 37
<211> LENGTH: 7
<212> TYPE: PRT
<213> ORGANISM: Artificial Sequence
<220> FEATURE:
<223> OTHER INFORMATION: CDR2-VL of PRb-CN16

<400> SEQUENCE: 37

Glu Asn Asn Gln Arg Pro Ser
1               5

<210> SEQ ID NO 38
<211> LENGTH: 11
<212> TYPE: PRT
<213> ORGANISM: Artificial Sequence
<220> FEATURE:
<223> OTHER INFORMATION: CDR3-VL of PRb-CN16

<400> SEQUENCE: 38

Gly Asn Ala Asp Arg Ser Asn Ser Ala Gly Thr
1               5                   10

<210> SEQ ID NO 39
<211> LENGTH: 127
<212> TYPE: PRT
<213> ORGANISM: Artificial Sequence
<220> FEATURE:
<223> OTHER INFORMATION: VH of PRb-CN16

<400> SEQUENCE: 39

Ala Val Thr Leu Asp Glu Ser Gly Gly Gly Leu Gln Thr Pro Gly Thr
1               5                   10                  15

Ala Leu Ser Leu Val Cys Lys Ala Ser Gly Phe Thr Phe Ser Ser Phe
            20                  25                  30

Asn Met Ala Trp Val Arg Gln Ala Pro Gly Lys Gly Leu Glu Phe Val
        35                  40                  45

Gly Glu Ile Ser Asn Thr Ala Gly Ser Thr Phe Tyr Ala Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Tyr Cys
                85                  90                  95

Ala Lys Ala Ala Gly Thr Cys Tyr Ser His Ser Cys Thr Gly Tyr Ile
            100                 105                 110

Asp Ala Trp Gly His Gly Thr Glu Val Ile Val Ser Ser Thr Ser
        115                 120                 125

<210> SEQ ID NO 40
<211> LENGTH: 103
<212> TYPE: PRT
<213> ORGANISM: Artificial Sequence
<220> FEATURE:
<223> OTHER INFORMATION: VL of PRb-CN16

<400> SEQUENCE: 40

Leu Thr Gln Pro Ser Ser Val Ser Ala Asn Pro Gly Glu Thr Val Lys
1               5                   10                  15

Ile Thr Cys Ser Gly Ser Ser Ser Tyr Gly Trp Tyr Gln Gln Lys
            20                  25                  30

Ser Pro Gly Ser Ala Pro Val Thr Leu Ile Tyr Glu Asn Asn Gln Arg
        35                  40                  45

```
Pro Ser Asn Ile Pro Ser Arg Phe Ser Gly Ser Lys Ser Gly Ser Thr
    50                  55                  60

Gly Thr Leu Thr Ile Thr Gly Val Gln Ala Glu Asp Glu Ala Val Tyr
65                  70                  75                  80

Tyr Cys Gly Asn Ala Asp Arg Ser Asn Ser Ala Gly Thr Phe Gly Ala
                85                  90                  95

Gly Thr Thr Leu Thr Val Leu
            100

<210> SEQ ID NO 41
<211> LENGTH: 10
<212> TYPE: PRT
<213> ORGANISM: Artificial Sequence
<220> FEATURE:
<223> OTHER INFORMATION: CDR1-VH of PRb-CN32

<400> SEQUENCE: 41

Gly Phe Thr Phe Ser Ser Phe Asn Met Phe
1               5                   10

<210> SEQ ID NO 42
<211> LENGTH: 17
<212> TYPE: PRT
<213> ORGANISM: Artificial Sequence
<220> FEATURE:
<223> OTHER INFORMATION: CDR2-VH of PRb-CN32

<400> SEQUENCE: 42

Gly Ile Ser Thr Thr Gly Arg Tyr Thr Gly Tyr Gly Ser Ala Val Gln
1               5                   10                  15

Gly

<210> SEQ ID NO 43
<211> LENGTH: 18
<212> TYPE: PRT
<213> ORGANISM: Artificial Sequence
<220> FEATURE:
<223> OTHER INFORMATION: CDR3-VH of PRb-CN32

<400> SEQUENCE: 43

Ser Ala Gly Ser Thr Tyr Ser Tyr Trp Asp Ser Asp Ala Gly Leu Ile
1               5                   10                  15

Asp Ala

<210> SEQ ID NO 44
<211> LENGTH: 12
<212> TYPE: PRT
<213> ORGANISM: Artificial Sequence
<220> FEATURE:
<223> OTHER INFORMATION: CDR1-VL of PRb-CN32

<400> SEQUENCE: 44

Ser Gly Gly Ser Asn Ala Gly Ser Tyr Tyr Tyr Gly
1               5                   10

<210> SEQ ID NO 45
<211> LENGTH: 7
<212> TYPE: PRT
<213> ORGANISM: Artificial Sequence
<220> FEATURE:
<223> OTHER INFORMATION: CDR2-VL of PRb-CN32

<400> SEQUENCE: 45

Ser Asn Asn Gln Arg Pro Ser
1               5
```

<210> SEQ ID NO 46
<211> LENGTH: 10
<212> TYPE: PRT
<213> ORGANISM: Artificial Sequence
<220> FEATURE:
<223> OTHER INFORMATION: CDR3-VL of PRb-CN32

<400> SEQUENCE: 46

Gly Ser Gly Asp Ser Ser Ser Ile Ala Ala
1               5                   10

<210> SEQ ID NO 47
<211> LENGTH: 129
<212> TYPE: PRT
<213> ORGANISM: Artificial Sequence
<220> FEATURE:
<223> OTHER INFORMATION: VH of PRb-CN32

<400> SEQUENCE: 47

Ala Val Thr Leu Asp Glu Ser Gly Gly Gly Leu Gln Thr Pro Arg Gly
1               5                   10                  15

Thr Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Phe Val
        35                  40                  45

Ala Gly Ile Ser Thr Thr Gly Arg Tyr Thr Tyr Gly Ser Ala Val
    50                  55                  60

Gln Gly Arg Gly Thr Ile Ser Arg Asp Asn Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ser Ala Gly Ser Thr Tyr Ser Tyr Trp Asp Ser Asp Ala Gly
            100                 105                 110

Leu Ile Asp Ala Trp Gly His Gly Thr Glu Val Ile Val Ser Ser Thr
        115                 120                 125

Ser

<210> SEQ ID NO 48
<211> LENGTH: 106
<212> TYPE: PRT
<213> ORGANISM: Artificial Sequence
<220> FEATURE:
<223> OTHER INFORMATION: VL of PRb-CN32

<400> SEQUENCE: 48

Leu Thr Gln Pro Ser Ser Val Ser Ala Asn Leu Gly Glu Thr Val Lys
1               5                   10                  15

Ile Thr Cys Ser Gly Gly Ser Asn Ala Gly Ser Tyr Tyr Tyr Gly Trp
            20                  25                  30

Tyr Gln Gln Lys Ser Pro Gly Ser Ala Pro Val Thr Val Ile Tyr Ser
        35                  40                  45

Asn Asn Gln Arg Pro Ser Asp Ile Pro Ser Arg Phe Ser Gly Ser Thr
    50                  55                  60

Ser Gly Ser Thr Ser Thr Leu Thr Ile Thr Gly Val Gln Val Asp Asp
65                  70                  75                  80

Glu Ala Val Tyr Phe Cys Gly Ser Gly Asp Ser Ser Ser Ile Ala Ala
                85                  90                  95

Phe Gly Ala Gly Thr Thr Leu Thr Val Leu
            100                 105

<210> SEQ ID NO 49
<211> LENGTH: 10
<212> TYPE: PRT
<213> ORGANISM: Artificial Sequence
<220> FEATURE:
<223> OTHER INFORMATION: CDR1-VH of PRb-CN26

<400> SEQUENCE: 49

Gly Phe Thr Phe Ser Asp Arg Gly Ile His
1               5                   10

<210> SEQ ID NO 50
<211> LENGTH: 17
<212> TYPE: PRT
<213> ORGANISM: Artificial Sequence
<220> FEATURE:
<223> OTHER INFORMATION: CDR2-VH of PRb-CN26

<400> SEQUENCE: 50

Gly Ile Gly Asn Thr Gly Ser Tyr Thr Ala Tyr Ala Pro Ala Val Lys
1               5                   10                  15

Gly

<210> SEQ ID NO 51
<211> LENGTH: 11
<212> TYPE: PRT
<213> ORGANISM: Artificial Sequence
<220> FEATURE:
<223> OTHER INFORMATION: CDR3-VH of PRb-CN26

<400> SEQUENCE: 51

Arg Gly Phe Met Asp Ala Gly Gly Ile Asp Ala
1               5                   10

<210> SEQ ID NO 52
<211> LENGTH: 13
<212> TYPE: PRT
<213> ORGANISM: Artificial Sequence
<220> FEATURE:
<223> OTHER INFORMATION: CDR1-VL of PRb-CN26

<400> SEQUENCE: 52

Ser Gly Gly Gly Ser Tyr Ala Gly Ser Tyr Tyr Tyr Gly
1               5                   10

<210> SEQ ID NO 53
<211> LENGTH: 7
<212> TYPE: PRT
<213> ORGANISM: Artificial Sequence
<220> FEATURE:
<223> OTHER INFORMATION: CDR2-VL of PRb-CN26

<400> SEQUENCE: 53

Asp Asn Thr Asn Arg Pro Ser
1               5

<210> SEQ ID NO 54
<211> LENGTH: 11
<212> TYPE: PRT
<213> ORGANISM: Artificial Sequence
<220> FEATURE:
<223> OTHER INFORMATION: CDR3-VL of PRb-CN26

<400> SEQUENCE: 54

Gly Gly Tyr Asp Gly Ile Ser Asp Thr Gly Ile
1               5                   10

<210> SEQ ID NO 55
<211> LENGTH: 122
<212> TYPE: PRT
<213> ORGANISM: Artificial Sequence
<220> FEATURE:
<223> OTHER INFORMATION: VH of PRb-CN26

<400> SEQUENCE: 55

Ala Val Thr Leu Asp Glu Ser Gly Gly Leu Gln Thr Pro Gly Gly
1               5                   10                  15

Gly Leu Ser Leu Val Cys Lys Ala Ser Gly Phe Thr Phe Ser Asp Arg
            20                  25                  30

Gly Ile His Trp Val Arg Gln Ala Pro Gly Lys Gly Leu Glu Trp Val
        35                  40                  45

Ala Gly Ile Gly Asn Thr Gly Ser Tyr Thr Ala Tyr Ala Pro Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Arg Gly Phe Met Asp Ala Gly Gly Ile Asp Ala Trp Gly His
            100                 105                 110

Gly Thr Glu Val Ile Val Ser Ser Thr Ser
        115                 120

<210> SEQ ID NO 56
<211> LENGTH: 108
<212> TYPE: PRT
<213> ORGANISM: Artificial Sequence
<220> FEATURE:
<223> OTHER INFORMATION: VL of PRb-CN26

<400> SEQUENCE: 56

Leu Thr Gln Pro Ser Ser Val Ser Ala Asn Pro Gly Glu Thr Val Lys
1               5                   10                  15

Ile Thr Cys Ser Gly Gly Gly Ser Tyr Ala Gly Ser Tyr Tyr Tyr Gly
            20                  25                  30

Trp Tyr Gln Gln Lys Ser Pro Gly Ser Ala Pro Val Thr Val Ile Tyr
        35                  40                  45

Asp Asn Thr Asn Arg Pro Ser Asn Ile Pro Ser Arg Phe Ser Gly Ser
    50                  55                  60

Leu Ser Gly Ser Thr Asp Thr Leu Thr Ile Thr Gly Val Gln Ala Glu
65                  70                  75                  80

Asp Glu Ala Val Tyr Phe Cys Gly Gly Tyr Asp Gly Ile Ser Asp Thr
                85                  90                  95

Gly Ile Phe Gly Ala Gly Thr Thr Leu Thr Val Leu
            100                 105

<210> SEQ ID NO 57
<211> LENGTH: 18
<212> TYPE: PRT
<213> ORGANISM: Artificial Sequence
<220> FEATURE:
<223> OTHER INFORMATION: Linker for VL-VH in scFv

<400> SEQUENCE: 57

```
Gly Gln Ser Ser Arg Ser Gly Gly Gly Ser Ser Gly Gly Gly
1               5                   10                  15

Gly Ser
```

<210> SEQ ID NO 58
<211> LENGTH: 107
<212> TYPE: PRT
<213> ORGANISM: Artificial Sequence
<220> FEATURE:
<223> OTHER INFORMATION: Kappa constant (Ck)

<400> SEQUENCE: 58

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Leu
                85                  90                  95

Pro Val Thr Lys Ser Phe Asn Arg Gly Glu Ser
            100                 105
```

<210> SEQ ID NO 59
<211> LENGTH: 15
<212> TYPE: PRT
<213> ORGANISM: Artificial Sequence
<220> FEATURE:
<223> OTHER INFORMATION: Linker for scFv-Ck

<400> SEQUENCE: 59

```
Gly Gly Gly Gly Ser Gly Gly Gly Ser Gly Gly Gly Gly Ser
1               5                   10                  15
```

<210> SEQ ID NO 60
<211> LENGTH: 255
<212> TYPE: PRT
<213> ORGANISM: Artificial Sequence
<220> FEATURE:
<223> OTHER INFORMATION: hPDGFR-beta Extracellular domain

<400> SEQUENCE: 60

```
Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110
```

```
Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly
                245                 250                 255

<210> SEQ ID NO 61
<211> LENGTH: 255
<212> TYPE: PRT
<213> ORGANISM: Artificial Sequence
<220> FEATURE:
<223> OTHER INFORMATION: mPDGFR-beta Extracellular domain

<400> SEQUENCE: 61

Leu Val Ile Thr Pro Gly Pro Glu Phe Val Leu Asn Ile Ser Ser
1               5                   10                  15

Thr Phe Val Leu Thr Cys Ser Gly Ser Ala Pro Val Met Trp Glu Gln
            20                  25                  30

Met Ser Gln Val Pro Trp Gln Glu Ala Ala Met Asn Gln Asp Gly Thr
        35                  40                  45

Phe Ser Ser Val Leu Thr Leu Thr Asn Val Thr Gly Gly Asp Thr Gly
    50                  55                  60

Glu Tyr Phe Cys Val Tyr Asn Asn Ser Leu Gly Pro Glu Leu Ser Glu
65                  70                  75                  80

Arg Lys Arg Ile Tyr Ile Phe Val Pro Asp Pro Thr Met Gly Phe Leu
                85                  90                  95

Pro Met Asp Ser Glu Asp Leu Phe Ile Phe Val Thr Asp Val Thr Glu
            100                 105                 110

Thr Thr Ile Pro Cys Arg Val Thr Asp Pro Gln Leu Glu Val Thr Leu
        115                 120                 125

His Glu Lys Lys Val Asp Ile Pro Leu His Val Pro Tyr Asp His Gln
    130                 135                 140

Arg Gly Phe Thr Gly Thr Phe Glu Asp Lys Thr Tyr Ile Cys Lys Thr
145                 150                 155                 160

Thr Ile Gly Asp Arg Glu Val Asp Ser Asp Thr Tyr Tyr Val Tyr Ser
                165                 170                 175

Leu Gln Val Ser Ser Ile Asn Val Ser Val Asn Ala Val Gln Thr Val
            180                 185                 190

Val Arg Gln Gly Glu Ser Ile Thr Ile Arg Cys Ile Val Met Gly Asn
        195                 200                 205

Asp Val Val Asn Phe Gln Trp Thr Tyr Pro Arg Met Lys Ser Gly Arg
    210                 215                 220
```

```
Leu Val Glu Pro Val Thr Asp Tyr Leu Phe Gly Val Pro Ser Arg Ile
225                 230                 235                 240

Gly Ser Ile Leu His Ile Pro Thr Ala Glu Leu Ser Asp Ser Gly
                245                 250                 255

<210> SEQ ID NO 62
<211> LENGTH: 255
<212> TYPE: PRT
<213> ORGANISM: Artificial Sequence
<220> FEATURE:
<223> OTHER INFORMATION: PDGFR-beta of Cynomolgus monkey

<400> SEQUENCE: 62

Met Arg Leu Pro Gly Ala Met Pro Ala Leu Ala Leu Lys Gly Gln Leu
1               5                   10                  15

Leu Leu Leu Pro Leu Leu Leu Leu Glu Pro Gln Val Ser Gln Gly
                20                  25                  30

Leu Val Ile Thr Pro Pro Gly Pro Glu Leu Ile Leu Asn Val Ser Ser
                35                  40                  45

Thr Phe Val Leu Thr Cys Ser Gly Ser Ala Pro Val Val Trp Glu Arg
    50                  55                  60

Met Ser Gln Glu Leu Pro Gln Glu Met Ala Lys Ala Gln Asp Asn Thr
65                  70                  75                  80

Phe Ser Ser Val Leu Thr Leu Thr Asn Leu Thr Gly Leu Asp Thr Gly
                85                  90                  95

Glu Tyr Phe Cys Thr Tyr Asn Asp Ser Arg Gly Leu Glu Pro Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Ile Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Met Tyr Pro Arg Lys Glu Ser Gly
                245                 250                 255

<210> SEQ ID NO 63
<211> LENGTH: 255
<212> TYPE: PRT
<213> ORGANISM: Artificial Sequence
<220> FEATURE:
<223> OTHER INFORMATION: PDGFR-beta of Sus scrofa

<400> SEQUENCE: 63

Met Gln Leu Pro Arg Ala Val Pro Ala Ser Val Leu Ile Gly Gln Val
1               5                   10                  15

Leu Leu Leu Pro Pro Leu Leu Leu Leu Gly Pro Gln Ala Ser Trp Gly
```

```
                    20                  25                  30
Leu Val Ile Thr Pro Gly Pro Glu Leu Val Leu Asn Leu Ser Ser
                35                  40                  45

Thr Phe Val Leu Thr Cys Ser Gly Pro Ala Pro Val Val Trp Glu Arg
    50                  55                  60

Met Ser Gln Lys Pro Pro Gln Glu Met Thr Gly Thr Gln Asp Gly Thr
65                  70                  75                  80

Phe Ser Ser Val Leu Thr Leu Ala Asn Val Thr Gly Leu Asp Thr Gly
                85                  90                  95

Glu Tyr Phe Cys Thr Tyr Lys Gly Ser Pro Gly Leu Glu Ala Ser Glu
                100                 105                 110

Arg Lys Arg Leu Tyr Ile Phe Val Pro Asp Pro Ala Val Gly Phe Leu
            115                 120                 125

Pro Val Asp Pro Glu Glu Leu Phe Ile Phe Leu Thr Glu Ile Thr Glu
        130                 135                 140

Thr Thr Ile Pro Cys Arg Val Thr Asp Pro Arg Leu Val Val Thr Leu
145                 150                 155                 160

His Glu Lys Lys Val Asp Val Pro Leu Pro Ile Ser Tyr Asp His Gln
                165                 170                 175

Arg Gly Phe Ser Gly Thr Phe Glu Asp Lys Thr Tyr Val Cys Lys Thr
                180                 185                 190

Thr Ile Gly Asp Arg Glu Val Asp Ser Asp Ala Tyr Tyr Val Tyr Ser
            195                 200                 205

Leu Gln Val Ser Ser Ile Asn Val Ser Val Gly Ala Val Gln Thr Val
        210                 215                 220

Val Arg Gln Gly Glu Asn Ile Thr Val Met Cys Ile Val Thr Gly Asn
225                 230                 235                 240

Glu Val Val Asn Phe Glu Trp Thr Tyr Pro Arg Leu Glu Thr Gly
                245                 250                 255
```

<210> SEQ ID NO 64
<211> LENGTH: 9
<212> TYPE: PRT
<213> ORGANISM: Artificial Sequence
<220> FEATURE:
<223> OTHER INFORMATION: CDR1-VH of anti-Cotinine antibody

<400> SEQUENCE: 64

```
Gly His Leu Arg Arg Arg Asp Trp Met
1               5
```

<210> SEQ ID NO 65
<211> LENGTH: 7
<212> TYPE: PRT
<213> ORGANISM: Artificial Sequence
<220> FEATURE:
<223> OTHER INFORMATION: CDR2-VH of anti-Cotinine antibody

<400> SEQUENCE: 65

```
Ile Gly Arg Ser Gly Asp Thr
1               5
```

<210> SEQ ID NO 66
<211> LENGTH: 11
<212> TYPE: PRT
<213> ORGANISM: Artificial Sequence
<220> FEATURE:
<223> OTHER INFORMATION: CDR3-VH of anti-Cotinine antibody

<400> SEQUENCE: 66

```
Ile Pro Tyr Phe Gly Trp Asn Asn Gly Asp Ile
1               5                   10

<210> SEQ ID NO 67
<211> LENGTH: 13
<212> TYPE: PRT
<213> ORGANISM: Artificial Sequence
<220> FEATURE:
<223> OTHER INFORMATION: CDR1-VL of anti-Cotinine antibody

<400> SEQUENCE: 67

Gln Ser Ser Gln Ser Pro Tyr Ser Asn Glu Trp Leu Ser
1               5                   10

<210> SEQ ID NO 68
<211> LENGTH: 7
<212> TYPE: PRT
<213> ORGANISM: Artificial Sequence
<220> FEATURE:
<223> OTHER INFORMATION: CDR2-VL of anti-Cotinine antibody

<400> SEQUENCE: 68

Arg Ile Ser Thr Leu Ala Ser
1               5

<210> SEQ ID NO 69
<211> LENGTH: 12
<212> TYPE: PRT
<213> ORGANISM: Artificial Sequence
<220> FEATURE:
<223> OTHER INFORMATION: CDR3-VL of anti-Cotinine antibody

<400> SEQUENCE: 69

Ala Gly Gly Tyr Asn Phe Gly Leu Phe Leu Phe Gly
1               5                   10

<210> SEQ ID NO 70
<211> LENGTH: 119
<212> TYPE: PRT
<213> ORGANISM: Artificial Sequence
<220> FEATURE:
<223> OTHER INFORMATION: VH of anti-Cotinine antibody

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly His Leu Arg Arg Arg Asp
            20                  25                  30

Trp Met Asn Trp Val Arg Gln Ala Pro Gly Lys Gly Leu Glu Trp Val
        35                  40                  45

Ala Ala Ile Gly Arg Ser Gly Asp Thr Tyr Tyr Ala Thr Trp Ala Lys
    50                  55                  60

Gly Arg Phe Thr Ile Ser Ala Asp Thr Ser Lys Asn Thr Ala Tyr Leu
65                  70                  75                  80

Gln Met Asn Ser Leu Arg Ala Glu Asp Thr Ala Val Tyr Tyr Cys Ser
                85                  90                  95

Arg Ile Pro Tyr Phe Gly Trp Asn Asn Gly Asp Ile Trp Gly Gln Gly
            100                 105                 110

Thr Leu Val Thr Val Ser Ser
        115

<210> SEQ ID NO 71
```

<211> LENGTH: 110
<212> TYPE: PRT
<213> ORGANISM: Artificial Sequence
<220> FEATURE:
<223> OTHER INFORMATION: VL of anti-Cotinine antibody

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Pro Tyr Ser Asn
            20                  25                  30

Glu Trp Leu Ser Trp Tyr Gln Gln Lys Pro Gly Lys Ala Pro Lys Leu
        35                  40                  45

Leu Ile Tyr Arg Ile Ser Thr Leu Ala Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Asn Phe
                85                  90                  95

Gly Leu Phe Leu Phe Gly Gln Gly Thr Lys Val Glu Ile Lys
            100                 105                 110

<210> SEQ ID NO 72
<211> LENGTH: 214
<212> TYPE: PRT
<213> ORGANISM: Artificial Sequence
<220> FEATURE:
<223> OTHER INFORMATION: Antibody to rabbit Fc

<400> SEQUENCE: 72

Pro Pro Glu Leu Leu Gly Gly Pro Ser Val Phe Ile Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Asp Asp Pro Glu Val Gln Phe Thr Trp Tyr
        35                  40                  45

Ile Asn Asn Glu Gln Val Arg Thr Ala Arg Pro Pro Leu Arg Glu Gln
    50                  55                  60

Gln Phe Asn Ser Thr Ile Arg Val Val Ser Thr Leu Pro Ile Ala His
65                  70                  75                  80

Gln Asp Trp Leu Arg Gly Lys Glu Phe Lys Cys Lys Val His Asn Lys
                85                  90                  95

Ala Leu Pro Ala Pro Ile Glu Lys Thr Ile Ser Lys Ala Arg Gly Gln
            100                 105                 110

Pro Leu Glu Pro Lys Val Tyr Thr Met Gly Pro Pro Arg Glu Glu Leu
        115                 120                 125

Ser Ser Arg Ser Val Ser Leu Thr Cys Met Ile Asn Gly Phe Tyr Pro
    130                 135                 140

Ser Asp Ile Ser Val Glu Trp Glu Lys Asn Gly Lys Ala Glu Asp Asn
145                 150                 155                 160

Tyr Lys Thr Thr Pro Ala Val Leu Asp Ser Asp Gly Ser Tyr Phe Leu
                165                 170                 175

Tyr Ser Lys Leu Ser Val Pro Thr Ser Glu Trp Gln Arg Gly Asp Val
            180                 185                 190

Phe Thr Cys Ser Val Met His Glu Ala Leu His Asn His Tyr Thr Gln
        195                 200                 205

Lys Ser Ile Ser Arg Ser

```
                           -continued
    210

<210> SEQ ID NO 73
<211> LENGTH: 16
<212> TYPE: PRT
<213> ORGANISM: Artificial Sequence
<220> FEATURE:
<223> OTHER INFORMATION: Hinge of linking rabbit Fc and anti-PDGFR-beta
      antibody

<400> SEQUENCE: 73

Gln Glu Pro Lys Ser Ser Asp Lys Thr His Thr Ser Pro Pro Ser Pro
1               5                   10                  15

<210> SEQ ID NO 74
<211> LENGTH: 13
<212> TYPE: PRT
<213> ORGANISM: Artificial Sequence
<220> FEATURE:
<223> OTHER INFORMATION: a peptide conjugated with two trans-4-cotinine
      carboxylic acid molecules

<400> SEQUENCE: 74

Gly Ser Lys Gly Ser Lys Gly Ser Lys Gly Ser Lys Lys
1               5                   10
```